(12) United States Patent
Burke, Jr. et al.

(10) Patent No.: US 6,307,090 B1
(45) Date of Patent: Oct. 23, 2001

(54) ACYLATED OLIGOPEPTIDE DERIVATIVES HAVING CELL SIGNAL INHIBITING ACTIVITY

(75) Inventors: Terrence R. Burke, Jr., Bethesda, MD (US); Zhu-jun Yao, Shanghai (CN); C. Richter King, Washington, DC (US)

(73) Assignee: The United States of America as represented by the Department of Health and Human Services, Washington, DC (US)

(*) Notice: Subject to any disclaimer, the term of this patent is extended or adjusted under 35 U.S.C. 154(b) by 0 days.

(21) Appl. No.: 09/236,160

(22) Filed: Jan. 22, 1999

(51) Int. Cl.[7] ................... C07C 69/76; A61K 38/00; C07F 9/06; C07D 277/62
(52) U.S. Cl. .................... 560/76; 514/2; 514/561; 514/563; 530/300; 548/113; 548/178; 548/179; 548/193; 548/413; 560/82; 562/65
(58) Field of Search ................ 514/2, 561, 563; 530/300; 560/82, 76; 562/65; 558/190; 548/113, 413, 128, 179, 193

(56) References Cited

U.S. PATENT DOCUMENTS 3,906,031   9/1975   Carpino et al. .
4,394,519   7/1983   Carpino et al. .

(List continued on next page.)

FOREIGN PATENT DOCUMENTS

WO 94/07913   4/1994   (WO) .
WO 95/11917   5/1995   (WO) .
WO 96/23813   8/1996   (WO) .
WO 97/08193   3/1997   (WO) .

OTHER PUBLICATIONS

Yao et al. (J. Med. Chem., 1999, 42(1),25–35, Jan. 1999.*
Katunuma, N. et al. J. Biochem. (Tokyo) (1983), 93(4), 1129–35, Jan. 1999.*
Yao et al.; "Potent Inhibition of . . . Ligands", *J. Med. Chem.*, vol. 42, pp. 25–35, 1999, Pub. on Internet Dec. 5, 1998 (copy).

(List continued on next page.)

*Primary Examiner*—Michael Borin

(57) ABSTRACT

The invention relates to an acylated peptide, namely a compound of formula (I),

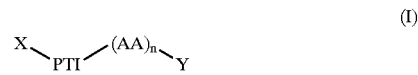

wherein
  n is 0 to 15,
  X is oxalyl
  PTI is the bivalent radical of tyrosine or (preferably) the bivalent radical of phosphotyrosine or a phosphotyrosine mimetic, AA stands for a bivalent radical of a natural or unnatural amino acid, and Y is secondary amino group, or a salt thereof, said compound being useful for the treatment of diseases that respond to inhibition of the interaction of (a) protein(s) comprising (an) SH2 domain(s) and a protein tyrosine kinase or a modified version thereof.

19 Claims, 3 Drawing Sheets pTyr

OxPmp

U.S. PATENT DOCUMENTS

| | | |
|---|---|---|
| 4,879,398 | 11/1989 | Getman et al. . |
| 5,182,263 | 1/1993 | Danho et al. . |
| 5,200,546 | 4/1993 | Burke, Jr. et al. . |
| 5,272,268 | 12/1993 | Toyoda et al. . |
| 5,296,608 | 3/1994 | Danho et al. . |
| 5,369,110 | 11/1994 | Shmidlin et al. . |
| 5,457,114 | 10/1995 | Stuber et al. . |
| 5,463,062 | 10/1995 | Hemmerle et al. . |
| 5,491,253 | 2/1996 | Stuk et al. . |
| 5,508,437 | 4/1996 | Danho et al. . |
| 5,525,733 | 6/1996 | Novack et al. . |
| 5,580,979 | 12/1996 | Bachovchin . |
| 5,587,372 * | 12/1996 | Aszodi et al. . |
| 5,612,370 | 3/1997 | Atwal . |
| 5,616,776 | 4/1997 | Stuk et al. . |
| 5,627,283 | 5/1997 | Stuber et al. . |
| 5,679,842 | 10/1997 | Kleiner . |
| 5,688,992 | 11/1997 | Burke, Jr. et al. . |
| 5,698,731 | 12/1997 | Bosetti et al. . |
| 5,756,817 | 5/1998 | Choi et al. . |
| 5,780,496 | 7/1998 | Tang et al. . |
| 5,786,454 | 7/1998 | Waksman et al. . |
| 5,843,997 | 12/1998 | Heinz et al. . |

OTHER PUBLICATIONS

Burke, Jr., et al. "Potent Inhibition of . . . Ligands", First Annual Meeting on the Experimental Therapeutics of Human Cancer, Jun. 11–13, 1998 Hood College, Frederick, Maryland. (Abstract only).

Allen et al.; "Tritiated Peptides, Part . . . Analogues of Somatostatin", *J. Chem Soc.*, Perkin Trans. 1, pp. 989–1003, 1986.

Ben–Levy et al.; "A single autophosphorylation . . . MAP kinase pathway", *The EMBO Journal*, vol. 13, No. 14, pp. 3302–3311, 1994.

Dankort et al.; "Distinct Tyrosine Autophosphorylation . . . Neu–Mediated Transformation", *Molecular and Cellular Biology*, pp. 5410–5425, Sep. 1997.

Ma et al.; "Bcr phosphorylated on tyrosine 177 binds Grb2", *Oncogene*, vol. 14, pp. 2367–2372, 1997.

Di Fiore et al.; "Overexpression of the. . . NIH 3T3 Cells", *Cell*, vol. 51, pp. 1063–1070, Dec. 24, 1987.

Hudziak et al.; "Increased expression of . . . NIH 3T3 cells", *Proc. Natl. Acad. Sci., USA*, vol. 84, pp. 7159–7163, Oct. 1987.

Kraus et al.; "Overexpression of the . . . different molecular mechanisms", *The EMBO Journal*, vol. 6, No. 3, pp. 605–610, 1987.

Sastry et al.; "Quantitative analysis of . . . Grb2 mediates affinity", *Oncogene*, 11 pp. 1107–1112, 1995.

Searles, Scott; "The Reaction of . . . and Organolithium Compounds", *J. Amer. Chem. soc.*, vol. 73, pp. 124–125, 1951.

Furet, et al.; "Discovery of 3–Aminobenzyloxycarbonyl as an N–Terminal Group Conferring High Affinity to the Minimal Phosphopeptide Sequence Recognized by the Grb2–SH2 Domain", *J. Med. Chem.*, vol. 40, pp. 3551–3556, 1997.

Rahuel et al.; "Structural Basis for the High Affinity of Amino–Aromatic SH2 Phosphopeptide Ligands", *J. Mol. Biol.*, 279, pp. 1013–1022, 1998.

García–Echeverría, et al.; "Potent Antagonists of the SH2 Domain of Grb2: Optimization of the $X_{+1}$–Position of 3–Amino–Z–Tyr($PO_3H_2$)–$X_{-1}$–Asn–$NH_2$", *Journal of Medicinal Chemistry*, vol. 41, No. 11, pp. 1741–1744, May 21, 1988.

Rahuel, et al.; "Structural basis for specificity of GRB2–SH2 revealed by a novel ligand binding mode"; *Nature Structural Biology*, vol. 3, No. 7, pp. 586–589, Jul. 7, 1996.

Burke, et al., "Phosphotyrosyl–Based Motifs in the Structure–Based Design of Protein–Tyrosine Kinase–Dependent Signal Transduction Inhibitors", *Current Pharmaceutical Design*, vol. 3, pp. 291–304, 1997.

Ye et al.; "L–O–(2–Malonyl) tyrosine (L–OMT) a New Phosphotyrosyl Mimic Suitably Protected for Solid–Phase Synthesis of Signal Transduction Inhibitory Peptides", *Tetrahedron Letters*, vol. 36, No. 27, pp. 4733–4736, 1995.

Kuriyan et al.; "Modular Peptide Recognition Domains In Eurkaryotic Signaling", *Annu. Rev. Biophys. Biomol. Struct.*, vol. 26, pp. 259–288, 1997.

Mayer, et al.; "Functions of SH2 and SH3 Domains", *Protein Molecules in Signal Transduction*, vol. 228, pp. 1–22, 1998.

Fry, et al.; "New insights into protein–tyrosine kinase receptor signaling complexes", *Protein Science*, vol. 2, pp. 1785–1797, 1993.

Levitzki, Alexander; "Targeting signal transduction for disease therapy", *Cell Regulation*, pp. 239–244, 1996.

Boutin, Jean A.; "Tyrosine Protein Kinase Inhibition and Cancer", *Int. J. Biochem.*, vol. 26, No. 10/11, pp. 1203–1226, 1994.

Levitzki, et al.; "Tyrosine Kinase Inhibition: An Approach to Drug Development", *Science*, vol. 267, pp. 1782–1788, Mar. 24, 1995.

Lawrence, et al.; "Protein Kinase Inhibitors: The Tyrosine–Specific Protein Kinases", *Pharmacol, Ther.*, vol. 77, No. 2, pp. 81–114, 1998.

Burke, Jr., et al.; "Protein–Tyrosine Phosphatases: Structure, Mechanism, and Inhibitor Discovery", *Biopolymers (Peptide Science)*, vol. 47, pp. 225–241, 1998.

Shoelson, Steven E.; "SH2 and PTB domain interactions in tyrosine kinase signal transduction", *Current Opinion in Chemical Biology*, pp. 227–234, 1997.

Waksman, et al.; "Crystal structure of the phosphotyrosine recognition domain SH2 of v–src complexed with tyrosine––phosphosrylated peptides", *Nature*, vol. 358, pp. 646–653, Aug. 20, 1992.

Waksman, et al.; "Binding of a High Affinity Phosphotyrosyl Peptide to the Src SH2 Domain: Crystal Structures of the Complexed and Peptide–free Forms", *Cell*, vol. 72, pp. 779–790, Mar. 12, 1993.

Mikol, et al., "The Crystal Structures of the SH2 Domain . . . Gated Peptide Binding Site", *Academic Press Ltd.*, pp. 344–354, 1995.

Hatada, et al.; "Molecular basis for interaction of the protein tyrosine kinase ZAP–70 with the T–cell receptor", *Nature*, vol. 377, Sep. 7, 1995.

Zhou, et al.; "Solution structure of the Shc SH2 domain complexed with a tyrosine–phosphorylated peptide from the T–cell receptor", *Proc. Natl. Acad. Sci.*, vol. 92, pp. 7784–7788, Aug. 1995.

Narula, et al.; "Solution structure of the C–terminal SH2 domain . . . phosphotyrosine pentapeptide", *Structure*, vol. 3, No. 10, pp. 1061–1073, 1995.

Xu, et al.; "Solution Structure of the Human . . . Tyrosine Pentapeptide", *Biochemistry*, vol. 34, No. 7, pp. 2107–2121, 1995.

Tong, et al.; "Crystal Structures of the . . . and 1.8Å Resolution", *J. Mol. Biology*, pp. 601–610, 1996.

Sicheri, et al.; "Crystal structure of the Src family tyrosine kinase Hck", *Nature*, vol. 385, pp. 602–609, Feb. 13, 1997.

Chen, et al.; "Crystal Structure of . . . Bound to DNA", *Cell*, vol. 93, pp. 827–839, May 29, 1998.

Songyang, et al.; "Recognition and specificity in protein tyrosine kinase–mediated signalling", *Elsevier Science Ltd.*, pp. 470–475, 1995.

Lunney, et al.; "Structure–Based Design of a . . . SH2 Domain", *J. Am. Chem. Soc.*, vol. 119, pp. 12471–12476, 1997.

Pacofsky, et al.; "Potent Dipeptide Inhibitors of the pp60$^{c-src}$ SH2 Domain", *J. Med. Chem.*, vol. 41, pp. 1894–1908, 1998.

Marseigne, et al.; "Synthesis of New . . . Tyrosine Residues", *J. Org. Chem.*, vol. 53, pp. 3621–3624, 1988.

Burke, Jr., et al.; "Preparation of Fluoro– and . . . Analogues of O–Phosphotyrosine", *J. Org. Chem.*, pp. 1336–1340, Mar. 12, 1993.

Burke, Jr., et al.; "Synthesis of 4–Phosphono . . . Peptide Analogues", *Tetrahedron Letters*, vol. 34, No. 26, pp. 4125–4128, 1993.

Smyth, et al.; "Enantioselective Synthesis . . . Analogues of O–Phosphotyrosine", *Tetrahedron Letters*, vol. 35, No. 4, pp. 551–554, 1994.

Domcheck, et al.; "Inhibition of SH2 Domain/Phosphoprotein Association by a Nonhydrolyzable Phosphonopeptide", *Biochemistry*, vol. 31, No. 41, pp. 9865–9870.

Burke et al.; "Nonhydrolyzable Phosphotyrosyl . . . SH2 Domain Inhibitors", *Biochemistry*, vol. 33, No. 21, pp. 6990–6994, 1994.

Xiao et al.; "Syp (SH–PTP2) Is . . . Signal Transduction", *The Journal of Biological Chem.*, vol. 269, No. 33, pp. 21244–21248, 1994.

Wange et al.; "F$_2$(Pmp)$_2$–TAM . . . T Cell Signaling", *Am. Soc. for Biochemistry and Molecular Biology*, vol. 270, No. 2, pp. 1–6, Jan. 13, 1995.

Rojas et al.; "Controlling Epidermal . . . EGF Receptor", *The J. of Biological Chemistry*, vol. 271, No. 44, pp. 27456–27461, Nov. 1, 1996.

Williams et al., "Selective Inhibition of . . . Grb2–binding Peptide", *The J. of Biological Chemistry*, vol. 272, No. 35, pp. 22349–22354, Aug. 29, 1997.

Stankovic et al.; "The Role of . . .Domain Ligands", *Bioorganic & Medicinal Chem. Letters*, vol. 7, No. 14, pp. 1909–1914, 1997.

Gilmer et al.; "Peptide Inhibitors . . . Interactions", *The J. of Biological Chem.*, vol. 269, No. 50, pp. 31711–31719, Dec. 16, 1994.

Mehrotra et al.; "α–Dicarbonyls As . . . Ac–TYR(OPO$_3$H$_2$)–GLU–GLU–ILE–GLU", *Bioorganic & Medicinal Chem. Letters*, vol. 6, No. 16, pp. 1941–1946, 1996.

Ye et al.; "L–O–(2–Malonyl)tyrosine: . . . Inhibitory Peptides", *J. Med. Chem.*, vol. 38, pp. 4270–4275, 1995.

Burke et al., "4'–O–[2–(2–Fluoromalonyl)]–L–tyrosine: . . . Inhibitory Peptides", *J. of Medicinal Chem.*, pp. 1021–1027, Mar. 1, 1996.

Margolis, Ben; "The GRB Family of SH2 Domain Proteins", *Prog. Giophys. Molec. Biol.*, vol. 62, pp. 223–244, 1994.

Fretz, et al.; "Targeting a Hydrophobic . . . SH2 Domain", *15$^{th}$ Amer. Peptide Symposium*, Nashville, TN, Jun. 1997, Abs. No. P422.

Burke, Jr., et al.; "Preparation of . . . Peptide Synthesis", *J. of Synthetic Organic Chem.*, No. 11, p. 1019, Nov. 11, 1991.

Burke, Jr., et al.; "Enantioselective Synthesis . . . Inhibitory Peptides", *Tetrahedron*, vol. 54, pp. 9981–9994, 1998.

Fixman, et al.; "Efficient Cellular . . . Proteins, Cb1 and Gab1", *The J. of Biological Chem.*, vol. 272, No. 32 pp. 20167–20172, Aug. 8, 1997.

Tari, et al.; "Inhibition of Grb2 . . . Leukemic Cells", *Biochemical and Biophysical Research Communications*, vol. 235, pp. 383–388, Article No. RC976791, 1997.

Xie et al., "Dominant–negative Mutants . . . Rat HER–2/Neu", *The J. of Biological Chem.*, vol. 270, No. 51, pp. 30717–30724, Dec. 22, 1995.

Maiganan et al.; "Crystal Structure of the Mammalian Grb2 Adaptor", *Science*, vol. 268, pp. 291–293, Apr. 14, 1995.

Saltiel et al., "Targeting signal transduction in the discovery of antiproliferative drugs". *Chemistry & Biology*, vol. 3, No. 11, pp. 887–893, Nov. 1996.

McNemar, et al.; "Thermodynamic and . . . Binding to Grb2–SH2", *Biochemistry*, vol. 36, pp. 10006–10014, 1997.

Ogura, et al.; "Conformation of an . . . Grb2 SH2 domain", *J. of Biomolecular NMR*, vol. 10, pp. 273–278, 1997.

Gay et al.; "Dual Specificity of . . . Peptide Ligands", *Biochemistry*, vol. 36, pp. 5712–5718, 1997.

Bobko, et al.; "CD45 Protein . . . Irreversible Inhibitors", *Bioorganic Chem. Letters*, vol. 5, No. 4, pp. 353–356, 1995.

Burke et al., "Conformationally Constrained . . . 2 Domain Inhibitors", *J. Med. Chem.*, vol. 38, pp. 1386–1396, 1995.

*Chemical Abstracts*, vol. 122, p. 424, 1995 (Abs. No. 258899).

Gordeev, et al.; "N–α–Fmoc–4–Phosphono(difluoromethyl)–L–pheny lalanine: . . . into Peptides", *Tetrahedron Letters*, vol. 35, pp. 7585–7588, 1994.

Kitas, et al.; "Synthesis of O–Phosphotyrosine . . . Deprotection Procedures", *J. Org. Chem.*, vol. 55, pp. 4181–4187, 1990.

*Chemical Abstracts*, vol. 124, No. 1, p. 1004, 1996, (Abs. No. 9413).

Schoepfer et al.; "Highly Potent Inhibitors of the Grb2–SH2 Domain", *Bioorganic & Medicinal Chemistry Letters*, vol. 9, pp. 221–226, 1999.

Tong, et al.; "Carboxymethyl–phenylalanine . . . Domain Binding", *The J. of Biological Chem.*, vol. 273, No. 32, pp. 20238–20242, Aug. 7, 1998.

Yao, et al.; "Potent Inhibition of . . . Ligands", *J. Med. Chem.*, vol. 42, pp. 25–35, 1999, Pub. on Internet Dec. 5, 1998.

Morelock et al.; "Determination of Receptor . . . Phosphotyrosyl Peptides", *J. of Med Chem.*, 38, 1309–1318.

Oligino et al., "Nonphosphorylated . . . 2 Domain", *The J. of Biological Chem.*, vol. 272, No. 46, pp. 29046–29052, Nov. 14, 1997.

Shahripour et al.; Novel Phosphotyrosine . . . Domain, *Bioorganic & Medicinal Chem. Letters*, vol. 6, No. 11, pp. 1209–1214, 1996.

Rojas et al., "An Alternative . . . SH2 Domain", *Biochemical and Biophysical Research Communications*, vol. 234, pp. 675–680, 1997.

Furet et al., "Structure–Based . . . Grb2–SH2 Domain", *J. of Medicinal Chem.*, vol. 41, No. 18, pp. 3442–3449, Mar. 16, 1998.

Miller et al., "EPSP Synthase . . . 3–Phosphate Mimics", *J. Organic & Medicinal Chem. Letters*, vol. 3, No. 7, pp. 1435–1440, 1993.

"Synthesis and . . . containing peptides", *Chem. Abs.*, vol. 123, No. 257331h, p. 1220, 1995.

* cited by examiner

OxPmp pTyr

Blot: Anti-phosphotyrosine antibody

Blot: Anti-phosphotyrosine antibody

SEQUENCE LISTING

<160> NUMBER OF SEQ ID NOS: 55

<210> SEQ ID NO 1
<211> LENGTH: 11
<212> TYPE: PRT
<213> ORGANISM: mammalian

<400> SEQUENCE: 1

Asp Glu Leu Gln Lys Asp Arg Met Ala Glu Ala
 1               5                  10

<210> SEQ ID NO 2
<211> LENGTH: 5
<212> TYPE: PRT
<213> ORGANISM: mammalian

<400> SEQUENCE: 2

Ser Glu Ile Gly Met
 1               5

```
<210> SEQ ID NO 3
<211> LENGTH: 5
<212> TYPE: PRT
<213> ORGANISM: mammalian

<400> SEQUENCE: 3

Glu Glu Ile Tyr Leu
 1               5

<210> SEQ ID NO 4
<211> LENGTH: 5
<212> TYPE: PRT
<213> ORGANISM: mammalian

<400> SEQUENCE: 4

Glu Glu Met Arg Ala
 1               5

<210> SEQ ID NO 5
<211> LENGTH: 5
<212> TYPE: PRT
<213> ORGANISM: mammalian

<400> SEQUENCE: 5

Glu Asp Met Ser His
 1               5

<210> SEQ ID NO 6
<211> LENGTH: 5
<212> TYPE: PRT
<213> ORGANISM: mammalian

<400> SEQUENCE: 6

Glu Glu Pro Asp Ser
 1               5

<210> SEQ ID NO 7
<211> LENGTH: 5
<212> TYPE: PRT
<213> ORGANISM: mammalian

<400> SEQUENCE: 7

Glu Asn Pro Glu Asp
 1               5

<210> SEQ ID NO 8
<211> LENGTH: 5
<212> TYPE: PRT
<213> ORGANISM: mammalian

<400> SEQUENCE: 8

Glu Asn Val Gln Val
 1               5

<210> SEQ ID NO 9
<211> LENGTH: 5
<212> TYPE: PRT
<213> ORGANISM: mammalian

<400> SEQUENCE: 9

Thr Asn Leu Pro Ser
 1               5
```

```
<210> SEQ ID NO 10
<211> LENGTH: 5
<212> TYPE: PRT
<213> ORGANISM: mammalian

<400> SEQUENCE: 10

Thr Asn Leu Ser Ser
  1               5

<210> SEQ ID NO 11
<211> LENGTH: 5
<212> TYPE: PRT
<213> ORGANISM: mammalian

<400> SEQUENCE: 11

Thr Asn Pro Glu Phe
  1               5

<210> SEQ ID NO 12
<211> LENGTH: 5
<212> TYPE: PRT
<213> ORGANISM: mammalian

<400> SEQUENCE: 12

Asp His Pro Asn Ile
  1               5

<210> SEQ ID NO 13
<211> LENGTH: 5
<212> TYPE: PRT
<213> ORGANISM: mammalian

<400> SEQUENCE: 13

Asp Glu Asp Asp Tyr
  1               5

<210> SEQ ID NO 14
<211> LENGTH: 5
<212> TYPE: PRT
<213> ORGANISM: mammalian

<400> SEQUENCE: 14

Ile Asn Gln Ser Val
  1               5

<210> SEQ ID NO 15
<211> LENGTH: 5
<212> TYPE: PRT
<213> ORGANISM: mammalian

<400> SEQUENCE: 15

Leu Asn Thr Val Gln
  1               5

<210> SEQ ID NO 16
<211> LENGTH: 5
<212> TYPE: PRT
<213> ORGANISM: mammalian

<400> SEQUENCE: 16

Val Asn Val Gln Asn
  1               5

<210> SEQ ID NO 17
<211> LENGTH: 5
```

```
<212> TYPE: PRT
<213> ORGANISM: mammalian

<400> SEQUENCE: 17

Val Asn Val Leu Cys
 1               5

<210> SEQ ID NO 18
<211> LENGTH: 5
<212> TYPE: PRT
<213> ORGANISM: mammalian

<400> SEQUENCE: 18

Val Asn Gln Pro Asp
 1               5

<210> SEQ ID NO 19
<211> LENGTH: 5
<212> TYPE: PRT
<213> ORGANISM: mammalian

<400> SEQUENCE: 19

Met Asn Arg Arg Arg
 1               5

<210> SEQ ID NO 20
<211> LENGTH: 5
<212> TYPE: PRT
<213> ORGANISM: mammalian

<400> SEQUENCE: 20

Met Asn Arg Gln Arg
 1               5

<210> SEQ ID NO 21
<211> LENGTH: 5
<212> TYPE: PRT
<213> ORGANISM: mammalian

<400> SEQUENCE: 21

Leu Asn Ala Asn Lys
 1               5

<210> SEQ ID NO 22
<211> LENGTH: 5
<212> TYPE: PRT
<213> ORGANISM: mammalian

<400> SEQUENCE: 22

Val Asn Ala Phe Lys
 1               5

<210> SEQ ID NO 23
<211> LENGTH: 5
<212> TYPE: PRT
<213> ORGANISM: mammalian

<400> SEQUENCE: 23

Leu Asn Ala Lys Lys
 1               5

<210> SEQ ID NO 24
<211> LENGTH: 5
<212> TYPE: PRT
<213> ORGANISM: mammalian
```

```
<400> SEQUENCE: 24

Ile Asn Ala Ser Tyr
 1               5

<210> SEQ ID NO 25
<211> LENGTH: 5
<212> TYPE: PRT
<213> ORGANISM: mammalian

<400> SEQUENCE: 25

Ile Asn Ala Ser Phe
 1               5

<210> SEQ ID NO 26
<211> LENGTH: 10
<212> TYPE: PRT
<213> ORGANISM: mammalian

<400> SEQUENCE: 26

Met Asp Met Ser Lys Asp Glu Ser Val Asp
 1               5                  10

<210> SEQ ID NO 27
<211> LENGTH: 5
<212> TYPE: PRT
<213> ORGANISM: mammalian

<400> SEQUENCE: 27

Val Pro Met Leu Asp
 1               5

<210> SEQ ID NO 28
<211> LENGTH: 12
<212> TYPE: PRT
<213> ORGANISM: mammalian

<400> SEQUENCE: 28

Ala Ala Met Gly Ala Cys Pro Ala Ser Glu Gln Gly
 1               5                  10

<210> SEQ ID NO 29
<211> LENGTH: 5
<212> TYPE: PRT
<213> ORGANISM: mammalian

<400> SEQUENCE: 29

Glu Glu Met Arg Ala
 1               5

<210> SEQ ID NO 30
<211> LENGTH: 5
<212> TYPE: PRT
<213> ORGANISM: mammalian

<400> SEQUENCE: 30

Glu Met Asn Arg Gln
 1               5

<210> SEQ ID NO 31
<211> LENGTH: 5
<212> TYPE: PRT
<213> ORGANISM: mammalian

<400> SEQUENCE: 31
```

Ala Ala Met Gly Ala
1               5

<210> SEQ ID NO 32
<211> LENGTH: 5
<212> TYPE: PRT
<213> ORGANISM: mammalian

<400> SEQUENCE: 32

Met Val Met Val Lys
1               5

<210> SEQ ID NO 33
<211> LENGTH: 5
<212> TYPE: PRT
<213> ORGANISM: mammalian

<400> SEQUENCE: 33

Met Pro Met Asn Gln
1               5

<210> SEQ ID NO 34
<211> LENGTH: 5
<212> TYPE: PRT
<213> ORGANISM: mammalian

<400> SEQUENCE: 34

Glu Tyr Met Asn Arg
1               5

<210> SEQ ID NO 35
<211> LENGTH: 5
<212> TYPE: PRT
<213> ORGANISM: mammalian

<400> SEQUENCE: 35

Glu Tyr Met Asp Val
1               5

<210> SEQ ID NO 36
<211> LENGTH: 5
<212> TYPE: PRT
<213> ORGANISM: mammalian

<400> SEQUENCE: 36

Ile Ile Pro Leu Pro
1               5

<210> SEQ ID NO 37
<211> LENGTH: 5
<212> TYPE: PRT
<213> ORGANISM: mammalian

<400> SEQUENCE: 37

Val Ala Pro Leu Thr
1               5

<210> SEQ ID NO 38
<211> LENGTH: 5
<212> TYPE: PRT
<213> ORGANISM: Artificial Sequence
<220> FEATURE:
<221> NAME/KEY: DOMAIN
<222> LOCATION: (4)..(5)
<223> OTHER INFORMATION: Xaa at 4 or 5 is any amino acid.   Analogue of human basic FGF receptor chain following Tyr766.

<400> SEQUENCE: 38

Leu Asp Leu Xaa Xaa
 1               5

<210> SEQ ID NO 39
<211> LENGTH: 5
<212> TYPE: PRT
<213> ORGANISM: mammalian

<400> SEQUENCE: 39

Leu Val Ile Gln Gly
 1               5

<210> SEQ ID NO 40
<211> LENGTH: 5
<212> TYPE: PRT
<213> ORGANISM: mammalian

<400> SEQUENCE: 40

Leu Arg Val Ala Pro
 1               5

<210> SEQ ID NO 41
<211> LENGTH: 5
<212> TYPE: PRT
<213> ORGANISM: mammalian

<400> SEQUENCE: 41

Leu Gly Leu Asp Val
 1               5

<210> SEQ ID NO 42
<211> LENGTH: 5
<212> TYPE: PRT
<213> ORGANISM: mammalian

<400> SEQUENCE: 42

Tyr Ala Val Gln Pro
 1               5

<210> SEQ ID NO 43
<211> LENGTH: 5
<212> TYPE: PRT
<213> ORGANISM: mammalian

<400> SEQUENCE: 43

Ile Ile Pro Leu Pro
 1               5

<210> SEQ ID NO 44
<211> LENGTH: 5
<212> TYPE: PRT
<213> ORGANISM: mammalian

<400> SEQUENCE: 44

Ile Gly Val Thr Tyr
 1               5

<210> SEQ ID NO 45
<211> LENGTH: 5
<212> TYPE: PRT
<213> ORGANISM: mammalian

<400> SEQUENCE: 45

Val Ile Leu Ser Phe
 1               5

<210> SEQ ID NO 46
<211> LENGTH: 5
<212> TYPE: PRT
<213> ORGANISM: mammalian

<400> SEQUENCE: 46

Val Met Pro Asp Thr
 1               5

<210> SEQ ID NO 47
<211> LENGTH: 5
<212> TYPE: PRT
<213> ORGANISM: mammalian

<400> SEQUENCE: 47

Val Ile Val Glu Tyr
 1               5

<210> SEQ ID NO 48
<211> LENGTH: 5
<212> TYPE: PRT
<213> ORGANISM: mammalian

<400> SEQUENCE: 48

Ile Pro Ile Asn Ala
 1               5

<210> SEQ ID NO 49
<211> LENGTH: 5
<212> TYPE: PRT
<213> ORGANISM: mammalian

<400> SEQUENCE: 49

Val Tyr Ile Asp Pro
 1               5

<210> SEQ ID NO 50
<211> LENGTH: 5
<212> TYPE: PRT
<213> ORGANISM: mammalian

<400> SEQUENCE: 50

Ile Ile Leu Glu Leu
 1               5

<210> SEQ ID NO 51
<211> LENGTH: 5
<212> TYPE: PRT
<213> ORGANISM: mammalian

<400> SEQUENCE: 51

Val His Val Asn Ala
 1               5

<210> SEQ ID NO 52
<211> LENGTH: 5
<212> TYPE: PRT
<213> ORGANISM: mammalian

<400> SEQUENCE: 52

-continued

```
Val Asn Val Leu Lys
 1               5

<210> SEQ ID NO 53
<211> LENGTH: 15
<212> TYPE: PRT
<213> ORGANISM: mammalian

<400> SEQUENCE: 53

Ile Asn Gln Ser Val Pro Lys Arg Pro Ala Gly Ser Val Gln Asn
 1               5                  10                  15

<210> SEQ ID NO 54
<211> LENGTH: 4
<212> TYPE: PRT
<213> ORGANISM: mammalian

<400> SEQUENCE: 54

Ile Asn Gln Ser
 1

<210> SEQ ID NO 55
<211> LENGTH: 5
<212> TYPE: PRT
<213> ORGANISM: mammalian
<300> PUBLICATION INFORMATION:
<303> JOURNAL: Biochemistry
<304> VOLUME: 36
<306> PAGES: 5712-5718
<307> DATE: 1997

<400> SEQUENCE: 55

Cys Asn Ile Tyr Cys
 1               5
```

ACYLATED OLIGOPEPTIDE DERIVATIVES HAVING CELL SIGNAL INHIBITING ACTIVITY

The present invention relates to pharmaceutically active compounds comprising a N-oxalyl peptide structure, pharmaceutical preparations comprising said compounds, the compounds for the use in the therapeutic (including propylactic) or diagnostic treatment of the animal or especially human body, and the use of said compounds for the therapeutic or diagnostic treatment of the animal or especially human body or for the manufacture of pharmaceutical preparations.

BACKGROUND OF THE INVENTION

The search for new classes of compounds for the therapy and prophylaxis of proliferative diseases, cancer and metabolic deregulation is one of the most important tasks for pharmaceutical research. These diseases affect a large portion of the population, leading to suffering and often being the cause for the death of the individuals stricken therewith.

Signal transduction is the process of relaying extracellular messages, e.g. chemical messages in the form of growth factors, hormones and neurotransmitters, via receptors, e.g. cell-surface receptors, to the interior of the cell. At the heart of this biological communication are the protein-tyrosine kinases. These enzymes, found, for example, as either transmembrane growth factor receptors or as nuclear or cytosolic non-receptor proteins, catalyze the phosphorylation of specific tyrosine residues. This class of enzymes includes, but is not limited to, the PDGF receptor, the FGF receptor, the HGF receptor, members of the EGF receptor family such as the EGF receptor, the HGF receptor, members of the EGF receptor family such as the EGF receptor, erb-B2, erb-B3 and erb-B4, the src kinase family, Fak kinase and the Jak kinase family. The tyrosine-phosphorylated proteins are involved in a range of metabolic processes, from proliferation and growth to differentiation. Protein-tyrosine phosphorylation is known to be involved in modulating the activity of some target enzymes as well as in generating specific complex networks involved in signal transduction via various proteins containing a specific amino acid sequence called a Src Homology region or SH2 domain (for review see Proc. Natl. Acad. Sci. USA 90, 5891 (1990)). A malfunction in this protein-tyrosine phosphorylation through tyrosine kinase overexpression or deregulation is manifested by various oncogenic and (hyper-)proliferative disorders such as cancer, inflammation, autoimmune disease, hyperroliferative skin disorders, such as psoriasis, and allergy/asthma.

SH2- and/or SH3-comprising proteins that play a role in cellular signaling and transformation include, but are not limited to, the following: Src, Lck, Eps, ras GTPase-activating protein (GAP), phospholipase C, phosphoinositol-3 (Pl-3)kinase, Fyn, Lyk, Fgr, Fes, ZAP-70, Sem-5, p85, SHPTP1, SHPTP2, corkscrew, Syk, Lyn, Yes, Hck, Dsrc, Tec, Atk/Bpk, Itk/Tsk, Arg, Csk, tensin, Vav, Emt, Grb2, BCR-Abl, Shc, Nck, Crk, CrkL, Syp, Blk, 113TF, 91TF, Tyk2, esecially Src, phospholipase c, phoshoinositol-3 (pl-3) kinase, Grb2, BCR-Abl, Shc, Nck, Crk and CrkL.

A direct link has been established between activated receptor kinases and Ras with the finding that the mammalian Grb2 protein, a 26 kilodalton protein comprising a single SH2 and two SH3 domains bind to proline-rich sequences present in the Sos exchange factor.

The significance of ras-regulatory proteins in human tumors is also highlighted by the critical role of GRB2 in BCR-Abl mediated oncogenesis (J. Exp. Med., 179(1), 167–175 (1994)).

Recently, DNA sequences within the chromosomal locus 17q22-qter, which harbors the GRB2 gene, were shown by comparative genomic hybridization to exhibit a high frequency of amplification both human breast cancer cell lines and tumors (Proc. Natl. Acad. Sci. USA 91, 2156–2160 (1994)).

In a study of GRB2 gene expression in human breast cancer cell lines, Northern Blot analysis also revealed that 7/19 breast cancer cell lines exhibited more than 2 fold overexpression of GRB2 MRNA relative to normal breast epithelial cells. In MCF-7, MDA-MB-361, and -453 cells, the overexpression of GRB2 MRNA was accompanied by a 10–20 fold increase in the amount of GRB2 protein (Oncogene 9, 2723 (1994)).

SH2 domains represent recognition motifs for specific tyrosine-phosphorylated peptide sequences. Short, conserved motifs, primarily 3 to 6 amino acid on the carboxy-terminal side of phosphotyrosine residue, carry the sequence-specific information for SH2-recognition. This concept has been supported by the mapping of separate sites for binding of SH2 domains from different signaling molecules on various receptors [see, e.g., Cell 69, 413 (1992); Proc. Natl. Acad. Sci. USA 89, 678 (1992); Mol. Cell. Bio. 12, 991 (1992); EMBO J. 11, 1365 (1992); EMBO J. 11, 559 (1992); EMBO J. 11, 3911 (1992): Cell 73, 321 (1993)]. Degenerate peptide libraries have also been used to predict the specifity of individual SH2 domains (src family members, Abl, Nck, Sem5, phospholipase C-γ, p85 subunit of Pl-3 kinase, and HCP (amino terminal SH2) [see Cell 72, 767 (1993); Mol. Cell. Biol. 14, 2777 (1994)]). High-resolution crystallographic analysis and nuclear magnetic resonance of the SH2 domains of Src, Lck, PLC-γ C-terminal, p85 N-terminal, Abl, Syp C-terminal have also revealed that the region on the carboxyl side of the phosphotyrosine carries the sequence-specific information for SH2 recognition. Each of these SH2 containing proteins controls a cellular pathway involved in the biological response to a growth factor. Activation of a particular pathway can thus be inhibited by designing a small molecule that specifically disrupts a phosphoprotein/SH2 domain interaction.

Src homology 2 (SH2) domains are protein motifs which recognize and bind with high affinity to phosphotyrosyl (pTyr, 1)-containing proteins. These modules serve critical roles in protein-tyrosine kinase (PTK) pathways by protein-protein oligomerization in response to specific signalling events.[1] The growth factor receptor-bound 2 (Grb2) SH2 domain is a key link in mitogenic Ras pathways, functioning as a bridging element between cell surface growth factor receptors and the Ras protein. Grb-2 mediated activation of Ras pathway is highly relevant to a number of diseases, including breast cancer, where members of the epidermal growth factor receptor (EGFR) PTK family such as erbB-2 (HER-2/neu) are frequently over-expressed.[2] Progress in the development of novel high affinity Grb2 SH2 domain ligands[3-5] is typified by 11,[6] whose design is based on binding of a larger pTyr-containing peptide to the Grb2 SH2 domain in β-bend fashion.[7] While these inhibitors take advantage of high affinity interactions with SH2 domains outside the pTyr-binding pocket, finding suitable phosphatase-resistant replacements for the pTyr residue itself has continued to be a challenge.[8] In the area of non phosphorus-containing phosphate alternatives, analogues (9) of 4,5-dideoxyshikimate-3-phosphate (8) first demonstrated the utility of the malonate group as a phosphate mimetic.[9]. Based on this work, the dicarboxylic-containing O-malonyl-L-tyrosine (OMT, 4)[10] was prepared on a non-phosphorus-containing pTyr mimetic. Although OMT residues are moderately potent against a variety of SH2 domains,[11] they share with parent pTyr the disadvantage of two negative charges. Efforts are therefore underway to identify monocarboxylic-based pTyr mimetics for use in Grb2 SH2 domain antagonists.

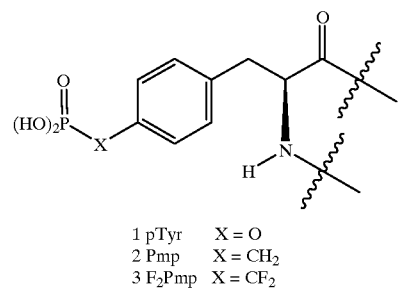

1 pTyr   X = O
2 Pmp    X = CH$_2$
3 F$_2$Pmp  X = CF$_2$

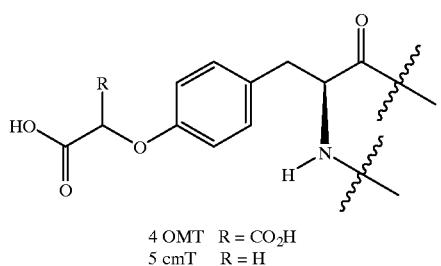

4 OMT   R = CO$_2$H
5 cmT   R = H

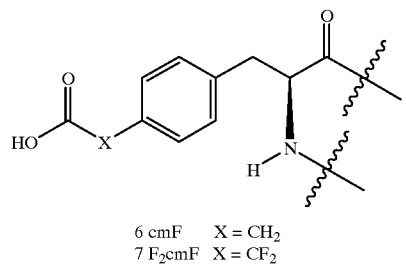

6 cmF    X = CH$_2$
7 F$_2$cmF  X = CF$_2$

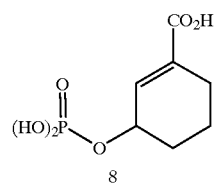

8

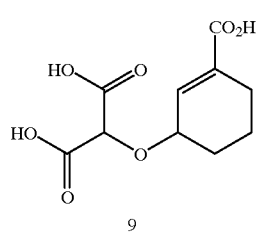

9

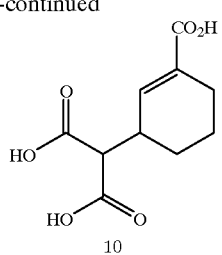

10

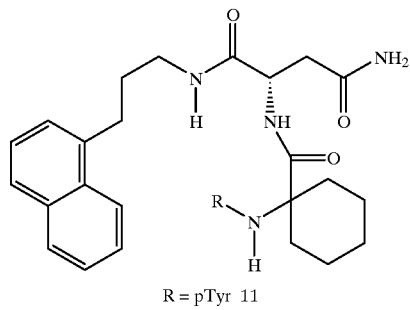

R = pTyr 11

Signal transduction is critical to normal cellular homeostasis, with abberations in some signalling pathways having potentially adverse effects, including the promotion of cancers and immune disorders. For many growth factor and cytokine pathways, binding of extracellular ligands results in intracellular signalling through the phosphorylation of tyrosyl residues by protein-tyrosine kineses (PTKs). This can result in subsequent signal transduction through protein-protein binding mediated by Src homology 2 (SH2) and phosphotyrosine binding (PTB) domains, which recognize with high affinity, specific pTyr-containing sequences.[12,13] The phosphotyrosyl pharmacophore (pTyr, 1) serves a central role by providing key recognition features necessary for assembly of these multi-component signalling complexes.[14] It has long been realized that inhibitors of abberant pTyr-dependent signalling could potentially afford new therapeutic approaches.[15] Since pTyr-dependent signalling is comprised of three distinct interacting components; (1) generation of pTyr residues by PTKs, (2) formation of protein complexes through SH2 and PTB domain-mediated pTyr-dependent processes and (3) destruction of pTyr residues by protein-tyrosine phosphatases (PTPs), inhibitors could potentially be directed at any of these three points.[16] While initial work was focused on development of PTK antagonists,[17-19] PTPs have emerged as more recent targets.[20] Both of these latter approaches rely on enzyme inhibition to achieve their effects. Alternatively, antagonizing pTyr-dependent signalling could result through the direct prevention of SH2 and PTB domain binding processes.[21,22]

Central to the binding of SH2 domains with pTyr-containing ligands is the interaction of the doubly ionized pTyr phosphate with two invariant arginine residues in a well formed pocket.[23-33] These arginine-phosphate interactions are particularly critical to the overall binding, such that high affinity binding is usually lost by removal of the phosphate group. Additional, secondary binding interactions are provided by amino acids 2–3 residues C-proximal to the pTyr residue, which introduce differential affinity toward SH2 domain sub-families.[23] Design of SH2 domain inhibitors therefore concerns itself with three thematic areas: (1) interactions within the pTyr 3 binding pocket[16] (2) interactions with recognition areas outside the pTyr pocket and (3) bridging elements between structural features (1) and (2). Examples of this type of approach have recently been reported. [35,36]

Although the pTyr pharmacophore plays a dominant role in SH2 domain.ligand interactions, pTyr residues are not suitable components of inhibitors intended for in vivo application, due to the enzymatic lability of the phosphate ester bond and to the poor cellular penetration of doubly ionized phosphate species. Design of pTyr mimetics for use in SH2 domain antagonists has therefore focused on agents which are stable to phosphatases and which offer the potential for cell membrane penetration. Phosphonate-based pTyr mimetics, such as phosphonomethyl phenylalanine (Pmp, 2)[37] and difluorophosphonomethyl phenylalanine ($F_2$Pmp, 3)[38-40] replace the tyrosyl phosphate ester bond with a methylene unit. These analogues are stable to phosphatases, retain good SH2 domain binding affinity,[16,41,42] and when administered into cells by microinjection[43] or cell permeabilization techniques[44] have been shown to exhibit effects consistent with SH2 domain inhibition. Similarly, efficacy has been shown during short term incubation of cells with pTyr-peptides containing special membrane transport sequences which deliver charged species into cells.[45,46] However, while useful for pharmacological studies, such delivery techniques do not hold promise for in vivo studies. A more traditional approach using prodrug derivatization of the phosphonate moiety has met with limited success when applied to $F_2$Pmp-containing peptides.[47] These considerations have lead to the examination of non-phosphorus containing pTyr mimetics which may offer alternatives to cell delivery.[16] [48,49] Among such analogues are O-malonyltyrosine (OMT, 4)[50] and fluoro-o-malonyltyrosine (FOMT, 5),[51] which utilize malonate or fluoromalonate groups to mimetic the tyrosyl phosphate. The present study was undertaken to examine both known pTyr mimetics such as $F_2$Pmp and Pmp as well as new pTyr mimetics, in the contex of Grb2 (growth factor receptor bound 2)[52] SH2 domain binding systems. The relevance of Grb2 to several cancers, including breast cancer, highlights the need for greater diversity in ligands which disrupt these signalling processes.

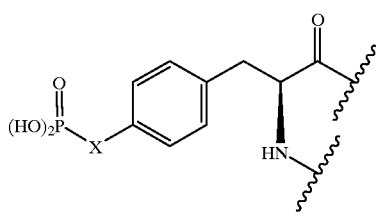

1 pTyr   X = O
2 Pmp   X = CH2
3 $F_2$Pmp   X = $CF_2$

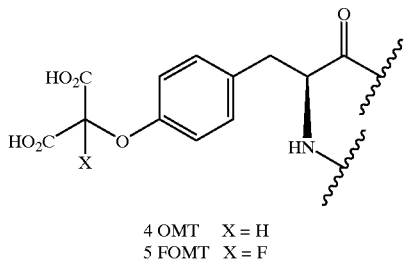

4 OMT   X = H
5 FOMT   X = F

It is a goal of the present invention to present small organic molecules that, due to their ability to mimetic the structure of the phosphotyrosine peptide binding site, have the ability to disrupt the interaction between SH2 domains of (e.g. regulatory) proteins, for example that of Grb2, and proteins with phosphorylated moieties, especially phosphorylated tyrosine moieties, for example phosphorylated protein tyrosine kinase receptors. The effect is to inhibit the associated of SH2 containing (e.g. regulatory) proteins with a protein tyrosine kinase in order to inhibit downstream signalling through one or more specifically targeted effector proteins.

SUMMARY OF THE INVENTION

Surprisingly, it has been found that the compounds of the present invention show very favorable and valuable characteristics for pharmaceutical application, especially with regard to the therapeutic (including, in a broader sense, prophylactic) and/or diagnostic treatment of diseases that depend on the downstream signal transduction pathways, especially those mediated by an interaction of a protein comprising a SH2 domain with a tyrosine phosphorylated protein, such as a phosphorylated tyrosine protein kinase; proteins comprising one or more SH2 domains that are effective in cellular signalling and transformation include, but are not limited to, the following: Src, Lck, Fps, ras GTPase-activating rotein (GAP), phosphoinositol-3) kinase, Fyn, Lyk, Fgr, Fes, ZAP-70, Sem-5, p85, SHPTP1, SHPTP2, corkscrewk Syk, Lyn, Yes, Hck, Dsrc, Tec, Atk/Bpk, Itk/Tsk, Arg, Csk, tensin, Vav, Emt, Grb2, BCR-Abl, Shc, Nck, crk, CrkL, Syp, Blk, 113TF, 91TF, tyk2, JAK1, and JAK2.

Especially, very good inhibition is already found in vitro with the compounds of formula I.

The new peptides of this invention preferably show selective inhibition of the binding of SH2-comprising proteins, such as Grb2, to phosphorylated proteins, especially activated growth factor receptor tyrosine kinases like EGF receptor tyrosine protein kinase, or Shc. The compounds of formula I disrupt the interaction between the SH2-comprising protein and the phosphoprotein, such as protein tyrosine kinase, and thus blocks the ability of the tyrosine protein kinases to initiate regulatory events depending on the SH2-comprising proteins, thus resulting in inhibition of specific downstream signal transduction pathways utilized in some hyperproliferative diseases, such as tumor diseases and psoriasis and the other diseases mentioned above and below, by uncoupling of the respective protein tyrosine kinase(s) from the respective SH2-containing effector protein.

A feature of the present invention is the positive effect of the oxalyl moiety on the inhibitory action of the compounds of the present invention on the interaction of a broad variety of phosphoproteins, especially phosphotyrosine-comprising proteins, to SH2-comprising proteins (e.g. those mentioned below in the definition of the bivalent radical —(AA)$_n$—). These oxalyl moieties are even able to allow for large sequence variability in the peptide derivatives of formula I.

BRIEF DESCRIPTION OF DRAWINGS

FIG. 3A depicts the interactions between the pTyr and the Arg67 residues. FIG. 3B depicts the binding interaction of the N$^\alpha$-oxalyl L-Pmp residue used for compound 20d. FIG. 3C depicts the binding interaction of the N$^\alpha$-oxalyl residue 23b in compound 20f.

DETAILED DESCRIPTION OF THE INVENTION

Figure 1:
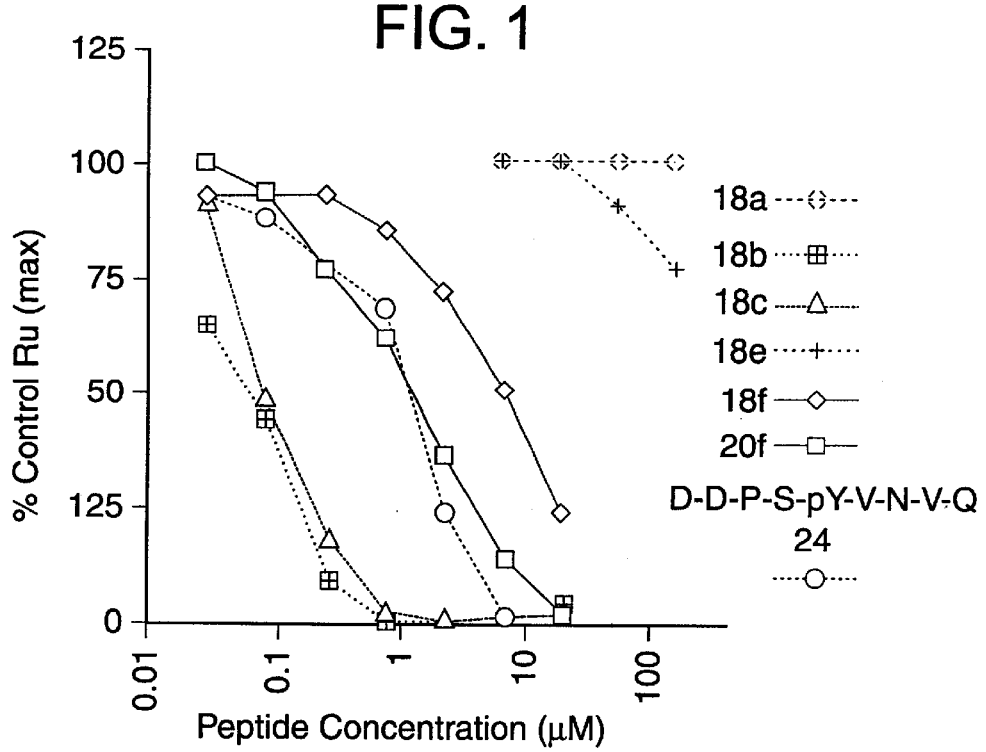
FIG. 1 depicts the Grb2 SH2 domain binding affinities, as determined by the surface plasmon resonance method, of compounds 18b, 18c, 18e, 18f, and 20f. Compound 18a is unmodified tyrosine. Compound 24 was employed as a reference.

The invention relates to an acylated peptide, namely a compound of the formula I,

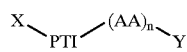
(I)

Wherein
n is 0 to 15,
X is an N$^\alpha$-oxalyl.
PTI is the bivalent radical of tyrosine or (preferably) the bivalent radical of phosphotyrosine or a phosphotyrosine mimetic.
AA stands for a bivalent radical of a natural or unnatural amino acid, and
Y is a secondary amino group, or a salt thereof.

The compounds of formula I with one or more centers of asymmetry, such as one or more asymmetric carbon atoms, may be present in the form of isomeric mixtures or pure isomers; for example, a compound of formula I with one center of asymmetry may be present in the form of a pure enantiomer or a mixture of enantiomers, e.g. a racemate, while a compound of formula I with two or more centers of asymmetry may be present in the form of a pure isomer (enantiomer) or in the form of diasteriomeric mixtures, e.g. mixtures of epimers.

A double bond in a compound of formula I may be present in the cis (Z) or trans (E) form.

In a compound of formula I with a center of asymmetry and a double bond, the respective compound may be present as a mixture of isomers or as a pure isomer.

Generally, pure isomers of compounds of formula I are preferred over isomeric mixtures.

n is preferably 1 to 15, more preferably 1 to 4, even more preferably 1 to 3 and most preferably 2 or especially 3.

PTI is the bivalent radical of tyrosine (-Tyr-) or preferably a bivalent radical of phosphotyrosine or a phosphotyrosine mimetic.

A bivalent radical of phosphotyrosine is especially (D, L), (D)- or preferably (L)-4-(O-Phosphono)-Tyr[=(O—PO$_3$H$_2$) Tyr] (bound N-terminally via the imino group resulting from the α-amino group and c-terminally via the carbonyl group resulting from its α-carboxy group), preferably the radical of the formula A

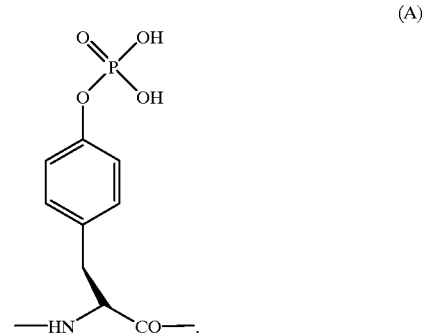
(A)

A bivalent radical of a phosphotyrosine mimetic PTI is defined as any radical that is able to replace a phosphotyrosine radical which resembles, but is structurally different from the respective phosphotyrosine radical and which cannot lose its phosphono-group too easily due to hydrolysis. Preferably, such a mimetic is selected from the respective bivalent radical (which is bound N-terminally via the imino group resulting from the α-amino group and C-terminally via the carbonyl group resulting from its α-carboxy group) of an amino acid selected from phosphonomethyl-phenylalanine, especially 4-phosphonomethyl-phenylalanine, phosphono-(α-fluoro) methyl-phenylalanine, esecially 4-phosphono-(α-fluoro) methyl-phenylalanine, phosphono-(α,α-difluoro)methyl-phenylalanine, especially 4-phosphono-(α,α-difluoro) methyl-phenylalanine, phosphono-(α-hydroxy)methyl-phenylalanine, especially 4-phosphono-(α-hydroxy)methyl-phenylalanine, O-sulfo-tyrosine, such as 4-(O-sulfo) tyrosine, dicarboxymethoxy)-phenylalanine; (less preferably) phosphonophenylalanine, such as 4-phosphonophenylalanine; aspartic acid, glutamic acid, phosphoserine and phosphothreonine, each of which is present in the (D,L)-, D- or preferably the L-form. Other mimetics include the mimetics discussed, hereinabove in the background of the invention.

For PTI, a bivalent radical of phosphotyrosine and especially a bivalent radical of phosphono-(α,α-difluoro)methyl-phenylalanine, especially 4-phosphono-(α,α-difluoro) methyl-phenylalanine or a bivalent radical of phosphonomethyl-phenylalanine, especially 4-(phosphonomethyl)-phenylalanine, is preferred as are the mimetics disclosed in the background of the invention.

AA stands for a natural or unnatural amino acid, and is preferably a bivalent radical of an α or β-amino acid which is preferably bonded N-terminally by way of its a or β-amino group and C-terminally by way of its carboxy group and is preferably selected from the group comprising a bivalent radical of a natural α-amino acid having the L-configuration, such as those normally occurring in proteins, or an epimer of such an amino acid, that is to say having the unnatural D-configuration, or a (D,L)-isomerical mixture thereof; or a homologue of such an amino acid, for example a β-amino acid or an α-amino acid wherein the amino acid side chain has been shortened by one or two methylene groups or lengthened to up to 10 carbon atoms, such as an α-amino alkanoic acid with 5 up to and including 10 carbon atoms in a linear chain, an unsubstituted or substituted aromatic (α-aryl or α-aryl lower alkyl) amino acid wherein the aryl radical has from 6 to 14 carbon atoms, for example a homophenylalanine or a substituted phenylalanine or phenylglycine wherein the phenyl maybe mono- or poly-substituted by lower alkyl, for example methyl, lower alkoxy, for example methoxy, lower alkanoyloxy, for example acetoxy, amino, lower alkylamino, for example methylamino, di-lower alkylamino, for example dimethylamino, lower alkanolyamino, for example acetylamino or pivaloylamino, lower alkoxycarbonylamino, for example tert-butoxy-carbonylamino, arylmethoxycarbonylamino wherein aryl preferably has from 6 to 14 carbon atoms, for example benzyloxycarbonylamino wherein aryl preferably has from 6 to 14 carbon atoms, for example benzyloxycarbonylamino or 9-fluorenylmethoxycarbonylamino, halogen, for example fluorine, chlorine, bromine or iodine, carboxy and/or by nitro, a benzo-fused phenylalanine or phenylglycine, such as α-naphthylalanine, and a hydrogenated phenylalanine or phenylglycine, such as cyclohexylalanine or cyclohexylglycine, or an α-amino heterocyclyl-lower alkanoic acid wherein heterocyclyl preferably is a single or double ring system having from 3 to 10 ring atoms, is bonded via a carbon atom or via a nitrogen atom and contains up to 3 further hetero atoms selected from oxygen, nitrogen, sulfur, and sulfur linked to 1 or 2 oxygen atoms, and may be unsaturated or partially or fully saturated, for example furyl, pyrrolyl, pyrrolidinyl, morpholinyl, pyridyl or indolyl, a cyclic α-amino-(α, α-lower alkylene)-carbonic acid; or an α-amino-[($C_6$–$C_8$)-bicyclo]-carbonic acid; each being present in the L-, D- or (D,L)-configuration and in unprotected or amino-, carboxy- or sulfhydryl-protected from.

Especially preferred is the bivalent radical, bonded via its α- or β-carbonyl group, of an amino acid selected from glycine (H-Gly-OH), alanine (H-Ala-OH), β-alanine (H-βAla-OH), valine (H-Val-OH), norvaline (α-aminovaleric acid), leucine (H-Leu-OH), iso-leucine (H-Ile-OH), norleucine (α-aminohexanoic acid, H-Nle-OH), α-amino-n-decanoic acid, serine (H-Ser-OH), homoserine (α-amino-γ-hydroxybutyric acid), threonine (H-Thr-OH), methionine (H-Met-OH), cysteine (H-Cys-OH), S-acetylaminomethyl-cysteine (H-Cys(Acm)-OH), proline (H-Pro-OH), trans-3- and trans-4-hydroxyproline, phenylalanine (H-Phe-OH), tyrosine (H-Tyr-OH), 4-aminophenylalanine, 4-nitrophenylalanine, 4-chlorophenylalanine, 4-carboxyphenylalanine, β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), indoline-2-carboxylic acid, 1,2,3,4-tetrahydroisoquinoline-3-carboxylic acid, aspartic acid (H-Asp-OH), asparagine (H-Asn-OH, aminomalonic acid, aminomalonic acid amonoamide, glutamic acid (H-Glu-OH), glutamine (H-Gln-)H), histidine (H-His-OH), arginine (H-Arg-OH), lysine (H-Lys-OH), N'-benzyl-N'-methyl-lysine, N',N'-dibenzyl-lysine, δ-hydroxy-lysine, ornithine (α,δ-diaminovaleric acid), α-amino-cyclopentane carboxylic acid (H-$Ac_5$c-OH), α-amino-cyclohexane carboxylic acid (H-$Ac_6$c-OH), α-amino cycloheptane carboxylic acid (H-$AC_7$c-OH), α-(2-amino-2-norbornane)-carboxylic acid (H-Nbo-OH), α,γ-diamonobutyric acid and α,β-diamonopropionic acid; or (alternatively or in addition to the group of moieties mentioned just before) homophenylalanine (H-Hh-OH)=2-amino-4-phenyl-butyric acid) and a α-tert-butylglycine (H-Tle-OH)=tert-leucine); it being possible for each of the mentioned amino acids (with the exception of glycine or any other amino acid without asymmetric carbon atom) to be in the D-, L- or D,L)-form, preferably in the L- or in the D-form, H-DHph-OH is D-homophenylalanine.

More preferably, the bivalent radical —$(AA)_n$— in formula I is an analogue of an SH2 domain binding site of a protein with phosphotyrosine of a mammal, especially a human, for example one of the binding sites mentioned in Songyang et. Al., Cell 72, 767–778 (1993), e.g. (i) in the case of the Src family SH2 binding proteins, especially an analogue of the human CD3 ζ chain following Tyr 110 (that is, -Asb-Glu-Leu-Gin-Lys-Asp-Arg-Met-Ala-Glu-Ala-) or Tye 122 (that is, -Ser-Glu-Ile-Gly-Met-), an alaogue of the human Rb-associated rb 110 chain following Tyr 321 (that is, -Glu-Glu-Ile-Tyr-Leu-), an analogue of the human vav oncogene chain following Tyr 1270 (that is, -Glu-Glu-Met-Arg-Ala-), an analogue of the human ErbB3 chain following Tyr 1270 (that is, -Glu-Glu-Met-Arg-Ala-), an analogue of the human T cell CD7 chain following Tyr 222 (that is, Glu-Asp-Met-Ser-His-), (ii) in the case of the Abl SH2 binding proteins, especially an analogue of the human B cell CH 19 chain following Tyr 409 (that is, -Glu-Glu-Pro-Asp-Ser-) or Tyr 439 (that is, -Glu-Asn-Pro-Glu-Asp-), an analogue of the human B cell CD 72 chain following Tyr 39 (that is, -Glu-Asn-Val-Gln-Val-), an analogue of the human colony-stimulating factor 1 receptor chain following Tyr 923 (that is, -Thr-Asn-Leu-Pro-Ser-), an analogue of the human JunB chain following Tyr 182 (that is, -Thr-Asn-Leu-Ser-Ser-), an analogue of the human protein kinase C β-1 chain following Tyr 662 (that is, -Thr-Asn-Pro-Glu-Phe-), (iii) in the case of Crk SH2 binding proteins, especially an analogue of the human Fer tyrosine kinase chain following Tyr 615 (that is, -Asp-His-Pro-Asn-Ile-), (iv) in the case of Nck SH2 binding proteins, especially an analogue of the human cell cycle gene 1 protein chain following Tyr 139 (that is, -Asp-Glu-Asp-Asp-Tyr-), (v) in the case of Sem-5/Grb2 SH2 binding proteins, especially an analogue of the human EGF receptor chain following Tyr 1092 (that is, -Ile-Asn-Gln-Ser-Val-), an analogue of the human EGF receptor chain following Tyr 1138 (that is, -Leu-Asn-Thr-Val-Gln-), an analogue of the human SHC chain following Tyr 317 (that is, -Val-Asn-Val-Gln-Asn), an analogue of the human HGF receptor chain following Tyr 1374 (that is, -Val-Asn-Val-Leu-Cys-), an analogue of the human ErbB2 chain following Tyr 1139 (that is, -Val-Asn-Gln-Pro-Asp-), an analogue of the human ErbB3 chain following Tyr 1200 (that is, -Met-Asn-Arg-Arg-Arg-) or Tyr 1262 (that is, -Met-Asn-Arg-Gln-Arg-), an analogue of the human IGF-1 receptor chain following Tyr 1125 (that is, -Leu-Asn-Ala-Asn-Lys-), an analogue of the human Fit tyrosine kinase chain following Tyr 1213 (that is, -Val-Asn-Ala-Phe-Lys-), an analogue of the human insulin receptor chain following Tyr 1149 (that is, -Leu-Asn-Ala-Lys-Lys-), an analogue of the human CD45 PTPase chain following Tyr 706 (that is, -Ile-Asn-Ala-Ser- Tyr-), or Tyr 1015 (that is, -Ile-Asn-Ala-Ser-Phe-), (vi) in the case of p85 N-terminal SH2, especially ana analogue of the human PDGF receptor β chain following Tyr 740 (that is,-Met-Asp-Met-Ser-Lys-Asp-Glu-Ser-Val-Asp-) or tyr 751 (that is, -Val-Pro-Met-Leu-Asp-), an analogue of the human c-Kit chain following Tyr 721 (that is, -Val-Pro-Met-Leu-Asp-), an analogue of the human ErbB3 chain following Tyr 1257 (that is, -Ala-Ala-Met-Gly-Ala-Cyst-Pro-Ala-Ser-Glu-Gln-Gly-), Tyr 1270 (that is, -Glu-Glu-Met-Arg-Ala-), tyr 1241 (that is, -Glu-Met-Asn-Arg-Gln-), Tyr 1257 (that is, -Ala-Ala-Met-Gly-Ala-), Tyr 922 (that is, -Met-Val-Met-Val-Lys-), Tyr 1035 (that is, -Met-Pro-Met-Asn-Gln-), Tyr 1,178 (that is, -Glu-Tyr-Met-Asn-Arg-), or tye 1203 (-Glu-Tyr-Met-Asp-Val-), (vii) in the case of PLC-γ C-terminal SH2, especially an analogue of the human PDGF receptor β chain following Tyr 1021 (that is, -Ile-Ile-Pro-Leu-Pro-), an analogue of the human PDGF α chain following Tyr 1018 (that is, -Ile-Ile-Pro-Leu-Pro-), an analogue of the human ErbB2 chain following Tyr 1127 (that is, -val-Ala-Pro-Leu-Thr-), (viii) in the case of PLC-γ N-terminal SH2 binding proteins, especially an analogue of the human basic FGF receptor I, II, II, IV chain following -Tyr 766 (that is, -Leu-Asp-Leu-X-X-), an analogue of the human EGF receptor chain following Tyr 978 (that is, -Leu-Val-Ile-Gln-Gly-) or Tyr 1197 (that is, -Leu-Arg-Val-Ala-Pro-), an analogue of the human ErbB2 chain following Tyr 11248 (that is, -Leu-Gly-Leu-Asp-Val-), and (ix) in the case of SHPTP2 N-terminal SH2 binding proteins, especially an analogue of the human PDGF receptor β chain following Tyr 1009 (that is, -Thr-Ala-Val-Gln-Pro-) or Tyr 1021 (that is, -Ile-Ile-Pro-Leu-Pro-), an analogue of the human PDGF receptor 2 chain following Tyr 1018 (that is, -Ile-Ile-Pro-Leu-Pro-), Tyr 988 (that is, -Ile-Gly-Val-Thr-Tyr-) or Tyr 720 (that is, -Val-Ile-Leu-Ser-Phe-), an analogue of the human ErbB3 chain following Tyr 1159 (that is, -Val-Met-Pro-Asp-Thr-) or Tyr 471 (that is, -Val-Ile-Val-Glu-Tyr-) an analogue of the human Flt receptor type tyrosine kinase chain following Tyr 1169 (that is, Ile-Pro-Ile-Asn-Ala-), an analogue of the human Kit receptor type tyrosine kinase chain following Tyr 568 (that is, -Val-Tyr-Ile-Asp-Pro-), an analogue of the human Ros receptor type tyrosine kinase chain following Tyr 234 (that is, -Ile-Ile-Leu-Glu-Leu-), an analogue of the human HGF receptor (Met) chain following Tyr 1367 (that is, -Val-His-Val-Asn-Ala-) or Tyr 1374 (that is, -Val-Asn-Val-Leu-Cys-); and (x) most especially an analogue of the Epidermal Growth Factor Receptor (EGFR) sequence following Tyr 1068, the binding site for Grb2 SH2 (see Buday et al., Cell 73, 611–620 (1993)), that is the sequence Ile-Asn-Gln-Ser-Val-Pro-Lys-Arg Pro-Ala-Gly-Ser-Val-Gln-Asn, preferably -Ile-Asn-Gln-Ser-; wherein in each case one or more amino acids are replaced by analogues which still allow for binding to the respective SH2 comprising protein, especially Grb2, or 1 or more amino acids are deleted, preferably 1 or more amino acids of the sequence -Ile-Asn-Gln-Ser-, more preferably 1, 2 or up to 3 amino acids of the sequence -Ile-Asn-Gln- being deleted. Preferably, the -Asn- in position 2 of the mentioned sequence following Tyr 1068 in EGFR is present as such, while the amino acids in the other positions may be replaced with one of the other amino acids mentioned above or (as far as the C-terminal amino acid(s) following the Asn are concerned) may be deleted.

More preferably, —(AA)n— has one of the following meanings:

A bivalent radical of a tripeptide of the formula -(AA$^1$)-(AA$^2$)-(AA$^3$)- wherein -(AA$^1$)- is preferably selected from -Ile-, -Ac$_5$C-, -Ac$_6$c-, -Asp-, -Gly- and -Phe- or (alternatively or in addition to the group of moieties mentioned just before) from -Ac$_7$c-, -Nbo-, -Met-, -Pro-, βAla-, -Gln-, -Glu-, -DHph-, -HPh- and -tLe-, most preferably -Ile-, -Ac$_5$c-, -Ac$_6$c-, -Asp- or -Gly- or (alternatively or in addition to the group of moieties mentioned just before) Ac$_7$c-, -Nbo- and -Gln-; -(AA$^2$)- is preferably selected from -Asn-, and also from, -βAla- and -Gly-, or (alternatively or in addition to the group of moieties mentioned just before), from -Ile-, -βAla- and Gln; most preferably -Asn-; and -(AA$^3$)- is preferably selected from -Val-, and -,β-Ala, and also from -Gly-, -Gln-, -Val-, -Asp- and -Ac$_5$c-; or, less preferably;

a bivalent radical of a dipeptide of the formula -(AA$^1$)-(AA$^2$)- wherein -(AA$^1$)- and -(AA$^2$)preferably have the meanings given above, preferably -(AA$^1$)- being -Ile- or -Ac$_6$c-, or (alternatively or in addition to the group of moieties mentioned just before) -Ac$_7$c-, -Nbo- and -Gln-; and -(AA$^2$)- being -Asn- (preferred) or also -,βAla-; or (even less preferably simply a bivalent radical of an amino acid selected from the amino acids mentioned above, especially -Ile- or (alternatively or n addition to the group of moieties mentioned just before) -Ac$_6$C-, -Nbo- and Ac$_5$c-.

A secondary amino group Y is preferably a mono amino group the substitutents of which are preferably selected from the group comprising lower alkyl, such as methyl, ethyl; isobutyl or 3-methylbutyl; octyl, such as 2-ethyl-hexyl; aryloxy-lower alkyl, especially halonaphthyloxy-lower alkyl, such as 2-(1-bromon-naphthalen-2-yloxy)-ethyl, or naphthyloxy-lower alkyl, such as 2-(naphthalen-2-yloxy or naphthalen-1-yloxy)-ethyl; aryl-lower alkyl, such as phenyl-lower alkyl, e.g. benzyl, 2-phenylpropyl, di-phenyl-lower alkyl, such as 2,2-diphenyl-ethyl or 3,3-diphenyl-propyl, (mono- or di-halophenyl)-lower alkyl, such as 2-(4-chlorophenyl)ethyl or 3-(2,4-dichlorophenyl)-propyl, naphthalenyl-lower alkyl, such as 3-naphthtalen-1-ylpropyl or 3-naphthalen-2-ylpropyl, hydroxy-naphthalenyl-lower alkyl, such as 3-(2-hydroxy-naphthalen-1-yl)-propyl, or phenanthrenyl-lower alkyl, such as 3-phenanthren-9-yl-propyl; heterocyclyl-lower alkyl, such as pyrrolidinyl-lower alkyl, e.g. 2-(1-pyrrolidinyl)-ethyl, pyridyl-lower alkyl, e.g. 2-(2-pyridyl)-ethyl, furyl-lower alkyl, e.g. 2-furylmethyl, morpholinyl-lower alkyl, e.g. 2-(4-morpholinyl)-ethyl, and indolyl-lower alkyl, e.g. 2-(3-indolyl)-ethyl; cycloalkyl, such as cyclohexyl; and cycloalkyl-lower alkyl, such as cyclohexylmethyl.

In one preferred aspect of the invention, Y is a mono substituted amino group the substitutents of which are preferably selected from the group comprising lower alkyl, e.g. methyl or ethyl, aryl-lower alkyl.

Preferably, Y is a secondary amino group as defined above, most preferably monosubstituted amino selected from lower alkylamino, such as methylamino, ethylamino; isobutylamino or 3-methylbutylamino; octylamino, such as 2-ethylhexyl amino; aryloxy-lower alkylamino, especially halonaphthyloxy-lower alkylamino, such as 2-(1-bromo-naphthalen-2-yloxy)-ethylamino, or naphthyloxy-lower alkylamino, such as 2(naphthalen-2-yloxy or naphthalen-1-yloxy)-ethylamino; aryl-lower alkylamino, such as phenyl-lower alkylamino, e.g. benzylamino, 3-phenylpropylamino, di-phenyl-lower alkylamino, such as 2,2-diphenyl-ethylamino or 3,3-diphenyl-propylamino, (mono- or di-halophenyl)-lower alkylamino, such as 2-(4-chlorophenyl)ethylamino or 3-(2,4-dichlorophenyl)propylamino, naphthalenyl-lower alkylamino, such as 3-naphthtalen-1-ylpropylamino or 3-naphthalen-2- ylpropylamino, hydroxy-naphthalenyl-lower alkylamino, such as 3-(2-hydroxy-naphthalen-1-yl)-propylamino, or phenanthrenyl-lower alkylamino, such as 3-phenanthren-9-ylpropylamino; cycloalkylamino, such as cyclohexylamino; and cycloalkyl-lower alkylamino, such as cyclohexylmethylamino.

Salts of compounds of formula I are especially acid addition salts, salts with bases or, where several salt-forming groups are present, can also be mixed salts or internal salts.

Salts are especially pharmaceutically acceptable salts of compounds of formula I.

Such salts are formed, for example, from compounds of formula I having an acid group, for example a carboxy group, a sulfo group, or a phosphoryl group substituted by one or two hydroxy groups, and are, for example, salts thereof with suitable bases, such as non-toxic metal salts derived from metals of groups Ia, Ib, IIa and IIb of the Periodic Table of the Elements, especially suitable alkali metal salts, for example lithium, sodium or potassium salts, or alkaline earth metal salts, for example magnesium or calcium salts, also zinc salts or ammonium salts, as well as salts formed with organic amines, such as unsubstituted or hydroxy-substituted mono-, di or tri-alkylamines, especially mono-, di- or tri-lower alkyl-amines, or with quaternary ammonium compounds, for example with N-methyl-N-ethyl-amine, diethylamine, triethylamine, mono-, bis- or tris-(2-hydroxy-lower alkyl)amines, such as mono-, bis- or tris-(2-hydroxyethyl)amine, 2-hydroxy-tert-butylamine or tris(hydroxy-methyl)methylamine, N,N-di-lower alkyl-N-(hydroxy-lower alkyl)-amines, such as N,N-dimethyl-N-(2-hydroxyethyl)-amine or tri-(2-hydroxyethyl)-amine, or N-methyl-D-gulcamine or quaternary ammonium salts, such as tetrabutylammonium salts. The compounds of formula I having a basic group, for example an amino group, can form acid addition salts, for example with inorganic acids, for example hydorhalic acids, such as hydrochloric acid, sulfuric acid or phosphoric acid, or with organic carboxylic, sulfonic, sulfo or phospho acids or N-substituted sulfamic acids, for example acetic acid, propionic acid, glycolic acid, succinic acid, maleic acid, hydorxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, as well as with amino acids, for example the α-amino acids mentioned hereinbefore, especially glutamic acid and aspartic acid, and with methanesulfonic acid, ethanesulfonic acid, 2-hydroxyethanesulfonic acid, ethane-1, 2-disulfonic acid, benzenesulfonic acid, 4-methylbenzene-sulfonic acid, naphthalene-2-sulfonic acid, 2- or 3-phosphoglycerate, glucose-6-phosphate, N-cyclohexyl-sulfamic acid (forming cyclamates) or with other acidic organic compounds, such as ascorbic acid. Compounds of formula I having acid and basic groups can also form internal salts.

For isolation or purification purposes, it is also possible to use pharmaceutically inacceptable salts, for example a perchlorate or picolinate salt.

The compounds of the invention have useful, in particular pharmacologically useful, properties. Surprisingly, it has been found that the compounds of formula I are able to inhibit the interaction between SH2 domains of downstream regulatory proteins, such as Grb2, and phosphoproteins, especially phosphorylated protein tyrosine kinases, such as a phosphoprotein containing a -Tyr(PO$_3$H$_2$)-X-Asn- motif, preferably phosphorylated EGFR protein tyrosine kinase (EGFR=Epidermal Growth Factor Receptor) or modified derivatives thereof, but in a broader sense also other phospho-proteins such as SHC or modified derivatives thereof, in a favourable way. They are thus useful in the treatment or prevention of diseases that respond to such inhibition.

The compounds of the invention, due to their ability to uncouple a phosphorylated protein, especially a protein tyrosine kinase, e.g. EGF receptor, from a respective SH2 containing protein, e.g. the SH2-containing Grb2, are able to inhibit subsequent cellular signal transduction pathways important for diseases such as viral, inflammatory, allergic, autoimmune, cardiovascular and especially proliferative diseases, such as for malignant hyperproliferative diseases, e.g. tumor diseases, preferably breast cancer, chronic myelogenous leukemia (CML), thyroid carcinoma and osteosarcoma, or for hyperproliferation of epithelial cells, e.g. psoriasis, are appropriate for the treatment and prophylaxis of said diseases.

Therefore, the compounds of the present invention are useful for the treatment of diseases that respond to inhibition of the interaction of (a) proteins(s) comprising (an) SH2 domain(s) and a phosphoprotein, preferably a protein tyrosine kinase or a modified version thereof, more preferably of Grb2 SH2 with EGFR or modified derivatives thereof. The term "modified version" or "modified derivative" means mainly a derivative that is causative or active in the establishment of diseases, e.g. truncated versions, virus derived analogues, etc.

The treatment can also, e.g. in the case of hematopoietic cell proliferative disorders, such as leukemias, be used in conjunction with autologous bone marrow transplantation and chemotherapy techniques. For example, an aliquot of bone marrow cells (even one cell or some single cells, which can be treated by microinjection of a compound of formula I as described above) are obtained from a patient, e.g. from the pelvis. The cells are then cultured in the presence of a compound of formula I (which may also be applied by microinjection) which is able to disrupt the protein tyrosine kinase/SH2-comprising protein-interaction. Thus blocking the signal transduction pathway of those bone marrow cells capable of forming complexes resulting from such interaction, it is possible to select against the presence of clonal daughter cells derived from these cells and to purge the culture(s) of these cells from those responsible for the hematopoietic cell proliferative disorder being treated. After chemotherapeutic and/or radiotherapeutic treatment of the patient from whom the cells have been obtained, the patient can receive an autologous infusion of cultured bone marrow cells resulting from the above purging procedure.

Due to their high binding affinity to SH2 domains, such as those of Grb2, the compounds of formula I can also be bound covalently to chromatographic materials, thus making it possible to produce chromatographic materials for the affinity purification of natural or recombinant SH2-domains or SH2-comprising proteins from the cells of living organisms. for example, a compound of formula I with an appropriate free functional group (e.g. —NH$_2$, —SH, —OH and/or —COOH) can be attached covalently to activated or activatable matrices appropriate for chromatography, e.g. cyanogen bromide activated matrices, epoxy-activated matrices, nitrophenyl chloroformate and N-hydroxysuccinimde chloroformate. Polyacrylhydrazido agarose, oxirane acrylic beads, bromoacetyl-cellulose, epichlorohydrin-activated matrices, tresyl-chloride-activated agarose, vinylsulfone-activated agarose, and the like. Preferred activated or activatable coupling gels for affinity chromatography include but are not limited to a) for coupling of compounds of formula I with an —NH$_2$ group employed for binding: cyanogen bromide activated Sepharose 4B, ECH Sepharose 4B (carbodiimide coupling method used most often in analogy to process for preparation of compounds of formula I as described below); or activated CH Sepharose 4B;

b) for coupling of compounds of formula I with an —NH$_2$ and/or an —SH group: Tresyl-activated Sepharose 4B;

c) for coupling of compounds of formula I with an —NH$_2$, —OH and/or —SH group: epoxy-activated Sepharose 6B; and d) for coupling of compounds of formula I with a —COOH group: EAH Sepharose 4B (carbodiimide method for coupling most often used in analogy to process for preparation of compounds of formula I as described below).

Sepharose stands for agarose derived chromatographic materials and is a trademark from Pharmacia, Uppsala, Sweden, from where the mentioned gels are available.

In the following definitions of preferred compounds, general terms may be replaced by their more specific (more preferred) definitions as given above in order to obtain more preferred compounds.

One preferred embodiment of the invention relates to a compound of formula I, wherein n is 1 to 15, X is oxalyl PTI is the bivalent radical of phosphotyrosine or a phosphotyrosine mimetic, AA stands for a bivalent radical of a natural or unnatural amino acid, and Y is a secondary amino group, or a salt thereof if at least one salt-forming group is present.

Preferred is a compound of formula I wherein n is 1 to 4, more preferably 1 to 3, most preferably 2 or especially 3;

X is oxalyl

PTI is a bivalent radical of tyrosine or (preferably) a bivalent radical of phosphotyrosine (in the D-, L- or less preferably the (D,L)-form) or of a phosphotyrosine mimetic in the form of a bivalent radical (which is bound N-terminally via the imino group resulting from the α-amino group and C-terminally via the carbonyl group resulting from its α-carboxy group) of an amino acid selected from phosphonomethyl-phenylalanine, especially 4-phosphono-methylphenylalanine, phosphono-(α-fluoro)methyl-phenylalanine, especially 4-phosphono-(a-fluoro)methyl-phenylalanine, phosphono-(α,α-fluoro)methyl-phenylalanine, especially 4 phosphono-(α,α-difluoro)methyl-phenylfalanine, phosphono-(α-hydroxy)methyl-phenyl- alanine, especially 4-phosphono-(α-hydroxy) methyl-phenylalanine, O-sulfo-tyrosine, such as 4-(O-sulfo)tyrosine, dicarboxymethoxy-phenylalanine (=(HOOC)$_2$—CH$_2$—O-phenylalanine, especially 4-(dicarboxymethoxy)-phenylalanine aspartic acid, glutamic acid, phosphoserine and phosphothreonine, each of which is present in the (D,L)-, D- or preferably the L-form or the mimetic mentioned in the background to the invention; —(AA)$_n$— has one of the following meanings:

A bivalent radical of a tripeptide of the formula -(AA$^1$)-(AA$^2$)-(AA$^3$)- wherein -(AA$^1$)- is preferably selected from -Ile-, -Ac$_5$c-, Ac$_6$c-, -Asp-, -Gly- and -Phe- or (alternatively or in addition to the group of moieties mentioned just before) from -Ac$_7$c0, -Nbo-, -Met-, -Pro-, -βAla-, -Gln-, -Glu-, -DHph-, -HPh- and -tLe-, most preferably -Ile-, -Ac$_5$c-, -Ac$_6$c-, -Asp- or -Gly- or (alternatively or in addition to the group of moieties mentioned just before) -Ac$_7$c-, -Nbo- and -Gln-; -(AA$^2$)- is preferably selected from -Asn-, and also from -βAla- and -Gly-, or (alternatively or in addition to the group of moieties mentioned just before), from -Ile-, -βAla- and Gln; most preferably -Asn-; and -(AA$^3$)- is preferably selected from -Val-, and -β-Ala, and also from -Gly-, -Gln-, -Val-, -Asp- and -Ac$_5$c-; or, less preferably, A bivalent radical of a dipeptide of the formula -(AA$^1$)-(AA$^2$)- wherein -(AA$^1$)- and -(AA$^2$)- preferably have the meanings given above, preferably -(AA$^1$)- being -Ile- or Ac$_6$c-, or (alternatively or in addition to the group of moieties mentioned just before) -Ac$_7$c-, -Nbo- and -Gln-; and -(AA$^2$)- being -Asn- (preferred or also -βAla-;

or (even less preferably) simply a bivalent radical of an amino acid selected from the amino acids mentioned above, especially -Ile- or (alternatively or in addition to the group of moieties mentioned just before) -Ac$_5$c, -Nbo- and Ac$_5$c-; and Y is monosubstituted amino selected from lower alkylamino, such as methylamino, ethylamino; isobutylamino or 3-methylbutylamino; octylamino, such as 2-ethyl-hexyl-amino; aryloxy-lower alkylamino, especially halonaphthyloxy-lower alkylamino, such as 2-(l-bromo-naphthalen-w-yloxy)-ethylamino, or naphthyloxy-lower alkylamino, such as 2-(naphthalen-2-yloxy or naphthalen-1-yloxy)-ethylamino; aryl-lower alkylamino, such as phenyl-lower alkylamino, e.g. benzylamino, 3-phenylpropylamino, di-phenyl-lower alkylamino, such as 2,2-diphenyl-ethylamino or 3,3-diphenyl-propylamino, (mono- or di-halophenyl)-lower alkylamino, such as 2-(4-chlorophenyl) ethylamino or 3-(2,4-dichlorophenyl)-propylamino, napthalenyl-lower alkylamino, such as 3-naphthtalen-1-ylpropylamino or 3-naphthalen-2-ylpropylamino, hydroxy-napththalenyl-lower lakylamino, such as 3-(2-hydroxynaphthalen-1-yl)-propylamino, or phenanthrenyl-lower alkylamino, such as 3-phenanthren-9-ylpropylamino; cycloalkylamino, such as cyclohexylamino; and cycloalkyl-lower alkylamino, such as cyclohexylethylamino;

or a salt thereof at least one salt-forming group is present.

Preferred is also a compound of formula I wherein n is 1 to 4, more preferably 1 to 3, most preferably 2 or especially 3;

X is oxalyl

PTI is a bivalent radical of phosphotyrosine (in the D-, L- or less preferably the (D,L)-form) or of a phosphotyrosine mimetic in the form of a bivalent radical (which is bound N-terminally via the imino group resulting from the α-carboxy group) (of an amino acid selected from phosphonomethyl-phenylalanine, especially 4-phosphonomethyl-phenylalanine, phosphono-(α-α-difluoro)methyl-phenylalanine, especially 4-phosphono-(α-α-difluoro) methyl-phenylalanine, phosphono-(α-hydroxy)methyl-phenylalanine, especially 4-phosphono-(α-hydroxy)methyl-phenylalanine, O-sulfo-tyrosine, such as 4-(O-sulfo)tyrosine, dicarboxymethoxy-phenylalanine (=(HOOC)$_2$—CH$_2$—O-phenylalanine, especially 4-(dicarboxymethoxy)-phenylalanine aspartic acid, glutamic acid, phosphoserine and phosphothreonine, each of which is present in the (D,L)-, D- or preferably the L-form or the mimetics mentioned in the background of the invention;

—(AA)$_n$— has one of the following meanings:
A bivalent radical of a tripeptide of the formula -(AA$^1$)-(AA$^2$)-(AA$^3$)- wherein -(AA$^1$)- is preferably selected from -Ile, -Ac$_5$c-, Ac$_6$c-, -Asp-, -Gly- and -Phe, most preferably -Ile-, -Ac$_5$c-, -Ac$_6$c-, -Asp- or -Gly-; -(AA$^2$)- is preferably selected from -Asn-, and also from -βAla- and -Gly-, most preferably -Asn-; and -(AA$^3$)- is preferably selected from -Val-, and -β-Ala, and also from -Gly-, -Gln-, -Val-, -Asp- and -Ac$_5$c-;
a bivalent radical of a dipeptide of the formula -(AA$^1$)-(AA$^2$)- wherein -(AA$^1$)- and -(AA$^2$)- preferably have the meanings given above, preferably -(AA$^1$)- being -Ile- or Ac$_6$c- and -(AA$^2$)- being -Asn- (preferred) or also -βAla-;
or (less preferably) simply a bivalent radical of an amino acid selected from the amino acids mentioned above, especially -Ile-; and Y is a mono substituted amino group the substitutents of which are preferably selected from the group comprising lower alkyl, e.g. methyl or ethyl, phenyl-lower alkyl, e.g. benzyl, naphthalenyl-lower alkyl, e.g. naphthalenyl propylamino or a salt thereof.

Preferred is also a compound of formula I wherein n is 1 to 4, more preferably 1 to 3, most preferably 2 or especially 3;

X is oxalyl

PTI is a bivalent radical of tyrosine or (preferably) a bivalent radical of phosphotyrosine (in the D-, L- or less preferably the (D,L)-form) or of a phosphotyrosine mimetic in the form of a bivalent radical (which is bound N-terminally via the imino group resulting from the α-amino group and C-terminally via the carbonyl group resulting from its α-carboxy group) of an amino acid selected from phosphonomethyl-phenylalanine, especially 4-hosphono-methyl-phenylalanine, phosphono-(α-fluoro)methyl-phenylalanine, especially 4-phosphono-(α-fluoro)methyl-phenylalanine, phosphono-(α-,α-adifluoro)methyl-phenylalanine, especially 4-phosphono-(α-α-difluro)methyl-phenylalanine, phosphono-(α-hydroxy)methyl-phenylalanine, especially 4-phosphono-(α-hydroxy)methyl-phenylalanine, O-sulfo-tyrosine, such as 4-(O-sulfo)tyrosine, dicarboxymethoxy-phenylalanine (—(HOOC)$_2$—CH$_2$—O-phenylalanine, especially 4-(dicarboxymethoxy-phenylalanine aspartic acid, glutamic acid, phosphoserine and phosphothreonine, each of which is present in the (D,L)-, D- or preferably the L-form or the mimetics mentioned hereinabove in the background of the invention;

—(AA)$_n$— has one of the following meanings:
A bivalent radical of a tripeptide of the formula -(AA$^1$)-(AA$^2$)-(AA$^3$)- wherein -(AA$^1$)- is preferably selected from -Ile-, Ac$_5$c-, -Ac$_6$c-, -Asp-, -Gly- and -Phe- or (alternatively or in addition to the group of moieties mentioned just before) from -Ac$_7$c-, -Nbo-, -Met-, -Pro-, -βAla-, -Gln-, -Glu-, -DHph-, -HPh- and -tLe-, most preferably -Ile-, -Ac$_5$c-, -Ac$_6$c-, -Asp- or -Gly- or (alternatively or in addition to the group of moieties mentioned just before) -Ac$_7$c-, -Nbo- and -Gln-; -(AA$^2$)- is preferably selected from -Asn-, and also from -βAla- and -Gly-, or (alternatively or in addition to the group of moieties mentioned just before), from -Ile-, -βAla- and Gln; most preferably -Asn-; and -(AA$^3$)- is preferably selected from -Val-, and -β-ala, and also from -Gly-, -Gln-, -Val-, -Asp- and -Ac$_5$c-; or, less preferably, a bivalent radical of a dipeptide of the formula -(AA$^1$)-(AA$^2$)- wherein -(AA$^1$)- and -(AA$^2$)- preferably have the meanings given above, preferably -(AA$^1$)- being -Ile- or Ac$_6$c-, or (alternatively or in addition to the group of moieties mentioned just before -Ac$_7$c-, -Nbo- and -Gln-; and -(AA$^2$)- being -Asn- (preferred) or also -βala-;

or (even less preferably) simply a bivalent radical of an amino acid selected from the amino acids mentioned above, especially -Ile- or (alternatively or in addition to the group of moieties mentioned just before) -Ac$_6$c-, -Nbo- and Ac$_5$c-, and Y is monosubstituted amino selected from lower alkylamino, such as methylamino, ethylamino; isobutylamino or 3-methylbutylamino; octylamino, such as 2-ethylhexyl-amino; aryloxy-lower alkylamino, especially halonaphthyloxy-lower alkylamino, such as 2-(l-bromo-naphthalen-2-yloxy)-ethylamino, or naphthyloxy-lower alkylamino, such as 2(naphthalen-2-yloxy or naphthalen-1-yloxy)-ethylamino; aryl-lower alkylamino, such as phenyl-lower alkylamino, e.g. benzylamino, 3-phenylpropylamino, di-phenyl-lower alkylamino, such as 2,2-diphenyl-ethylamino or 3,3-diphenyl-propylamino, (mono- or di-halophenyl)-lower alkylamino, such as 2-(4-chlorophenyl) ethylamino or 3-(2,4-dichlorophenyl)-propylamino, naphthalenyl-lower alkylamino, such as 3-naphthtalen-1-ylpropylamino or 3naphthalen-2-ylpropylamino, hydroxy-naphthalenyl-lower alkylamino, such as 3-(2-hydroxynaphthalen-1-yl)-propylamino, or phenanthrenyl-lower alkylamino, such as 3-phenanthren9-yl-propylamino; cycloalkylamino, such as cyclohexylamino; and cycloalkyl-lower alkylamino, such as cyclohexylmethylamino; or a salt thereof where at least one salt-forming group is present.

More preferred is also a compound of formula I wherein n is 1, 2 or 3, especially 2 or 3;

X is oxalyl

PTI is a bivalent radical of phosphotyrosine (in the D-, L- (most preferred) or (less preferably) the (D,L)-form) or of a phosphotyrosine mimetic of the phosphono-(α,α-difluoro)methyl-phenylalanine or the phosphonomethyl-phenylalanine type, especially 4-phosphono-(α,α-difluoro)methyl-phenylalanine or the mimetics mentioned in the background of the invention —(AA)$_n$— has one of the following meanings:
A bivalent radical of a tripeptide of the formula -(AA$^1$)-(AA$^2$)AA$^3$)- wherein -(AA$^1$)- is preferably selected from -Ile-, Ac$_5$c-, -Ac$_6$c-, -Asp-, -Gly- and -Phe- or (alternatively or in addition to the group of moieties mentioned just before) from -Ac$_7$c-, -Nbo-, -Met-, -Pro-, -βAla-, -Gln-, -Glu-, -DHph-, -HPh- and -tLe-, most preferably -Ile-, -Ac$_5$c-, -Ac$_6$c-, -Asp- or -Gly- or (alternatively or in addition to the group of moieties mentioned just before) -Ac$_7$c-, -Nbo- and -Gln-; -(AA$^2$)- is preferably selected from -Asn-, and also from -βAla- and -Gly-, or (alternatively or in addition to the group of moieties mentioned just before), from -Ile-, -βAla- and Gln; most preferably -Asn-; and -(AA$^3$)- is preferably selected from -Val-, and -β-ala, and also from -Gly-, -Gln-, -Val-, -Asp- and -Ac$_5$c-; or, less preferably, a bivalent radical of a dipeptide of the formula -(AA$^1$)-(AA$^2$)- wherein -(AA$^1$)- and -(AA$^2$)- preferably have the meanings given above, preferably -(AA$^1$)- being -Ile- or $Ac_6c$-, or (alternatively or in addition to the group of moieties mentioned just before -$Ac_7c$-, -Nbo- and -Gln-; and -(AA²)- being -Asn- (preferred) or also -βala-;

or (even less preferably) simply a bivalent radical of an amino acid selected from the amino acids mentioned above, especially -Ile- or (alternatively or in addition to the group of moieties mentioned just before) -$Ac_6c$-, -Nbo- and $Ac_5c$-, and Y is monosubstituted amino selected from lower alkylamino, such as methylamino, ethylamino; isobutylamino or 3-methylbutylamino; octylamino, such as 2-ethylhexylamino; aryloxy-lower alkylamino , especially halonaphthyloxy-lower alkylamino , such as 2-(1-bromo-naphthalen-2-yloxy)-ethylamino, or naphthyloxy-lower alkylamino, such as 2(naphthalen-2-yloxy or naphthalen-1-yloxy)-ethylamino; aryl-lower alkylamino, such as phenyl-lower alkylamino, e.g. benzylamino, 3-phenylpropylamino, di-phenyl-lower alkylamino, such as 2,2-diphenyl-ethylamino or 3,3-diphenyl-propylamino, (mono- or di-halophenyl)-lower alkylamino, such as 2-(4-chlorophenyl) ethylamino or 3-(2,4-dichlorophenyl)-propylamino, naphthalenyl-lower alkylamino, such as 3-naphthalen-1-ylpropylamino or 3naphthalen-2-ylpropylamino, hydroxy-naphthalenyl-lower alkylamino, such as 3-(2-hydroxynaphthalen-1-yl)-propylamino, or phenanthrenyl-lower alkylamino, such as 3-phenanthrenyl9-yl-propylamino; cycloalkylamino, such as cyclohexylamino; and cycloalkyl-lower alkylamino, such as cyclohexylmethylamino; or a salt thereof where at least one salt-forming group is present.

More preferred is also a compound of formula I wherein n is 2 or 3;

PTI is a bivalent radical of phosphotyrosine (in the D-, L- (most preferred) or (less preferably) the (D,L)-form) or of a phosphotyrosine mimetic of the phosphono-(α,α-difluoro)methyl-phenylalanine type, especially 4-phosphono-(α,α-difluoro)methyl-phenylalanine or the mimetic mentioned above in the background of the invention -(AA)$_n$- has one of the following meanings:
A bivalent radical of a tripeptide of the formula -(AA¹)-(AA²)-(AA³)- wherein -(AA¹)- is selected from -Ile-, $Ac_5c$-, -$Ac_6c$-, -Asp-, or -Gly-; -(AA²)- is selected from -Asn-, and also from -βAla- and -Gly-, most preferably -Asn-; and -(AA³)- is selected from -Val-, and -βAla, and also from -Gly-, -Gln-, -Val-, -Asp- and -$Ac_5C$-; or a bivalent radical of a dipeptide of the formula -(AA¹)-(AA²)- wherein -(AA¹)- is -Ile- or -$Ac_6c$- and -(AA₂)- is -Asn-(preferred) or also -βala-;

Y is monosubstituted amino group such naphthalenyl-lower alkyl amino or a salt thereof.

More preferred is also a compound of formula I wherein n is 1, 2 or 3, especially 2 or 3;

X is oxalyl

PTI is a bivalent radical of phosphotyrosine (in the D-, L- (most preferred) or (less preferably) the (D,L)-form) or of a phosphotyrosine mimetic of the phosphono-(α,α-difluoro)methyl-phenylalanine or the phosphonomethyl-phenylalanine type, especially 4-phosphono-(α,α-difluoro)methyl-phenylalanine or the mimetic mentioned above in the background of the invention -(AA)$_n$- has one of the following meanings:
A bivalent radical of a tripeptide of the formula -(AA¹)-(AA²)-(AA³)- wherein -(AA¹)- is preferably selected from -Ile-, $Ac_5c$-, -$Ac_6c$-, -Asp-, or -Gly- and -Phe- or (alternatively or in addition to the group of moieties mentioned just before) from -$Ac_7c$-, -Nbo-, -Met-, -Pro-, -βAla-, -Gln-, -Glu-, -DHph-, -HPh- and -tLe-, most preferably -Ile-, -$Ac_5c$-, -$Ac_6c$-, -Asp- or -Gly- or (alternatively or in addition to the group of moieties mentioned just before) -$Ac_7c$-, -Nbo- and -Gln-; -(AA²)- is preferably selected from -Asn-, and also from -βAla- and -Gly-, or (alternatively or in addition to the group of moieties mentioned just before), from -Ile-, -βAla- and Gln; most preferably -Asn-; and -(AA³)- is preferably selected from -Val-, and - is preferably selected from -Val-, and -β-Ala, and also from -Gly-, -Gln-, -Val-, -Asp- and -$Ac_5c$-; or, less preferably, a bivalent radical of a dipeptide of the formula -(AA¹)-(AA²)- wherein -(AA¹)- and -(AA²)- preferably have the meanings given above, preferably -(AA¹)- being -Ile- or -$Ac_6c$-, or (alternatively or in addition to the group of moieties mentioned just before) $Ac_7c$-, -Nbo- and -Gln-; and -(AA²)- being -Asn- (preferred) or also -βAla-;

or (even less preferably) simply a bivalent radical of an amino acid selected from the amino acids mentioned above, especially -Ile- or (alternatively or in addition to the group of moieties mentioned just before) -$Ac_6C$-, -Nbo- and $AC_5c$-, and Y is monosubstituted amino selected from lower alkylamino, such as methylamino, ethylamino; isobutylamino or 3-methylbutylamino; octylamino, such as 2-ethyl-hexyl-amino; aryloxy-lower alkylamino, especially halonaphthyloxy-lower alkylamino, such as 2-(1-bromo-naphthalen-2-yloxy)-ethylamino, or naphthyloxy-lower alkylamino, such as 2-(naphthalen-2-yloxy or naphthalen-1-yloxy)-ethylamino; aryl-lower alkylamino, such as phenyl-lower alkylamino, e.g. benzylamino, 3-phenylpropylamino, di-phenyl-lower alkylamino, such as 2,2-diphenyl-ethylamino or 3,3-diphenyl-propylamino, (mono- or di-halo-phenyl)-lower alkyl-amino, such as 2-(4-chlorophenyl) ethylamino or 3-(2,4-dichlorophenyl)-propylamino, naphthalenyl-lower alkylamino, such as 3-naphthalen-1-ylpropylamino or 3naphthalen-2-ylpropylamino, hydroxy-naphthalenyl-lower alkylamino, such as 3-(2-hydroxy-naphthalen-1-yl)-propylamino, or phenanthrenyl-lower alkylamino, such as 3-phenanthrenyl-9-yl-propylamino; cycloalkylamino, such as cyclohexylamino; and cycloalkyl-lower alkylamino, such as cyclohexylmethylamino; or a salt thereof where at least one salt-forming group is present.

(SEQ ID NO:1);
oxalyl-Tyr($PO_3H_2$)-Ile-Asn-NH-[3-(2-hydroxy-naphthalen-1-yl)-propyl]

(SEQ ID NO:2);
oxalyl-Tyr($PO_3H_2$)-Ile-Asn-NH-(3-naphthalen-2-yl-propyl)

(SEQ ID NO:3);
oxalyl-Tyr($PO_3H_2$) $Ac_6c$-NH-(3-naphthalen-1-yl-propyl)

Detailed Description of Preferred Reaction Conditions

The compounds of the present invention preferably can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2$_{nd}$ edition, Pierce chemical Company, Rockford, Ill. (1984), in M. Bodanzsky and A. Bodanzsky, The Practice of Peptide Synthesis, Springer Verlag, New York (1984); and Applied Biosystems 430A Users manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X.

Salts of compounds of formula I having at least one salt-forming group may be prepared in a manner known per se. For example, salts of compounds of formula I having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I are obtained in customary manner, e.g. by treating the compounds with an acid or a suitable anion exchange reagent. Internal salts of compounds of formula I containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers and/or cis/transisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with oPTIcally pure salt-forming reagents and separation of the mixture of diastereoisomers so obtainable, for example by means of fractional crystallisation, or by chromatography over oPTIcally active column materials.

Starting Materials

Unless a specific method of synthesis is indicated for starting materials, the starting materials are known, can be prepared according to processes known per se, especially in analogy to methods given in the Examples, and/or are commercially available.

For example, suitably protected and/or preactivated D-, (D,L)- or L- amino acids, unnatural amino acids, di-, tri- or oligopeptides, derivatized and/or preloaded resins, the ancillary reagents and solvents required for either Boc or Fmoc peptide synthesis are commercially available from various suppliers or can be prepared readily according to standard procedures. In addition, di-or other oligopeptides can be prepared readily according to standard procedures. In addition, automated peptide synthesizers with optimized, preprogrammed Boc and Fmoc synthesis cycles are available from numerous sources.

The starting materials for the phosphotyrosine mimetics and the respective protected derivatives can be synthesized according to methods know in the art; (e.g., for phosphonomethy-phenylalanine, especially 4-phosphonomethyl-phenylalanine, see Synthesis 1991, 1019, Tetrahedron Lett. 32(43), 6061 (1991), Tetrahedron Lett. 33(9), 1193 (1992) and SynLett 1994, 233–254; for phosphono-($\alpha$-fluoro)methyl-phenylalanine, especially 4-phosphono-($\alpha$-fluoro)methyl-phenylalanine, see J. Chem, Soc., Perkin Trans. 1, 1986(1), 913–917 or Cancer Cells 2, 95 (1990) and J. Org. Chem 58, 1336–1340 (1993), for phosphono-($\alpha,\alpha$-difluoro-methyl-phenylalanine, especially 4-phosphono-($\alpha,\alpha$-difluoro)methyl-phenylalanine, see Tetrahedron Lett. 35, 551–554 (1994), Tetrahedron Lett. 34(22), 3543 (1993) and Tetrahedron Lett. 33(29), 4137 (1992), for phosphono-($\alpha$-hydroxy)methyl-phenylalanine, especially 4-phosphono-($\alpha$-hydroxy)methyl-phenylalanine, see Drugs of the Future 17, 119 (1992) and J. Org. Chem. 58, 1336–1340 (1993), for O-sulfo-tyrosine, such as 4-(O-sulfo)-tyrosine (=tyrosine sulfate), see Chem. Pharm. bull. 41, 376–380 (1993), for dicarboxy-methoxy-phenylalanine (=(HOOC)$_2$—CH$_2$—O-phenylalanine, especially 4-(dicarboxymethoxy)-phenylalanine, see Abstract No. 014.024.114 presented at the 109$^{th}$ American Chemical Society Meeting, Apr. 2–6 (1995) in Anaheim, Calif.; and for phosphono-phenylalanine, such as 4-phosphonophenylalanine, see Tetrahedron 46, 7793–7802 (1990)).

General Process Conditions

The following applies in general to all processes mentioned hereinbefore and hereinafter, while reaction conditions specifically mentioned above or below are preferred:

Functional groups in starting materials the reaction of which is to be avoided, especially carboxy, amino, hydroxy, mercapto and sulfo groups, can be protected by suitable protecting groups (conventional protecting groups) which are customarily used in the synthesis of peptide compounds, and also in the synthesis of cephalosporins and penicillins as well as nucleic acid derivatives and sugars. These protecting groups may already be present in the precursors and are intended to protect the functional groups in question against undesired secondary reactions, such as acylation, etherificabon, esterification, oxidation, solvolysis, etc. In certain cases the protecting groups can additionally cause the reactions to proceed selectively, for example stereoselectively. It is characteristic of protecting groups that they can be removed easily, i.e. without undesired secondary reactions taking place, for example by solvolysis, reduction, photolysis, and also enzymatically, for example also under physiological conditions, and, especially, that they are not present in the end products.

The protection of functional groups by such protecting groups, the protecting groups themselves and the reactions for their removal are described, for example, in standard works such as J. F. W. McOmie, "Protective Groups in organic Chemistry", Plenum Press, London and New York 1973, in Th. W. Greene, Protective Groups in organic Synthesis", Wiley, New York 1981, in "The Peptides", Volume 3 (E. Gross and J. Meienhofer, eds.), Academic Press, London and New York 1981, in "Methoden der organischen Chemie", llouben-Weyl, 4th edition, Volume 15/l, Georg Thieme Verlag, Stuttgart 1974, in H.-D. Jakubke and H. Jescheit, "Aminosauren, Peptide, Proteine" ("Amino acids, peptides, proteins"), Verlag Chemie, Weinheim, Deerfield Beach and Basle 1982, and in Jochen Lehmann, "Chemie der Kohlenhydrate: Monosaccharide und Derivate" ("The Chemistry of Carbohydrates: Monosaccharides and derivatives"), Georg Thieme Verlag, Stuttgart 1974.

When several protected functional groups are present, H desired the protecting groups can be so selected that more than one such group can be removed simultaneously, for example by acidolysis, such as by treatment with trifluoroacetic acid, or with hydrogen and a hydrogenation catalyst, such as a palladium-on-carbon catalyst. Conversely, the groups can also be so selected that they cannot all be removed simultaneously, but rather in a desired sequence, the corresponding intermediates being obtained.

In view of the close relationship between the compounds of formula I and their salts and starting materials (starting materials and intermediates) in free form and in the form of their salts, any reference hereinbefore and hereinafter to a free compound or a salt thereof is to be understood as meaning also the corresponding salt or free compound, respectively, where appropriate and expedient.

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation agents or neutralising agents, for example ion exchangers, such as cation exchangers, e.g. in the H$^+$ form, depending on the nature of the reaction and/or of the reactants at reduced, normal or elevated temperature, for example in a temperature range of from approximately 100° C. to approximately 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers.

The solvents from which those solvents that are suitable for any particular reaction may be selected include, for example, water, esters, such as lower alkyl-lower alkanoates, for example ethyl acetate, ethers, such as aliphatic ethers, for example diethyl ether, or cyclic ethers, for example tetrahydrofuran, liquid aromatic hydrocarbons, such as benzene or toluene, alcohols, such as methanol, ethanol or 1- or 2-propanol, nitriles, such as acetonitrile, halogenated hydrocarbons, such as methylene chloride, acid amides, such as dimethylformamide, bases, such as heterocyclic nitrogen bases, for example pyridine, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallisation. Different crystalline forms may be present.

If necessary, protected starting materials may be used in all process steps and the protecting groups may be removed at suitable stages of the reaction.

Pharmaceutical Compositions

The invention relates also to pharmaceutical compositions comprising compounds of formula I, to their use in the therapeutic (including prophylactic) treatment of the diseases mentioned above, to the compounds for said use and to the preparation of pharmaceutical preparations.

The pharmacologically acceptable compounds of the present invention may be used, for example, for the preparation of pharmaceutical compositions that comprise an effective amount of the active ingredient together or in admixture with a significant amount of inorganic or organic, solid or liquid, pharmaceutically acceptable carriers.

The invention relates also to a pharmaceutical composition that is suitable for administration to a warm-blooded animal, especially a human (or to cells or cell lines derived from a warm-blooded animal, especially a human, e.g. lymphocytes), for the treatment or prevention of (=prophylaxis against) a disease that responds to diseases that respond to inhibition of the interaction of proteins comprising SH2 domains and phosphoproteins, especially a phosphorylated protein tyrosine kinase or modified versions thereof, preferably inhibition of the interaction of Grb2 SH2 with a phosphoprotein containing a -Tyr(PO$_3$H$_2$)-X-Asn-motif, such as phosphorylated EGFR protein tyrosine kinase or modified derivatives thereof, but also other phosphoproteins such as SHC or modified derivatives thereof, comprising an amount of a compound of formula I or a pharmaceutically acceptable salt thereof, which is effective for said inhibition, especially the inhibition of the interaction of Grb2 SH2 with a phosphoprotein containing a -Tyr(PO$_3$H$_2$)-X-Asn-motif, such as phosphorylated EGFR protein tyrosine kinase or modified derivatives thereof, but also other phosphoproteins such as SHC, or truncated derivatives thereof, together with at least one pharmaceutically acceptable carrier.

The pharmaceutical compositions according to the invention are those for enteral, such as nasal, rectal or oral, or parenteral, such as intramuscular or intravenous, administration to warm-blooded animals (humans and animals), that comprise an effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to a method of treating diseases that respond to inhibition of the interaction of proteins comprising SH2 domains and phosphoproteins, especially the phosphorylated protein tryrosine kinases or modified versions thereof; preferably of Grb2 SH2 with a phosphoprotein containing a -Tyr(PO$_3$H$_2$)-X-Asn- motif, such as phosphorylated EGFR protein tyrosine kinase or modified derivatives thereof, but also other phosphoproteins such as SHC or modified derivatives thereof; which comprises administering a prophylactically or especially therapeutically effective amount of a compound of formula I according to the invention, especially to a warm-blooded animal, for example a human, that, on account of one of the mentioned diseases, requires such treatment. The dose to be administered to warm-blooded animals, for example humans of approximately 70 kg body weight, is from approximately 3 mg to approximately 30 g, preferably from approximately 10 mg to approximately 1.5 g, for example approximately from 100 mg to 1000 mg per person per day, divided preferably into 1 to 3 single doses which may, for example, be of the same size. Usually, children receive half of the adult dose.

The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, dragees, tablets or capsules.

The pharmaceutical compositions of the present invention are prepared in a manner known per se, for example by means of conventional dissolving, lyophilising, mixing, granulating or confectioning processes.

Solutions of the active ingredient, and also suspensions, and especially isotonic aqueous solutions or suspensions, are preferably used, it being possible, for example in the case of lyophilised compositions that comprise the active ingredient alone or together with a carrier, for example mannitol, for such solutions or suspensions to be produced prior to use. The pharmaceutical compositions may be sterilised and/or may comprise excipients, for example preservatives, stabilisers, wetting and/or emulsifying agents, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxy-methylcellulose, carboxymethyllcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules It is also possible for them to be incorporated into plastic carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tricalcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxy-methyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it being possible also for stabilisers and/or antibacterial agents to be added. Dyes or pigments may be added to the tablets or dragee coatings or the capsule casings, for example for identification purposes or to indicate different doses of active ingredient.

EXAMPLES

Embodiments of the invention are described in the following specific examples which are not to be construed to be intended to limit the scope of the invention in any way, but serve merely for illustration:

Temperatures, if not mentioned: room temperature/ambient temperature. In mixtures, relations of parts of solvent or eluent or reagent mixtures in liquid form are given as volume relations (v/v), if not indicated otherwise.

Synthesis pTyr-containing β-bend mimetic 18b is within the structural family of Grb2 SH2 domain antagonists previously synthesized by solid-phase techniques.[53] In spite of repeated attempts, we were unable to achieve the synthesis of 18b by solid-phase methods. This failure was most probably related to steric crowding proximal to α-amino and carboxyl groups of the β-bend forming 1-aminocyclohexane carboxylic acid residue (13). All synthesis were therefore conducted by solution methods. Key napthylpropylamine-containing dipeptide 14 was prepared by reacting amine 11 with the N-hydroxysuccinimide active ester of N-Boc L-asparagine to yield the corresponding amide 12. The required naphth-ylpropyl amine 11 has previously been reported,[54] however it was found expeditious to prepare it by the alternate route shown in Scheme 1. After deprotection of 12a to amine 12b, coupling N-Boc 1-aminocyclohexane carboxylic acid (13) provided the protected dipeptide 14a (Scheme 2). Free dipeptide amine 14b, obtained upon standard N-deprotection, was coupled with Tyr (15a), pTyr (15a) or pTyr mimetics 15c,[40] 15d,[55] 15e[56] or 15f,[56] all bearing suitable protecting groups. Removal of amino protection and acetylation gave the corresponding N-acetyl analogues 17a–f, which after cleavage of remaining protection groups and HPLC purification, gave final tripeptides 18a–f (Scheme 3). Of note was tripeptide 17f, which required removal of the 2-trimethyl silylethyl ester (tetrabutylammonium fluoride) prior to TFA treatment.[56] Synthesis of oxalyl-containing analogues 20d and 20f were identical to that described for analogues 18d and 18f respectively, except that N-acetylation with tert-butyl oxylate was performed rather than acetylation (Scheme 4).
Scheme 1
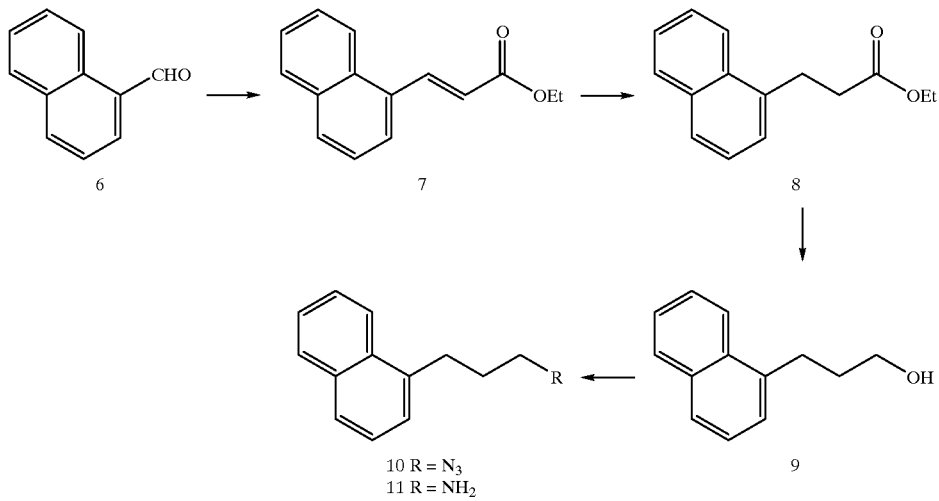
Scheme 2
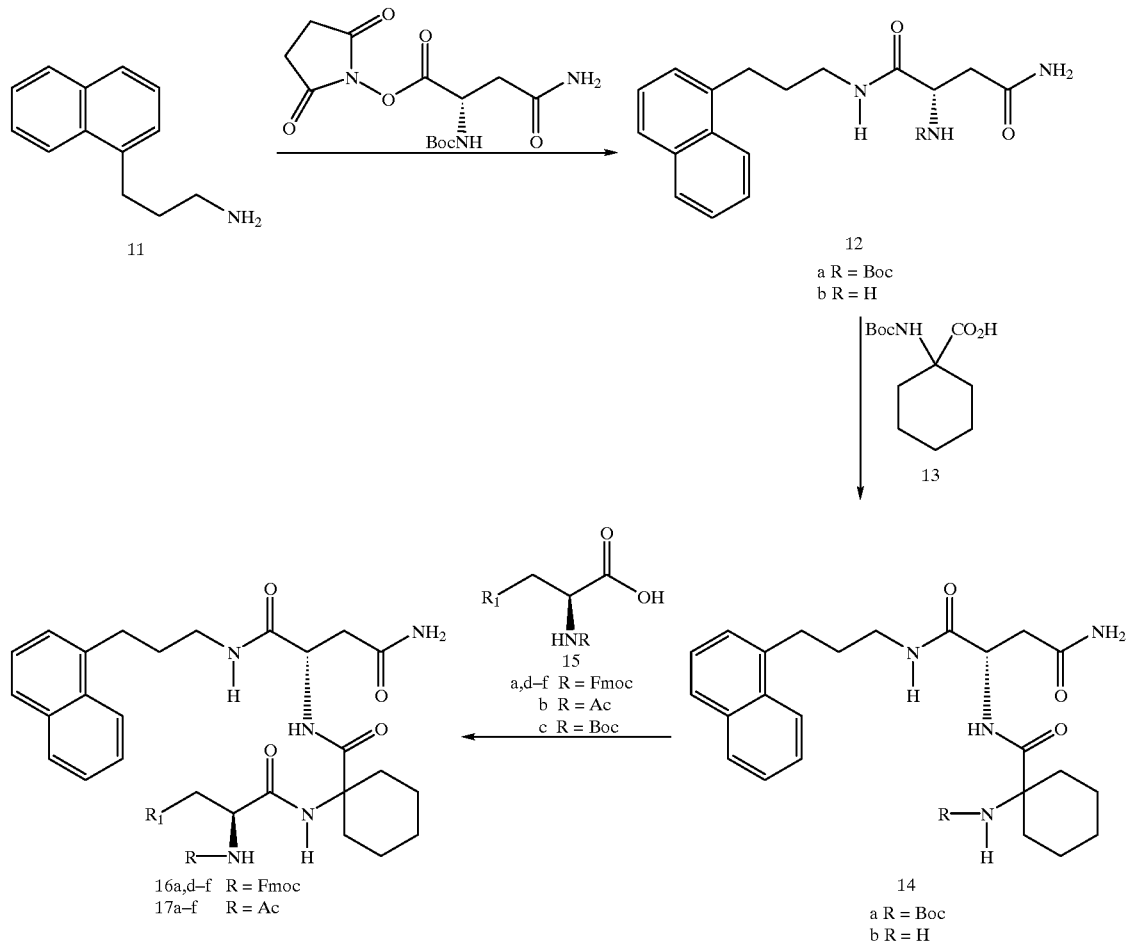

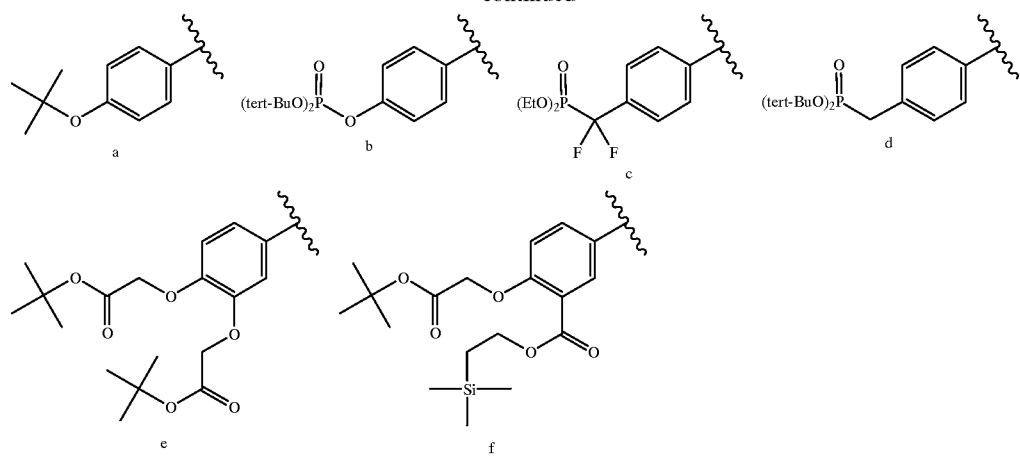
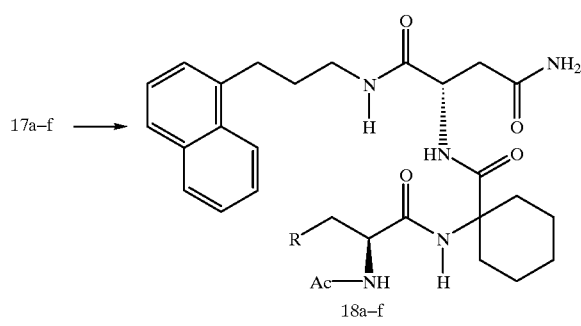
Scheme 3
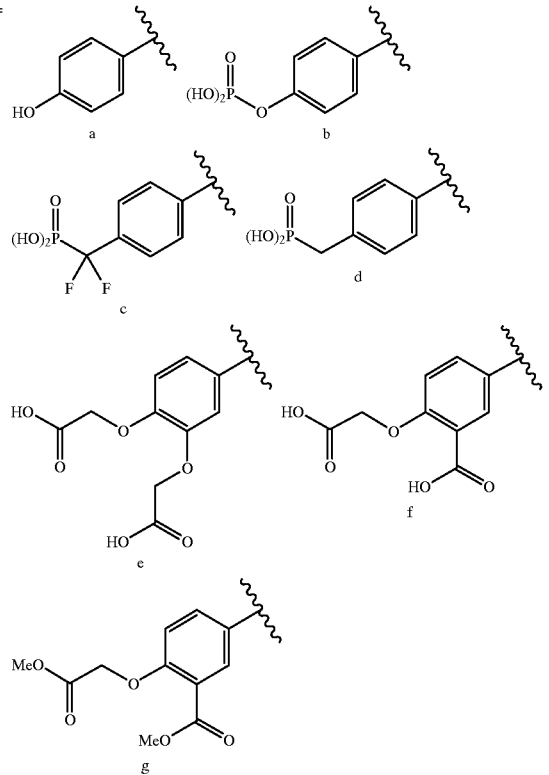
Scheme 4
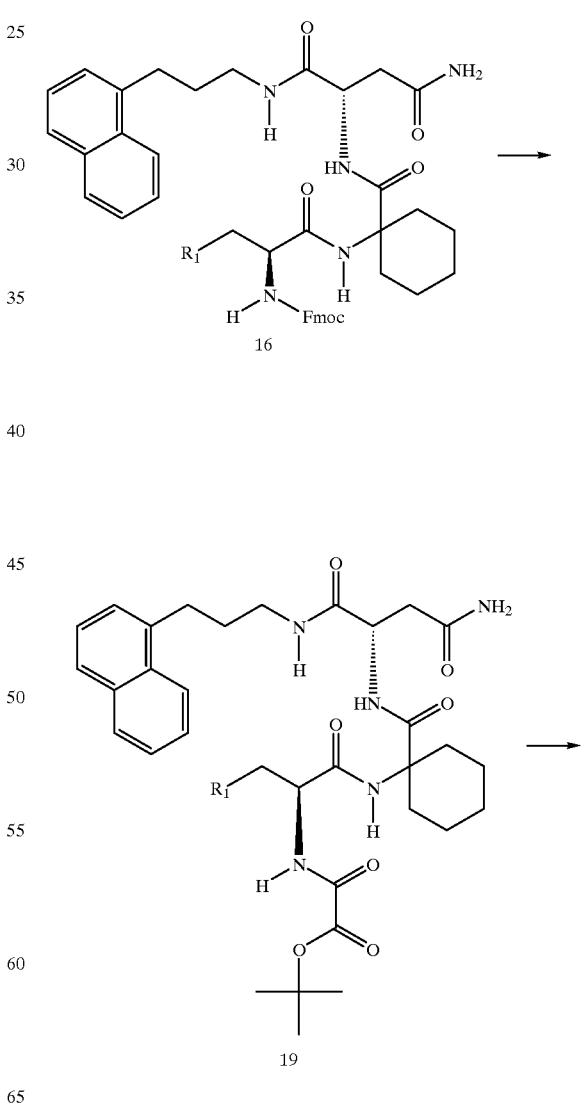

-continued

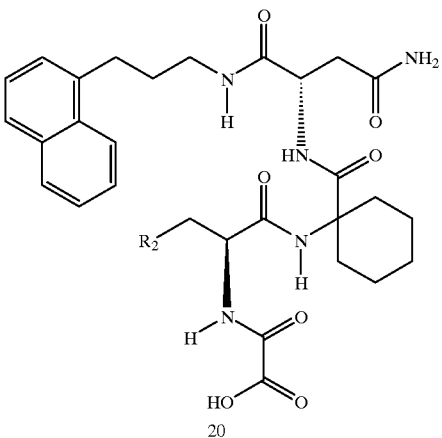

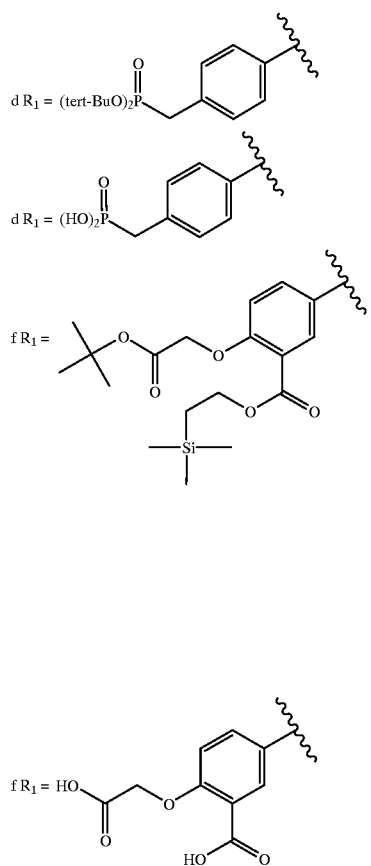

Results and Discussion

The present work examines non phosphate-containing pTyr mimetics in the context of Grb2 SH2 domain binding systems. The Grb2 SH2 domain affords an ideal target for such a study because it provides critical links between growth factor receoptor PTKs and down stream signalling events involving Ras-proteins, which have been directly implicated with oncogenic processes. Examples of this include members of the epidermal growth factore receptor (EGFR) PTK family such as ErbB-2 (HER-2/neu), which are found in a large proportion of breast cancers,[57] the Met (hepatocyte growth factor/scatter factor) PTK, which is over-expressed in many human tumors,[58] and the Bcr-Abl PTK, which is necessary for Philadelphia chromosome positive leukemia.[59,60] There is a significant over expression of mRNA for ErbB-2 in many breast cancers, with an associated increase in the levels of its phosphorylated gene product, p185$^{erbB-2}$. In experimental cell systems such an overexpression of p185$^{erbB-2}$ leads to cell transformation,[61-62] and signalling via Grb2 has also been shown to be sufficient to transform such cells.[63,64] Blockade of Grb2 SH2 domain binding could potentially provide a means of uncoupling p185$^{erbB-2}$ from the Ras pathway and in so doing, attenuate its transforming effects. Accordingly, oblation of Grb2 function, either by elimination of the entire Grb2 protein through antisense polynucleotides[59] or by competitive blockade of Grb2 SH2 domain binding interactions with pTyrcontaining peptides,[45,46] can inhibit cell growth or EGF-induced Ras/mitogen-activated protein kinase signalling, respectively.

Design of inhibitors directed against the Grb2 SH2 domain is facilitated by the existence of significant structural information in the form of X-ray analysis of the free domain,[65] as well as thermodynamic[66] NMR[67] and X-ray[30] analysis of Grb2 SH2 domains ligated to pTyr-containing ligands. In contrast to X-ray studies of several SH2 domains which show that binding of pTyr-containing peptides occurs in linear fashion,[68] recent studies on Grb2 SH2 domains have shown that ligand binding occurs in B-bend orientation.[30,67,69] This enhances the attractiveness of Grb2 SH2 domains as targets for inhibitor design, due to the applicability of β-bend mimeticking structures. A Novartis group has accordingly reported several high affinity pTyr-containing ligands, which in addition to having in common a pTyr residue that binds in the pTyr pocket and an Asn residue in the pTyr+2 position, contain other features that enhance Grb2 binding affinity.[70] Among these features are elements which induce β-bend conformations, as shown by cyclic peptide 21 (IC$_{50}$=0.37 µM)[69] and β-bend mimeticking open-chain tripeptides typified by 22 (IC$_{50}$=0.011 µM)[53] which utilize a 1-aminocyclohexanecarboxylic acid in the pTyr+1 position to facilitate β-bend formation.[71] This latter type of structure provided an ideal starting points for the current study, which is focused on interactions within the pTyr binding pocket.

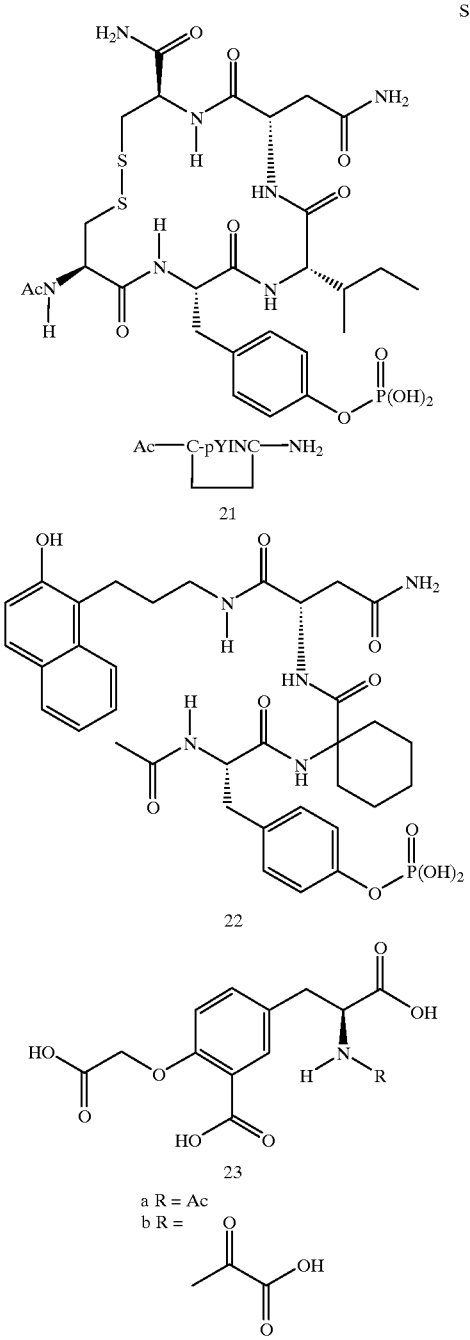

Structures 2

Plasmon Reasonace Binding Studies

In order to examine pTyr mimetics in the context of Grb2 SH2 inhibitors, the recently disclosed high affinity pTyr-containing tripeptide 18b[53] was chosen as a model platform on which to append phosphotyrosyl-mimeticking analogues. A series of new inhibitors 18c–f and 20d and 20f incorporating pTyr mimetics 15c–f was prepared and Grb2 SH2 domain binding affinities were determined by surface plasmon reasonance (FIGS. 1 and 2).[72,73] The linear Shc(Y317) peptide D-D-P-S-pY-V-N-V-Q (24) was employed as a reference, and gave an $IC_{50}$ of 1.3 μM in this system. Consistent with previous reports,[53] the parent pTyr-containing 18b also exhibited very potent binding affinity ($IC_{50}$=0.07 μM). The importance of the "phosphate pharmacophore" to the overall binding of 18b was confirmed by the loss of all measureable binding affinity upon removal of the phosphate group (compound 18a).

Figure 2:
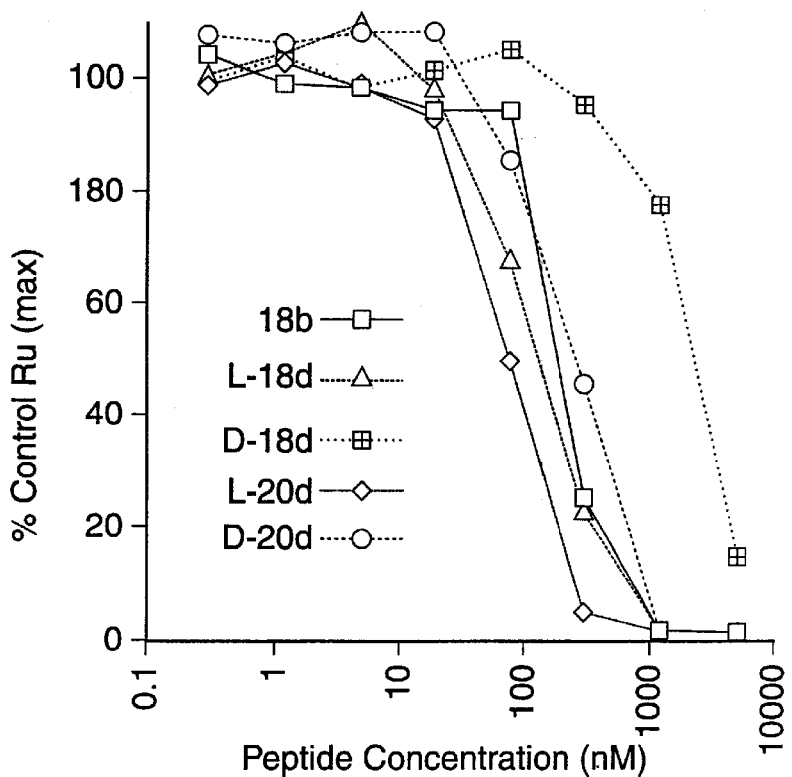
FIG. 2 depicts the Grb2 SH2 domain binding affinities, as determined by the surface plasmon resonance method, of compounds L-18d, D-18d, L-20d, and D-20d. Compound 18d was used as a control.

Experiments were conducted with phosphonate-containing analogues. The difluorophosphonate-based analogue 18c ($IC_{50}$=0.08 μM) was found to be equally potent to the pTyr-containing parent, which contrasts with the previous demonstration of a five-fold reduction in potency in a Grb2 SH2 domain binding system for a linear $F_2$Pmp-containing peptide relative to its pTyr-containing homologue.[42] The non-fluorinated phosphonate-containing compound L-18d[74] showed inhibitory potency equivalent to the $F_2$Pmp-containing 18c, which is also somewhat unexpected, as for other SH2 domain systems, Pmp-containing analogues frequently show reduced inhibitory potency[25,41,42,48] Also seen in FIG. 2 is the marked loss of potency for the D-Pmp containing compound D-18d[63] relative to its L-counterpart.

Carboxylate-based pTyr mimetics were examined next. Non phosphorus-containing pTyr mimetics such as OMT (4), were originally designed to afford structural alternatives to phosphorus-containing pTyr mimetics.[50] In the current study, analogues 18e and 18f were envisioned to function as variants of OMT in which one malonyl carboxyl has been replaced with a hydrogen, while the second carboxyl has been translocated to a more distal location. Retention of two carboxyl groups deemed necessary in order to provide the di-anionic "phosphate pharmacophore" which interacts with two critical arginines within the pTyr binding pocket. As seen in FIG. 1, appending the second carboxyl to a second flexible side chain resulted in a dramatic loss of binding affinity (18e, $IC_{50}$>>100 μM). Anchoring the second carboxyl directly onto the aryl ring resulted in significantly better affinity (18f, $IC^{50}$=6.7 μM).

Figure 3C:
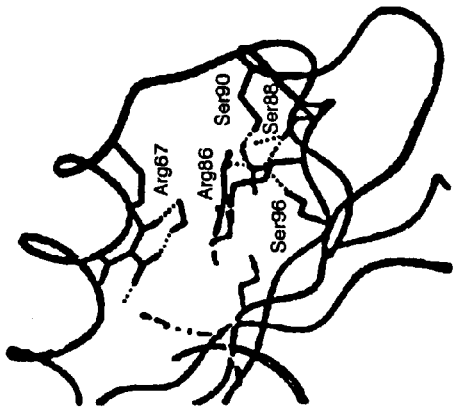
FIGS. 3A–3C depict the interactions within the pTyr-binding pocket of ligated Grb2 SH2 domain, as determined by molecular modeling.
Figure 3C:
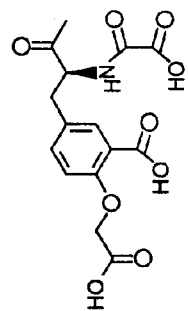
Figure 3B:
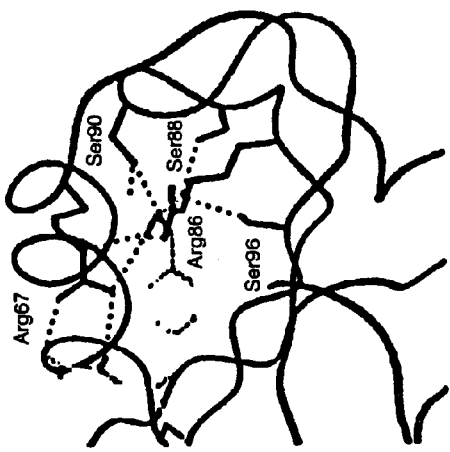
Figure 3B:
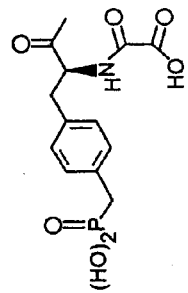
Figure 3A:
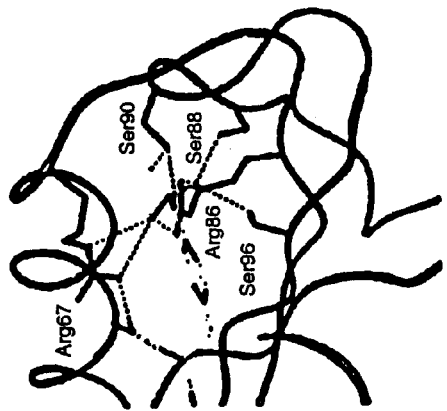
Figure 3A:
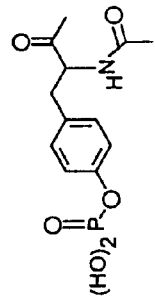

The reduced binding potency of 18f relative to phosphate-containing analogue 18b could potentially indicate that interactions of the two carboxyls of 18f with Arg67 (α-helix) and Arg86 (β8C-strand) within the pTyr binding pocket, do not faithfully approximate that provided by the phosphorus-containing parent structure 18b. Note was therefore taken of the fact that the tyrosyl α-nitrogen provides a site from which additional critical interaction with Arg67 can be derived.[70] To examine whether introduction of anionic functionality onto the tyrosyl α-nitrogen could allow beneficial interaction with the positively charged Arg67 residue, pTyr mimetic 23a was modified by appending an N-oxalyl group to yield tricarboxylic analogue 23b. A conceptually similar approach has been used in the design of a phosphorylated 2-(phenylmethyl)succinic acid pTyr mimetic.[75] FIG. 3C depicts the results of a molecular dynamics simulation examining one possible manner in which 23b could interact with the pTyr binding pocket. of particular note is the ability of the Nα-oxalyl carboxyl to bind to the α-helix Arg67. Also evident are the ways in which the aryl bis-carboxyls of 23b can provide key recognition features displayed by the parent phosphate group (FIG. 3A). Introduction of mimetic 23b into the general β-bend mimeticking platform was achieved in straight forward fashion by N-terminal acylation using tert-butyl oxalate prior to final TFA-mediated deprotection. Consistent with modelling expectations, increased binding affinity was observed (20f, $IC_{50}$=1.3 μM). This five-fold enhancement in affinity makes the non phosphorus-containing 20f equivalent in potency to the reference linear phosphopeptide 24, which was based on the physiologically relevant Shc(Y317) sequence.

The ability of Nα-oxalyl functionality to enhance the binding interaction of the carboxy pTyr mimetic, suggested that Nα-oxalyl functionality could potentially have beneficial effects on Pmp-containing inhibitors. Molecular modelling dynamics simulations of Nα-oxalyl Pmp-containing 20d in the pTyr binding pocket, showed that while maintaining key binding interactions of the pTyr-containing 18b, significant new interactions between the Arg47 residue and elements of the Nα-oxalyl group were evident (FIG. 3A and B). These modelling predictions were consistent with plasmon reasonance binding which showed that oxalyl-L-Pmp (L-20d)[74] binds with higher affinity than L-18d (FIG. 2). For the D-Pmp analogue (D-20d)[74], the enhancing effect of the Nα-oxalyl group is even more pronounced relative to parent analogue D-18d (FIG. 2).

Inhibition of Grb2 SH2 Domain Binding in Cell-based Systems

Figure 4:
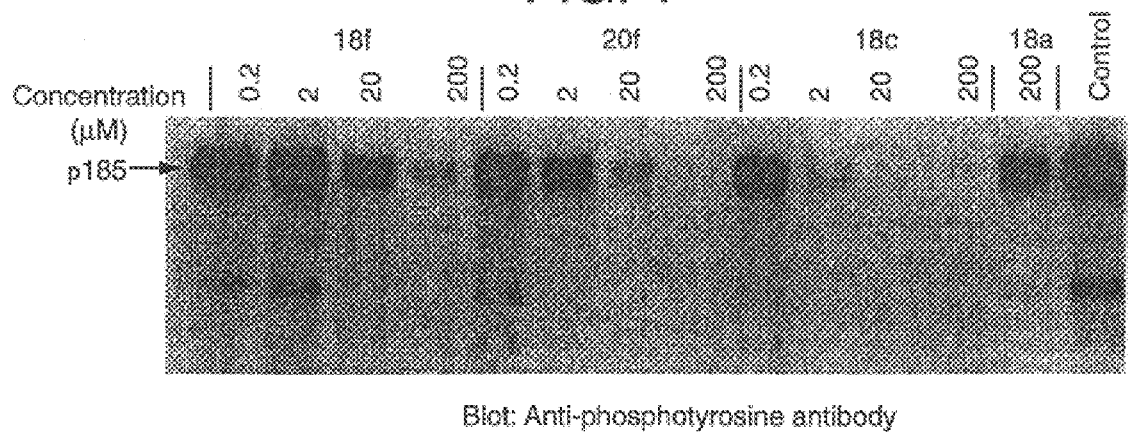
FIG. 4 depicts the inhibition of Grb2 SH2 binding interaction with tyrosine phosphorlated p185$^{erbB-2}$ as determined by anti-phosphotyrosine antibody western blotting. Compounds 18f, 20f, 18c, and 18a were tested for their ability inhibit interaction between intact Grb2 protein with a natural protein target, p185$^{erbB-2}$.

Data in FIGS. 1 and 2 reflect inhibition measured in isolater] Grb2 SH2 domain protein relative to a reference phopsho-Shc(Y317) peptide. In physiological contexts however, Grb2 SH2 domains exist as part of larger Grb2 proteins which bind to pTyr-containing ligands are themselves protein in nature. In order to examine the ability of synthetic analogues to inhibit the interaction of native Grb2 with p185$^{erbB-2}$ two assays were used, one in which they were introduced directly into cell lysates and one of which required the compounds to cross membranes of intact cells. In both cases, MDA-MB-453 cells were utilized. These cells are derived from a human breast cancer where there is amplification of erbB-2 gene and resultant overexpression of mRNA and protein. In these cells there is a heavily phosphotyrosinylated protein detectable by immuoblotting of cell lysates, which corresponds to the overexpressed p185$^{erbB-2}$.[76] Interaetion of native Grb2 protein with ErbB2 was monitored by immunopreeipitating Grb2 and detecting the amount of p185$^{erbB-2}$ which is co-precipitated using anti-phosphotyrosine western blotting.[73] As shown in FIG. 4, when F$_2$Pmp-containing 18c and tricarboxy-based 20f are introduced into MDA-MB-453 cell lysates, there is a clear dose-dependent reduction in the associated p185$^{erbB-2}$ bound to Grb2. Consistent with plasmon reasonace binding data (FIGS. 1 and 2) the level of inhibition is somewhat higher for 18c as compared to 20f. Removal of the oxalyl group (dicarboxy-based 18f) resulted in a measurable loss of potency.

Figure 5:
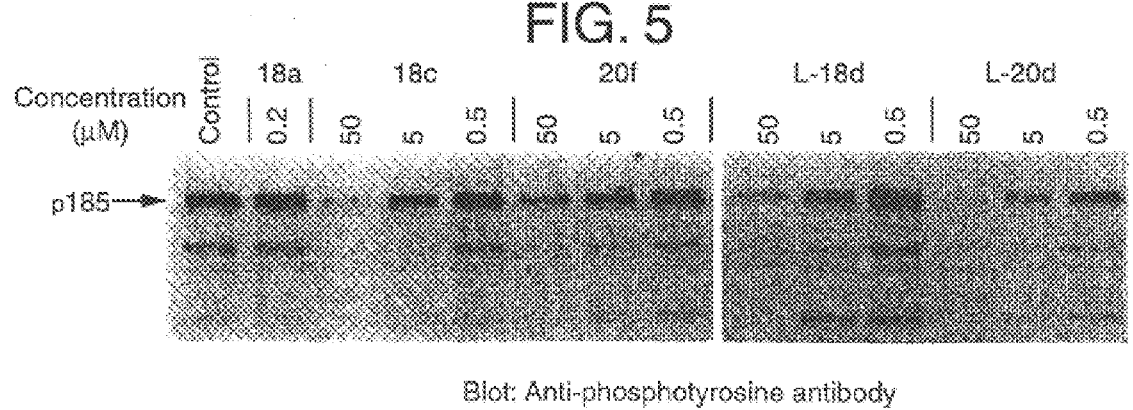
FIG. 5 depicts the inhibition of Grb2 SH2 binding interaction with tyrosine phosphorlated p185$^{erbB-2}$ as determined by anti-phosphotyrosine antibody western blotting. Compounds 18a, 18c, 20f, L-18d, and L-20d were tested for their ability to inhibit interaction between intact Grb2 protein with p185$^{erbB-2}$.

Compounds were also examined in a whole cell assay in which inhibition of intracellular Grb2 binding was measured following application of compounds to the media of MDA-MB-453 cells. These conditions required that compounds transit the cell membrane. As shown in FIG. 5, while the non-phosphorylated tyrosyl analogue 18a showed no measurable inhibition even at 50 μM concentration, compounds 18c, 20f, 18d and L-20d were able to inhibit Grb2 interaction with p185$^{erbB-2}$. In this assay, oxalyl-L-Pmp containing L-20d was clearly the most potent analogue with densiometric scanning of the blot indicating an IC$^{50}$ value potentially as low as 0.5 μM. Comparison of the cellular data in FIG. 5 with the cell-free IC$_{50}$ values obtained by surface plasmon reasonance shows an approximate 50-fold reduction in potency incurred by cell membrane transit. While evaluation of IC$_{50}$ values is likely to vary with the time of exposure to the compound, the cell line and the exact methodology used, these results suggest that oxalyl-L-Pmp containing L-20d is a potent inhibitor of Grb2 when applied to intact cells.

Conclusions

Development of Grb2 SH2 domain binding inhibitors has important implications for treatment of a variety of cancers. To date, Grb2 SH2 domain blockers used in cellular contexts have been large highly charged peptides which relied on special transport devices for cell membrane penetration.[45,46,77] The work presented in the current study has focused on pTyr mimetics and their potential application to cell-based studies. New non phosphorus-containing pTyr mimetics 23a and 23b have been introduced, which when incorporated into high affinity β-bend mimeticking platforms 18f and 20f, are able to exhibit Grb2 SH2 domain with low micromolar affinity. To our knowledge, the potency of these analogues is among the best yet reported for a non phosphorus-containing SH2 domain inhibitor. Compounds 18f and 20f are relatively compact, highly lipophilic molecules which represent improvements over previously reported non pTyr-containing competitive antagonists to Grb2 SH2 domains that have utilized much larger peptide structures, bearing multiple acidic amino acid residues.[73,77] The present study has also demonstrated the usefulness of the Nα-oxalyl group as an auxilary which enhances the binding potency of both phosphorus and non phosphorus-containing pTyr mimeties. When combined with the Pmp residue to give analogues such as L-20d, potent inhibition of Grb2 SH2 domain binding can be achieved in extracellular assays. More importantly, when administered to cells without prodrug derivatization, intracellular inhibition of Grb2 SH2 domain binding is achieved at micromolar to sub-micromolar concentrations. The oxalyl-containing pTyr mimetics presented in this study should be of general usefulness for the development of other Grb2 SH2 domain antagonists, independent of the particular β-bend mimeticking platform utilized for their display.

Experimental

Biological

SH2 domain using Surface Plasmon Resonance (SPR). The methods used were designed to measure a solution IC$_{50}$ for peptide inhibition of the Grb2 SH2 domain. The approach minimizes the "left shift" encountered in SPR experiments that is observed when binding equilibrium constants are determined from association and dissociation rates at the SPR surface. In this study the SPR serves simply as a detector of free Grb2 in solution. The IC$_{50}$ values are determined by mixing peptide with recombinant Grb2 or Grb2 SH2 domains and then measuring the amount of binding at equilibrium to the immobilized SHC phosphopeptide. The methods were essentially as previously described for the quantitative comparison of binding constants for the binding of other SH2 domains with phosphopeptides in solution.[72] In our experiments the immobilized phase was generated using SHC phosphopeptide, biotin-DDPSpYVNVQ (Quality Controlled Biochemicals, QCB), >90% purity by C$_{18}$ HPLC and of the appropriate molecular weight (1453) by mass spectrometry. This peptide was attached to SA5 chips at 2 nM. Binding of GST-Grb2 was conducted at 200 nM in HBS buffer (20 mM Hepes pH 7.4, 150 mM NaCl, 0.01% Triton X-100 at flow rate of 5 μL/min for 10 minutes. Total Ru change for GST-Grb2 or GST-Grb2SH2 binding to SHC phosphopeptide in the absence of inhibitors was 150–250 Ru. Compounds were tested as inhibitors at the indicated concentrations were pre-mixed with the GST-Grb2 prior to introduction onto the immobilized chip monitored. The SHC phospho peptide, DDPSpYVNVQ, was obtained from QCB. Equilibrium binding Ru was determined at 20 seconds following the last GST-Grb2 flowing across the chip. Two experiments were conducted using separate sensor chips and peptide dilutions.

Inhibition of Grb2 SH2 domain binding in cell extracts. Cell lysates were prepared from serum-treated erbB-2 overexpressing breast (MDA-MB-453) cancer cells using 1%

TritonX-100 in PBS containing 0.2 mM NaVO$_4$. Lysates were incubated with the indicated concentration of inhibitory compounds for 30 minutes. Grb2 and associated Grb2-binding proteins were immunoprecipitated from each lysate (5 mg) with anti-Grb2 antibodies and collected using protein A sepharose using methods previously described.[67] Immunoprecipitated proteins were separated by SDS PAGE on 8–16% gradient gels (Novagen). pTyr containing proteins were detected by Western blotting using anti-phosphotyrosine antibodies (Upstate Biochemicals Inc.). Previous experiments have shown that a major tyrosine phosphorylated protein in these cells is the p185$^{erbB-2}$, which is overexpressed as a consequence of gene amplification.[76]

Inhibition of Grb2 SH2 domain binding in whole cells. MDA-MB-453 cells were treated with the indicated compounds of for 3 hours in serum free media, IMEM, (Gibco). Cells were washed twice with PBS to remove the inhibitory compound. To determine the amount of phosphotyrosine bound p185$^{erbB-2}$ cells were then treated as described described above; cells were lysed Grb2 was immunoprecipitated and phosphotyrosine containing proteins were detected using immunoblotting and anti-phosphotyrosine antibody.

Synthesis

General synthetic methods. Elemental analyses were obtained from Atlantic Microlab Inc., Norcross, Ga. and fast atom bombardment mass spectra (FABMS) were acquired with a VG Analytical 7070E mass spectrometer under the control of a VG 2035 data system. $^1$H NMR data were obtained on Bruker AC250 (250 MHz) and are reported in ppm relative to TMS and referenced to the solvent in which they were run. Solvent was removed by rotary evaporation under reduced pressure and silica gel chromatography was performed using Merck silica gel 60 with a particle size of 40–63μ. Anhydrous solvents were obtained commercially and used without further drying. Preparative HPLC were conducted using a Waters Prep LC4000 system having photodiode array detection.

Ethyl 3-(naphth-1-yl)prop-2-eneate (7)

To a suspension of NaH (60% in mineral oil, 2.4 g, 60 mmol) in anhydrous ether (200 mL) was slowly added a solution of triethyl phosphonoacetate (12.33 g, 55 mmol) in anhydrous ether (25 mL) over 30 minutes at 0° C. and the mixture was stirred at 0° C. (1 h). A solution of 1-naphthaldehyde 6 (90–95%; 8.44 g, ~54 mmol) in ether (25 mL) was added and the reaction was allowed to warm to room temperature and then stirred (8 h). After an extractive aqueous workup, the resulting organic layers were dried (Na$_2$SO$_4$) and solvent removed to provide 7 as a colorless oil[75] (12.47 g, 102% based on aldehyde). $^1$H NMR (CDCl$_3$) δ 8.62 (1H, d, J=15.9 Hz), 8.29 (1H, d, J=8.1 Hz), 7.97 (2H, m), 7.8S (1H, d, J=7.1 Hz), 7.54~7.70 (3H, m), 6.62 (1H, d, J=15.9 Hz), 4.41 (1H, q, J=7.1 Hz), 1.47 (3H, t, J=7.1 Hz).

Ethyl 3-(naphth-1-yl)propaneate (8)

A solution of 7 (12 g, 53.1 mmol) in 95% EtOH (180 mL) was hydrogenated over 10% Pd.C (600 mg) at room temperature using an H$_2$ filled balloon (overnight). The reaction mixture was filtered and taken to dryness to give a 8 as a clear oil[80] (11.9 g, 98%). $^1$H NMR (CDCl$_3$) δ 8.05 (1H, d, J=7.8 Hz), 7.86 (1H, dd, J=2.7, 7.6 Hz), 7.75 (1H, d, J=7.6 Hz), 7.35~7.58 (4H, m), 4.17 (2H, q, J=7.1 Hz), 3.44 (2H, t, J=8.1 Hz), 2.77 (2H, t, J=8.3 Hz), 1.26 93H, t, J=7.1 Hz).

3-(Naphth-1-yl)propan-1-ol (9)

To a suspension of LiAlH$_4$ (1.91 g, 50.4 mmol) in anhydrous ether (50 mL) was added dropwise a solution of 8 (11.5 g, 50.4 mmol) in ether (50 mL) over 30 minutes at 0° C. under argon and then the mixture was stirred at room temperature (overnight). The reaction mixture was cooled to 0° C. and quenched by slow (30 minutes addition of H$_2$O (7.2 mL, 0.4 mol), then the mixture was stirred at 0° C. (1 h). Solid was removed by filtration washed with ether, then the combined ether solution was dried (Na$_2$SO$_4$) and taken to dryness, yielding 9 as an oil[70] (9.36 g, 100%). $^1$H NMR (CDCl$_3$) δ 8.08 (1H, dd, J=2.4, 7.4 Hz), 7.88 (1H, m), 7.74 (1H, d, J=7.6 Hz), 7.34~7.57 (4H, m), 3.76 (2H, t, J=6.4 Hz), 3.20 (2H, t, J=7.5 Hz), 2.05 (2H, m), 1.75 (1H, brs).

3-(Naphth-1-yl)propyl-1-azide (10)

To a solution of 9 (9.0 g, 48.4 mmol) in anhydrous CH$_2$Cl$_2$ (100 mL) were added MsCl (4.5 mL, 58.1 mmol) and triethylamine (10.1 mL, 72.6 mmol) under argon Ar at 0° C. The mixture was stirred first at 0° C. (2 h) then at room temperature (30 minutes) and then subjected to an aqueous extractive workup. The resulting organic layer was dried (Na$_2$SO$_4$) and taken to dryness to provide crude 10 (12.55 g, 98%). This was taken up in dry DMF (100 mL), stirred with sodium azide (3.78 g, 58.1 mmol) at 90° C. (3 h) then cooled to room temperature and poured into ice-water (200 mL). The mixture was extracted with dichlorometlhane (3×50 mL), washed with brine (100 mL), dried (Na$_2$SO$_4$) and taken to dryness. The residue was purified by a silica gel chromatography using a the mixture of hexanes and ethyl acetate (20:1, v/v) to afford 10 as a clear oil (8.38 g, 82% based on the alcohol 9). $^1$H NMR (CDCl$_3$) δ 8.04 (1H, dd, J=1.5, 7.8 Hz), 7.88 (1H, dd, J=2.2, 7.4 Hz), 7.76 (1H, d, J=8.0 Hz), 7.33~7.58 (4H, m), 3.39 (2H, t, J=6.7 Hz), 3.19 (2H, t, J=7.4 Hz), 2.06 (2H, m).

3-(Naphth-1-yl)propylamine (11)

To a solution of 10 (1.19 g, 5.63 mmol) in anhydrous ether (20 mL) was added a solution of LiAlH$_4$ in THF (1M, 6 mL, 6 mrnol) under argon at 0° C. The reaction mixture was stirred at room temperature (1h), quenched at 0° C. by addition of 1N aqueous NaOH (0.86 mL), then stirred (1 h; 0° C.) and filtered through a pad of celite. The filtrate was dried (Na$_2$SO$_4$) and taken to dryness to provide 11 as a clear oil (1.04 g, 100%).[54] $^1$H NMR (DMSO) δ 8.09 (1H, dd, J=2.0, 7.3 Hz), 7.90 (1H, dd, J=2.4, 7.0 Hz), 7.75 (1H, d, J=7.8 Hz), 7.34~7.57 (4H, m), 3.06 (2H, t, J=7.8 Hz), 2.62 (2H, t, J=6.9 Hz), 1.72 (2H, tt, J=6.9, 8.0 Hz), 1.50 (2H, brs).

3-(Naphth-1-yl)propanamido-N-((tert-butoxy) carbonyl)-L-asparagine (12a)

Freshly prepared amine 11 (525 mg, 2.84 mmol) and N-Boc-L-Asn N-hydroxysuccinimide ester (935 mg, 2.84 mmol) in anhydrous dimethoxyethane (10 mL) were stirred at room temperature. The reaction mixture solidified after 10 minutes and was allowed to stand (1 h) then treated with cold H$_2$O (30 mL). The resulting white solid was collected by filtration, washed with H$_2$O (5×10 mL) and dried in vacuo to provide 12a in a quantitative yield. $^1$H NMR (DMSO) δ 8.12 (1H, d, J=7.3 Hz), 7.94 (2H, m), 7.80 (1H, d, J=7.3 Hz), 7.43~7.62 (4H, m), 7.32 (1H, s), 6.93 (2H, m), 4.26 (1H, dt, J=7.1, 6.9 Hz), 3.20 (2H, dt, J=6.3, 6.1 Hz), 3.07 (2H, t, J=7.5 Hz), 2.45 (2H, m), 1.83 (2H, tt, J=7.3, 7.1 Hz), 1.41 (9H, s) FABMS (+Vesbly) M/Z 400 (MH+).

Compound 14. A solution of 12a (398 mg, 1 mmol) in 10% (v/v) TFA in dichloromethane (11 mL) was stirred at room temperature (overnight) then solvent was removed and residue dried under vacuum to give crude amine 12b as its TFA salt. An active ester solution prepared by stirring N-Boc-1-amino-1-cyclohexanecarboxylic acid 13 (243 mg, 1 mmol), HOBT.H$_2$O(153 mg, 1 mmol) and dicyclohexylcarbodiimide (DCC) (240 mg, 1.15 mmol) in anhydrous DMF (3 mL) at room temperature (30 minutes), was added to a solution of 12a.TFA and diisopropylethylamine (DIPEA) (0.348 mL, 2 mmol) in DMF (2 mL) and the reaction mixture stirred at room temperature (overnight). Solvent was removed under high vacuum and the residue was chromatographied over silica gel using first EtOAc: CHCl$_3$ (1:10) then MeOH: CHCl$_3$ (1:10) to provide 14a as a white foam (353 mg, 67% based on 12a). $^1$H NMR (DMSO) δ 8.08 (2H, m), 7.90 (1H, m), 7.75 (1H, m), 7.62 (1H, m), 7.50 (2H, m), 7.39 (3H, m), 7.27 (1H, s), 6.92 (1H, s), 4.38 (1H, m), 3.45 (1H, m), 3.24 (1H, m), 3.03 (3H, t, J=6.7 Hz), 2.73 (1:2.44 (1H, dd, J=5.1, 16.1 Hz), 1.69~2.05 (6H, m), 1.40~1.65 (6H, m), 1.34 (9H, s). FABMS (+VE, Gly) m/z 525 (MH$^+$).

General procedure for the synthesis of compounds 16a, d–f. To a solution of 14b (106 mg, 0.25 mmol) [obtained after partition of 14b. TFA between aqueous NaHCO$_3$ and EtOAc: FABMS (+VE, Gly) m/z 425 [M+H]$^+$, HRMS calcd. for C$_{24}$H$_{33}$N$_4$O$_3$ m/z 425.425.25527 [M+H]$^+$, found 425.2557] in anhydrous DMF (1 mL) was added an active ester solution formed by reacting appropriately protected pTyr mimetics 15a, 15d,[55] 15e[56] or 15f,[56] (0. 3 mmol), HOBT.H$_2$O (41 mg, 0.3 mmol) and DIPCDI (47 μL, 0.3 mmol) in anhydrous DMF (0.5 mL) at room temperature (10 minutes). The combined reaction mixture was then stirred at room temperature overnight. Solvent was removed under high vacuum and residue was purified by silica gel chromatography (EtOAc in CHCl$_3$) to provide products as white foams: Compound 16a (90% yield); FABMS (+VE, NBA) m/z 866 (MH$^+$): 16d (69% yield) [an unresolved mixture of diastereomers, epimeric at the Pmp α-carbon]; FABMS (+VE, NBA), m/z 982.9 (MH$^+$): Compound 16e (79% yield); FABMS (+VE, NBA), m/z 1054.6 (MH$^+$): Compound 16f (79% yield); FABMS (+VE, NBA), m/z 106.3 (MH$^+$)

General procedure for conversion of compounds 16a,d–f to their N-Acetyl derivatives 17a,d–f, respectively. To solutions of 16a,d–f (01–0.2 mmol) in anhydrous MeCN (2.0 mL) was added piperidine (4 equivalents) and the solutions were stirred at room temperature (1 h). Solvent and excess piperidine were removed under high vacuum then residues were taken up in anhydrous MeCN and treated with N-acetylimidazole (4 equivalents) at room temperature. After all amine had reacted (from 3 h to 24 h) solvent was removed and residues were purified by silica gel chromatography (EtoAc in CHCl$_3$) to provide pure products as resins in quantitative yield, except where noted: Compound 17a FABMS (+VE, Gly) m/z 686 [M+H]+, HRMS calcd for C$_{39}$H,52N$_5$O$_6$ m/z 686.3918 [M+H]$^+$, found 686.3882: Compound L-17d (faster, "L"-diastereomer 29% yield)[63] HRMS m/z; D-17d (slower "D" diastereomer, 18% yield)[63] HRMS m/z: Compound 17e FABMS (+VE, NBA), m/z 874.6 (MH$^+$); Compounds 17f HRMS FABMS (+VE, NBA), m/z 888.5 (MH).

Compound 17b. A solution of 14a (168 mg, 0.320 mmol) in 20% (v/v) TFA in dichloromethane (3.6 mL) was stirred at room temperature (overnight), then solvent was removed and residue was dried under to give crude 14b.TFA as a syrup. An active ester solution formed by reacting N-Ac-L-Tyr((tert-BuO)$_2$PO)-OH (146 mg, 0.352 mmol), HOBT.H$_2$O (54 mg, 0.352 mmol) and DCC (73 mg, 0.352 mmol) in DMF (1 mL) (20 minutes) was added to a solution 14b.TFA and DIPEA (0.113 mL, 0.64 mmol) in DMF (2 mL) and the reaction mixture was stirred at room temperature (7 h). Solvent was removed under high vacuum and the residue was chromatographied on silica gel, eluenting with MeOH: CHCl$_3$ (1:40, 1:20 then 1:20) to provide L-17b[74] as a white foam (60.4 mg). Also obtained was the diasteriomer D-17b[74] (29 mg) resulting from partial racemization at the tyrosyl α-carbon. Additionally, an unseparated mixture of L-17b and D-17b (79.2 mg) was collected, providing a 64% combined yield of tyrosyl-coupled product. L-17b $^1$H NMR (DMSO) δ 8.22 (2H, m), 8.10 (1H, m), 7.97 (1H, d, J=8.1 Hz), 7.89 (1H, m), 7.74 (1H, m), 7.49 (3H, m), 7.37 (3H, m), 7.21 (2H, d, J=8.5 Hz), 7.03 (2H, d, J=8.3 Hz), 6.90 (1H, s), 4.60 (1H, m), 4.35 (1H, m), 3.16 (2H, m), 3.03 (4H, m), 2.73 (1H, t, J=11.4 Hz),2.59 (1H dd, J=6.6, 11.9 Hz), 1.75 (3H, s), 1.43 (18H, s), 1.17~2.05 (12H, brm). FABMS (+VE, NBA) m/z 822 (MH$^+$). D-17b $^1$HNMR (DMSO) δ 8.49 (1H, s), 8.45 (1H, d, J=5.4 Hz), 8.09 (1H, m), 7.90 (1H, m), 7.76 (1H, t, J=4.6 Hz), 7.65 (1H, d, J=8.1 Hz), 7.27~7.52 (8H, m), 7.06 (2H, d, J=8.3 Hz), 6.87 (1H, s), 4.57 (1H, m), 4.42 (1H, dt, J=5.1, 9.3 Hz), 3.28 (1H, m), 3.05 (3H, m), 2.87 (2H, m), 2.59 (2H, m), 1.77 (3H, s), 1.43 (18H, s), 1.15~2.00 (12H, brm).

Compound 17c. To a solution of amine 14b (106 mg, 0.25 mmol) in DMF (1 mL) was added an activated ester solution formed by reacting L-N-Boc-F2Pmp(OEt)2-OH (15c)[40] (135 mg, 0.30 mmol), HOBT.H$_2$O (46 mg, 0.30 mmol) and DIPCDI (47 μL, 0.30 mmol) in DMF (1.0 mL) (20 minutes) and the combined solution stirred at room temperature (overnight). DMF was removed under high vacuum and residue was chromatographied on silica gel (CHCl$_3$—MeOH, 25:1) to provide the Boc-protected dipeptide as a white foam (197 mg, 92%). $^1$HNMR (DMSO, 250 MHz): 8.20 (1H, s), 8.00~8.15 (2H, m), 7.90 (1H, m), 7.73 (1H, m), 7.36~7.50 (10H, m), 7.21 (1H, d, J=7.3 Hz), 6.91 (1H, s), 4.36 (2H, m), 4.10 (4H, m), 3.38~3.50 (2H, m), 3.17 (2H, m), 3.04 (2H, t, J=7.8 Hz), 2.66 (2H, m), 1.35~2.10 (12H, m), 1.30 (9H, s), 1.21 (3H, t, J=7.1 Hz), 1.20 (3H, t, J=7.1 Hz) ppm. A portion of this material (130 mg, 0.152 mmol) in dichloromethane (1 mL) with TFA (1 mL) was stirred at rt (1 h), then solvent was removed. The resulting foam was dissloved in DMF (1 mL) containing triethylamine (46 μL, 0.334 mmol) and 1-acetylimidazole (25 mg, 0.230 mmol) and the mixture was stirred at rt (2 hr) then concentrated. Chromatographic purification of the residue on silica gel (CHCl$_3$—MeOH, 15:1) provided 17c as a white foam (122 mg, 100%). $^1$H NMR (DMSO) δ 8.25 (1H, m), 7.87~8.13 (4H, m), 7.74 (1H, t, J=4.9 Hz), 7.36~7.53 (10H, m), 6.91 (1H, S), 4.70 (1H, m), 4.36 (1H, m), 6.91 (1H, s), 4.70 (1H, m), 4.36 (1H, m), 4.09 (4H, m), 3.41~3.52 (2H, m), 3.16 (2H, m), 3.04 (2H, t, J=8.0 Hz), 2.56~2.63 (2H, m), 1.74 (3H, s), 1.20 (6H, t, J=7.1 Hz), 1.15~2.01 (12H, m) ppm.

Final product 18a. A solution of 17a (0.21 mmol) in TFA (1.9 mL) with H$_2$O (0.1 mL) and triethylsilane (50 pL) was stirred at room temperature (1 h) then taken to dryness and purified by HPLC using a Prep NovaPak HR C$_{18}$ 6μ radial compression cartridge (200 mm×40 mm dia.) with a flow rate of 50 mL/min. and a linear gradient from 10% B to 50% B over 20 minutes; solvent A: 0.1% aqueous TFA aqueous; solvent B: 0.1% TFA in MeCN. Product 18a was obtained as a white solid (118 mg, 88% yield). ~H NMR (DMSO) ~8.2 (3H, m), 7.95 (2H, m), 7.8 (1H, m), 7.55 (3H, m), 7.42 (3H, m), 7.07 (2H, d, J=7.5 Hz), 6.94 (1H, bs), 6.67 (sH, d, J=7.5 Hz), 4.6 (1H, m), 4.4 (1H, m), 3.3~2.9 (SH, m), 2.75~2.50 (3H, m), 1.81 (3H,s), 2.05~1.10(12H,m). FABMS (+VE, 6 μg M(Z 630(MH$^+$). HRMS C$_9$/cd for C$_{35}$H$_{44}$N$_5$O$_6$ 630.3292 (MHF found 630.3339.

Compound 18b: A solution of L-17b (48.7 mg, 0.59 mmol), thioanisole (0.100 mL), TFA (0.5 mL) and dichloromethane (0.5 mL) was stirred at room temperature (overnight), then solvent was evaporated and the residue was dried under vacuum. The crude product was dissolved in MeCN:water (1:1, 2 mL), filtered and purified by HPLC, using a Vydac $C_{18}$ column (250 mm×20 mm dia.) with a flow rate: 20 mL/min and a linear gradient from 10% TFA in MeCN. Product 18b was obtained as a white solid (26 mg, 62%). $^1$H NMR (DMSO) δ 8.22 (2H, m), 8.07 (1H, m), 7.91 (2H, m), 7.74 (1H, m), 7.36~7.53 (6H,m), 7.17 (2H, d,J=8.3 Hz), 7.03 (2H, dJ=8.3 Hz), 6.90 (1H, s), 4.64 (1H, m), 4.35 91H,m), 3.17 (3H, m), 2.72 (1H, m), 2.59 (1H,m), 1.76(3H, s), 1.13~2.07 (12H,m). FABMS (-VE, 6 μg) m/z 708 [M–H]. HRFADMS $C_9$/cd for $C_{35}H_{43}N_5O_9P$ 736.2798 (M–H), found 736.2803.

Compound 18c. A mixture of 17c (70 mg, 0.088 mmol), TFA (1.2 mL), thioanisole (140 μL, 1.2 mmol), TMSBr (155 μL, 1.2 mmol), m-cresol (92 μL, 0.876 mmol) was stirred at rt (24 h) then the mixture was concentrated under argon and treated with cold ether-hexane (1:1; 7 mL) to provide a percipitate. Supernatant was removed following centrifugation, and solid was washed three times by resuspension and centrifugation. The resulting solid was purified by HPLC as indicated for the purification of 18a using a linear gradient from 5% B to 50% B over 25 minutes to provide 18c as a white solid (43 mg, 66% yield). $^1$H NMR (DMSO) δ 8.29 (1H, d, j=7.4 Hz), 8.25 (1H, s), 8.09 (1H, t, j=6.1 Hz), 7.99 (1H, d, j=8.1 Hz), 7.89 (1H, dt, j=1.9, 5.4 Hz), 7.74 (1H, t, j=4.6 Hz), 7.33~7.54 (10H, m), 6.91 (1H, s), 4.65 (1H, m), 4.33 (1H, q, j=6.6Hz), 3.17 (2H, m), 3.04 (3H, m), 2.81 (1H, dd, j=13.8, 10.7 Hz), 2.65 (1H, dd, j=6.3, 15.1 Hz), 3.17 (2H, m), 3.04 (3H, m), 2.81 (1H, dd, j=13.8, 10.7 Hz), 2.65 (1H, dd, j=6.3, 15.1 Hz), 2.56 (1H, dd, j=4.9, 15.1 Hz), 1.77 (3H, s), 1.10~2.05 (12H, m) ppm. FABMS (–VE, 6 μg, m/z): 742 [(M–H)].

Final Product L-18d. Treatment of L-17d (0.035 mmol) as described above for the preparation of 18a and HPLC purification of crude product as described therein, provided L-18d as a white solid (17 mg, 69% yield). [74] $^1$H NMR (DMSO, $D_2O$) δ 8.23 (1H, m), 8.11 (1H, m),7.94 (1H, m),7.78 (1H, m), 7.42 (2H,m), 7.18 (3H, bs), 4.64 (1H, m), 4.40 (1H, m), 3.21 (2H, m), 3.07 (3H, m), 2.96 (2H, d, j=21.4 Hz), 2.85~2.55 (4H, m), 2.1~1.1 (12H,m), 1.80 (3H, s). HRMS (–VE, 6 μg)m/z, 706 (M–H)⁻ HRMS for $C_{36}H_{45}N_5O_8P$ 706.3006 (M–H)⁻, for 706.296.

Final Product d-18d. Treatment of d-17d (0.035 mmol) as described above and HPLC purification of crude product as described therein, provided D-18d as a white solid (14 mg,84% yield). [71] $^1$H NMR (DMSO, $D_2O$) δ 8.53 (1H, bs), 8.14 (1H, m), 7.94 (1H, m), 7.78 (1H, m) 7.55 (2H,m), 7.45 (2H, m), 7.20 (3H,m), 4.59 (1H, m), 4.45 (1H,m), 7.94(1H, m), 7.78 (1H, m), 7.55 (2H,m), 7.45 (2H, m), 7.20 (3H,m), 4.59 (1H,m), 7.78 (1H,m) 7.55 (2H,m), 7.45 (2H, m), 7.20 (3H,m), 4.59 (1H,m), 2.18~1.0 (12H,m), 1.80 (3H,s). FABMS (–VE, 6 μg)m/z 706 (M–H)⁻. HRMS $C_9$/cd for $C_{36}H_{45}N_5O_9P$ 706.3006 (m–H), found 706 3057.

Final product 18f. A solution of 17f (0.075 mmol) and tetrabutylammonium fluoride (TBAF), 1.0 M in THF (300 μL) in anhydrous DMF (2 mL) was stirred at room temperature (overnight) then taken to dryness and purified by HPLC using a Prep NovaPak HR $C_{18}$6 μ radial compression cartridge (200 mm×40 mm dia.) as described above for 18a and 18e to provide 18f as its mono TBAF salt (36 mg) and di-TBAF salt (17 mg). A portion (16 mg) of mono-TBAF salt was repurified by HPLC to provide 18f as its free diacid (11 mg). $^1$H NMR (DMSO) δ 8.29 (1H, s), 8.12 (1H, m), 7.94 (1H, m), 7.77 (1H, m), 7.68 (1H, s), 7.52 (2H, m, 7.45~7.33 (2H, m), 6.91 (1H, d, j=8.5 Hz), 4.78 (1H,s), 4.64 (1H, m), 4.40 (1H,m), 3.22 (2H,m), 3.1~3.0 (3H, m), 2.8~2.5 (4H,m), 2.55 (3H,s), 2.05~1.1 (12H,m), FABMS (–VE, Gly)m/z 730[M–H]⁻, 672 [M–$CH_2CO_2H$]⁻, HRMS calcd for $C_{38}H_{44}N_5O_{10}$ m/z 730.3088182 [M–H]⁻, found 730.2997.

Compound 19d. A mixture of diastereomers epimeric at the Pmp α-carbon, 16d (150 mg, 0.15 mmol) was treated with peperidine (48 μL, 0.45 mmol) in acentonitrile (2 mL) at rt 92 h) then solvent was removed, residue was dried under high vacuum, then dissolved in DMF (1 mL) containing DIEA (44 μL, 025 mmol) and tert-butyl oxalyl chloride (0.23 mmol) (prepared by reaction of oxalyl chloride with tert-butyl alcohol). After 10 minutes the reaction mixture was concentrated and purified by on silica gel chromatography ($CHCl_3$-MeOH, from 30:1 to 20:1) to provide the single diastereomer 19d (59.4 mg, 44%) [assignment of L-Pmp configuration was based on analogy to the N-actyl compound L-17d]. $^1$H NMR (DMSO) δ 8.69 (1H, d, J=8.1 Hz), 8.32 (1H, s) 7.97 (1H, d, J=7.8 Hz), 7.89 (1H, m), 7.74 (1H, t, J=4.8 Hz), 7.49 (3H,m), 7.38 (3H, m), 7.16 (4H, m), 6.92 (1H, s) 4.63 (1H, m) 4.38 (1H, m), 2.85~3.25 (8H, m), 2.67 (1H, dd, J=6.8, 15.9 Hz), 2.55 (1H, dd J=5.4, 15.9 Hz, partially covered by DMSO peaks), 1.06~2.05 (12H, m), 1.41 (9H, s), 1.31 (18H, s).

Compound 19f. A solution of 16f 988 mg, 0.082 mmol) in anhydrous MeCN (2 mL) with piperidine (27 μL, 0.33 mmol) was stirred at room temperature (1 h) then taken to dryness and placed under high vacuum. Residue was dissolved in anydrous DMF (0.5 mL) and treated overnight with an activated ester solution formed by stirring (10 minutes) oxalic acid mono tert-butyl ester (24 mg, 016 mmol), $HOBT.H_2O$ (22 mg, 0.16 mmol) and DIPCDI (26 μL, 0.16 mmol) in anhydrous DMF (0.5 mL). Solvent was removed under high vacuum and residue purified by silica gel chromatography (MeOH in EtOAc) to provide 19f as a syrup (45 mg, 56% yield). $^1$H NMR ($CDCl_3$) δ 8.13 (2H, m), 7.98 (1H, m), 7.80~7.69 (2H, m), 7.60~7.27 (4H, m), 6.80 (2H, m), 6.42 (1H, bs), 5.78 (1H, bs), 4.80~4.66 (3H m), 4.62 (2H, s), 4.50~4.40 (3H, m), 3.50~3.35 (2H, m), 3.50~3.00 (6H, m), 2.15~1.15 (14H, m), 1.56 (18H, s), 0.14 (9H, s). FABMS (⁺VE, NBA) m/2 97S.2 (mH⁺).

Final Product 20d. S solution of 19d (45 mg, 0.0497 mmol) in dichloromethane (0.5 mL) with TFA (0.5 mL) and triethylsilane (20 μL) was stirred at rt (2 h) then the mixture was concentrated dried under vacuum. Residue was purified by HPLC using an Advantage $C_{18}$5 μm column (20 mm dia. ×250 mm) with a binary solvent mixture of A (0.1% aqueous TFA) and B (0.1% TFA in MeCN) and a linear gradient over 25 minutes from B=5% to B=60%. Final product 20d was obtained as a white solid (31 mg, 84%). $^1$H NMR (DMSO) δ 8.77 (1H, d,j=8.1 Hz), 8.32 (1H, s), 8.08 (1H,m), 7.97 (1H, d,j=8.1 Hz), 7.91 (1H,m), 7.75 (1H,m), 7.50 (3H,m), 7.14 (4H, m), 6.91 (1H,s), 4.68 (1H,m), 7.75 (1H,m), 7.50 (3H,m), 7.14 (4H,m), 6.91 (1H,s), 4.68 (1H,m), 4.37 (1H, m), 3.1 (3H,m), 3.03 (3H,m), 2.89 (2H,d,j=21.2 Hz), 2.68 (1H,m),4.37 (1H,m), 3.16 (3H,m), 3.03 (3H,m), 2.89 (2H, d,j=21.2 Hz), 2.68 (1H,dd,j=6.3, 14.6 Hz), 2.53 (1H,dd,j= 4.9, 14.6 Hz), 1.15~2.05 (12H,m) ppm. (—COOH, and P(O) (OH)$_2$ did not show). FBMS (–VE, 6 μg)m/z 731 M–H). HKMS $c_9$/cd for $C_{36}H_{43}N_5O_{10}P$ 736.2748(M–H), found 736.2.

Final Product 20f. A solution of 19f (37 mg, 0038 mmol) in MeCN (1.0 mL) with 1.0 MTBAF in THF (0.12 mmol) was stirred at room temperature (2 days) then solvent was removed and the residue was dried under vacuum. The resulting material was dissolved in a mixture of TFA (950 μL), $H_2O$ (50 μL) and triethylsilane (25 μL) and stirred at room temperature (3 h), then taken to near dryness. Treatment with cold ether gave crude product as a white solid, which was dried under an argon stream and purified twice by HPLC as described above for the purification of 18f, providing 20f as a white solid (17 mg, 58%). $^1$H NMR (DMSO) δ 8.79 (1H,d,j=8.1 Hz), 8.4 (1H,s), 8.06 (1H,m), 7.98 (1H,d,j=7.5 Hz), 7.87 (1H,m), 7.76 (1H, m), 7.76 (1H,m), 7.68 (1H,d,j=1.7 Hz), 7.29~7.55 (7H,m), 6.91 (2H,m), 4.72 (3H,m), 4.36 (1H,m), 2.90~3.26 (6H,m), 2.67 (2H,m), 1.14~2.05 (12H,m). FABMS (−VE 6 μg m/z 760 ([M−H]$^-$.

REFERENCES

1. Ponzetto, C. *Protein Modules in Signal Transduction* 1998, 228, 165–177.
2. Dankort, D. L.; Wang, Z. X.; Blackmore, v.; Moran; M. F.; Muller; W. *J. Mol. Cell. Biol.* 1997, 17, 5410–5425.
3. Furet, P.; Gay, B.; Garcia Echeverria, C.; Rahuel, J.; Fretz, H.; Schoepfer, J.; Caravatti, G. *J. Med. Chem.* 1997, 40, 3551–3556.
4. Rahuel, J., Garcia-Echeverria, C.; Furet, P.; Strauss, A.; Caravatti, G.; Fretz, H.; Schoepfer, J.; Gay, B. *J. Mol. biol.* 1998, 279, 1013–1022.
5. Garcia-Echeverria, C.; Furet, P.; Gay, B.; Fretz, H.; Rahuel, P.; Schoepfer, J.; Caravatti, G. *J. Med. Chem.* 1998, 41, 1741–1744.
6. Furet, P.; Gay, B.; Caravatti, G.; Garcia-Escheverria, C.; Rahuel, J.; Schoepfer, J.; Fretz, H. *J. Med. Chem.* 1998, 41, 3442–3449.
7. Rahuel, J.; Gay, B.; Erdmann, D.; Strauss, A.; Garcia-Exheverria, C.; Furet, P.; Caravatti, G.; Fretz, H.; Schoepfer, J.; Grutterf, M. G. *Nature Struct. Biology* 996, 3, 586–589.
8. Burke, T. R., Jr.; Yao, Z. -J.; Smyth, M. S.; Ye, B. *Curr. Pharmaceut. Design* 1997, 3, 291–304.
9. Miller, M. J.; Anderson, K. S.; Braccolino, D. S.; Cleary, D. G.; Gruys, K. J.; Han, C. Y.; Lin, K. -C.; Pansegrau, P. D.; Ream, J. E.; Sammons, R. D.; Silkorski, J. A. *Bioorg. Med. Chem. Lett.* 1993, 7, 1435–1440.
10. Ye, B.; Burke, T. R., Jr. *Tetrahedron Lett.* 1995, 36, 4733–4736.
11. Burke, T. R., Jr.; Ye, B.; Akamatsu, M.; ford, H.; Yan, X. J.; Kole, H. K.; Wolf, G.; Shoelson, S. E.; Roller, P. P. *J. Med. Chem.* 1996, 39, 1021–1027.
12. Kuriyan, J.; Cowburn, D. Modular peptide recognition domains in eukaryotic signaling. *Ann. Rev. Biophys. Biomol. Struct.* 1997, 26, 259–288.
13. Mayer, B. J.; Gupta, R. Functions of SH2 and SH3 domains. *Protein Modules in Signal Transduction* 1998, 228, 1–22.
14. Panayotou, G.; Waterfield, M. D. The assembly of signalling complexes by receptor tyrosine kinases. *Bioessays* 1993, 15, 171–177.
15. Levitzki, A. Targeting signal transduction for disease therapy. *Curr. Opin. Cell. Biol.* 1996, 8, 239–244.
16. Burke, T. R., Jr.; Yao, Z. -J.; Smyth, M. S.; Ye, B. Phosphotyrosyl-based motifs in the structure-based design of protein-tyrosine kinase-dependent signal transduction inhibitors. *Curr. Pharm. Design* 1997, 3, 291–304.
17. Boutin, J. A. Tyrosine protein kinase inhibition and cancer. *Int. J. Biochem.* 1994, 26, 1203–1226.
18. Levitzki, A.; Gazit, A. Tyrosine kinase inhibition: An approach to drug development. *Science* 1995, 267, 1782–1788.
19. Lawrence, D. S.; Niu, J. K. Protein kinase inhibitors: The tyrosine-specific protein kineses. *Pharmacol. Ther.* 1998, 77, 81–114.
20. Burke, T. R., Jr.; Zhang, Z. -Y. Protein-tyrosine phosphatases: Structure, mechanism and inhibitor discovery. *Protein Science* (in press).
21. Saltiel, A. R.; Sawyer, T. K. Targeting signal transduction in the discovery of antiproliferative drugs. *Chem. Biol.* 1996, 3, 887–893.
22. Shoelson, S. E. SH2 and PTB domain interactions in tyrosine kinase signal transduction. *Curr. Opin. Chem. Biol.* 1997, 1, 227–234.
23. Waksman, G.; Kominos, D.; Robertson, S. C.; Pant, N.; Baltimore, D.; Birge, R. B.; Cowburn, D.; Hanafusa, H.; Mayer, B. J.; Overduin, M.; Resh, M. D.; Rios, C. B.; Silverman, L.; Kuriyan, J. Crystal structure of the phosphotyrosine recognition domain SH2 of v-src complexed with tyrosine-phosphorylated peptides. *Nature* 1992, 358, 646–653.
24. Waksman, G.; Shoelson, S. E.; Pant, N.; Cowburn, D.; Kuriyan, J. Binding of a high affinity phosphotyrosyl peptide to the Src Sh2 domain—Crystal structures of the complexed and peptide-free forms. *Cell* 1993, 72, 779–790.
25. Mikol, V.; Baumann, G.; Keller, T. H.; Manning, U.; Zurini, M. G. M. The crystal structures of the SH2 domain of p56(lck) complexed with two phosphonopeptides suggest a gated peptide binding site. *J. Mol. Biol.* 1995, 246, 344–355.
26. Hatada, M. H.; Lu, X. D.; Laird, E. R.; Green, J.; Morgenstern, J. P.; Lou, M. Z.; Marr, C. S.; Phillips, T. B.; Ram, M. K.; Theriault, K.; Zoller, M. J.; Karas, J. L. Molecular basis for interaction of the protein tyrosine kinase ZAP-70 with the T-cell receptor. *Nature* 1995, 377, 32–38.
27. Zhou, M. M.; Meadows, R. P.; Logan, T. M.; Yoon, H. S.; Wade, W. S.; Ravichandran, K. S.; Burakoff, S. J.; Fesik, S. W. Solution structure of the Shc SH2 domain completed with a tyrosine-phosphorylated peptide from the T-cell receptor. *Proc. Natl. Acad. Sci. USA* 1995, 92, 7784–7788.
28. Narula, S. S.; Yuan, R. W.; Adams, S. E.; Green, O. M.; Green, J.; Philips, T. B.; Zydowsky, L. D.; Botfield, M. C.; Hatada, M.; Laird, E. R.; Zoller, M. J.; Karas, J. L.; Dalgarno, D. C. Solution structure of the C-terminal SH2 domain of the human tyrosine kinase Syk complexed with a phosphotyrosine pentapeptide. *Structure* 1995, 3, 1061–1073.
29. Xu, R. X.; Word, J. M.; Davis, D. G.; Rink, M. J.; Willard, D. H.; Gampe, R. T. Solution structure of the human pp60(c-src) SH2 domain complexed with a phosphorylated tyrosine pentapeptide. *Biochemistry* 1995, 34, 2107–2121.
30. Rahuel, J.; Gay, B.; Erdmann, D.; Strauss, A.; GarciaEcheverria, C.; Furet, P.; Caravatti, G.; Fretz, H.; Schoepfer, J.; Grutter, M. G. Structural basis for specificity of GRB2-SH2 revealed by a novel ligand binding mode. *Nature Struct Biology* 1996, 3, 586–589.
31. Tong, L.; Warren, T. C.; King, J.; Betageri, R.; Rose, J.; Jakes, S. Crystal structures of the human p56(lck) SH2 domain in complex with two short phosphotyrosyl peptides at 1.0 angstrom and 1.8 angstrom resolution. *J. Mol. Biol.* 1996, 256, 601–610.
32. Sicheri, F.; Moarefi, I.; Kuriyan, J. Crystal structure of the Src family tyrosine kinase Hck. *Nature* 1997, 385, 602–609.
33. Chen, X.; Uwe, V.; Zhao, Y.; Jeruzalmi, D.; Darnell, J. E., Jr.; Kuriyan, J. Crysta' structure of a tyrosine phosphorylated STAT-1 dimer bound to DNA. *Cell* 1998, 93, 827839.

34. Zhou, S. Y.; Cantley, L. C. Recognition and specificity in protein tyrosine kinasemediated signalling. *Trends Biochem. Sci.* 1995, 20, 470–475.
35. Lunney, E. A.; Para, K. S.; Rubin, J. R.; Humblet, C.; Fergus, J. H.; Marks, J. S.; Sawyer, T. K. Structure-based design of a novel series of nonpeptide ligands that bind to the pp60 (src) SH2 domain. *J. Am. Chem. Soc.* 1997, 119, 12471–12476.
36. Pacofsky, G. J.; Lackey, K.; Alligood, K. J.; Berman, J.; Charifson, P. S.; Crosby, R. M.; Doresy, G. F., Jr.; Feldman, P. L.; Gilmer, T. M.; Hummel, C. W.; Jordan, S. R.; Mohr, C.; Shewchuk, L. M.; Sternbach, D. D.; Rodriguez, M. Potent dipeptide inhibitors of pp60c-src SH2 domain. *J. Med. Chem.* 1998, 41, 1894–1908.
37. Marseigne, I.; Roques, B. P. Synthesis of new amino acids mimeticking sulfated and phosphorylated tyrosine residues. *J. Org. Chem.* 1988, 53, 3621–3624.
38. Burke, T. R., Jr.; Smyth, M.; Nomizu, M.; Otaka, A.; Roller, P. P. Preparation of fluoroand hydroxy-4-phosphonomethyl-D,L-phenylalanine suitably protected for solid-phase synthesis of peptides containing hydrolytically stable analogues of O-phosphotyrosine. *J. Org. Chem.* 1993, 58, 1336–1340.
39. Burke, T. R.; Smyth, M. S.; Otaka, A.; Roller, P. P. Synthesis of 4phosphono(Difluoromethyl)-D,L-phenylalanine and N-Boc and N-Fmoc derivatives suitably protected for solid-phase synthesis of nonhydrolyzable phosphotyrosyl peptide analogues. *Tetrahedron Lett.* 1993, 34, 4125–4128.
40. Smyth, M. S.; Burke, T. R., Jr. Enantioselective synthesis of N-Boc and N-Fmoc protected diethyl 4-phosphonodifluoromethyl-L-phenylalanine; agents suitable for the solid-phase synthesis of peptides containing nonhydrolyzable analogues of O-phosphotyrosine. *Tetrahedron Lett.* 1994, 35, 551–554.
41. Domchek, S. M.; Auger, K. R.; Chatterjee, S.; Burke, T. R.; Shoelson, S. E. Inhibition of SH2 domain/phosphoprotein association by a nonhydrolyzable phosphonopeptide. *Biochemistry* 1992, 31, 9865–9870.
42. Burke, T. R., Jr.; Smyth, M. S.; Otaka, A.; Nomizu, M.; Roller, P. P.; Wolf, G.; Case, R.; Shoelson, S. E. Nonhydrolyzable phosphotyrosyl mimetics for the preparation of phosphatase-resistant SH2 domain inhibitors. *Biochemistry* 1994, 33, 6490–6494.
43. Xiao, S.; Rose, D. W.; Sasaoka, T.; Maegawa, H.; Burke, T. R.; Roller, P. P.; Shoelson, S. E.; Olefsky, J. M. Syp (SH-PTP2) is a positive mediator of growth factor stimulated mitogenic signal transduction. *J. Biol. Chem.* 1994, 269, 21244–21248.
44. Wange, R. L.; Isakov, N.; Burke, T. R., Jr.; Otaka, A.; Roller, P. P.; Watts, J. D.; Aebersold, R.; Samelson, L. W. F2(Pmp)2-TAM(zeta)3, a novel competitive inhibitor of the binding of ZAP-70 to the T cell antigen receptor, blocks early T cell signalling. *J. Biol. Chem.* 1995, 270, 944–948.
45. Rojas, M.; Yao, S. Y.: Lin, Y. Z. Controlling epidermal growth factor (EGF)-stimulated ras activation in intact cells by a cell-permeable peptide mimeticking phosphorylated EGF receptor. *J Biol Chem* 1996, 271, 27456–27461.
46. Williams, E. J.; Dunican, D. J.; Green, P. J.; Howell, F. V.; Derossi, D.; Walsh, F. S.; Doherty, P. Selective inhibition of growth factor-stimulated mitogenesis by a cell-permeable Grb2-binding peptide. *J. Biol. Chem.* 1997, 272, 22349–22354.
47. Stankovic, C. J.; Surendran, N.; Lunney, E. A.; Plummer, M. S.; Para, K. S.; Shahripour, A.; Fergus, J. H.; Marks, J. S.; Herrera, R.; Hubbell, S. E.; Humblet, C.; Saltiel, A. R.; Stewart, B. H.; Sawyer, T. K. The role of 4-phosphonodifluoromethyl and 4-phosphonophenylalanine in the selectivity and cellular uptake of SH2 domain ligands. *Bioorg. Med. Chem. Lett.* 1997, 7, 1909–1914.
48. Gilmer, T.; Rodriquez, M.; Jordan, S.; Crosby, R.; Alligood, K.; Green, M.; Kimery, M.; Wagner, C.; Kinder, D.; Charifson, P.; Hassell, A. M.; Willard, D.; Luther, M.; Rusnak, D.; Sternbach, D. D.; Mehrotra, M.; Peel, M.; Shampine, L.; Davis, R.; Robbins, J.; Patel, I. R.; Kassel, D.; Burkhart, W.; Moyer, M.; Bradshaw, T.; Berman, J. Peptide inhibitors of src SH3-SH2-phosphoprotein interactions. *J. Biol. Chem.* 1994, 269, 31711–31719.
49. Mehrotra, M. M.; Sternbach, D. D.; Rodriguez, M.; Charifson, P.; Berman, J. Alphadicarbonyls as "noncharged" arginine-directed affinity labels. Novel synthetic routes to alpha- dicarbonyl analogs of the pp60(c-src) SH2 domain-targeted phosphopeptide AcTyr(OPO3H2)-Glu-Glu-Ile-Glu. *Bioorg. Medl. Chem. Lett.* 1996, 6, 1941–1946.
50. Ye, B.; Akamatsu, M.; Shoelson, S. E.; Wolf, G.; Giorgetti-Peraldi, S.; Yan, X. J.; Roller, P. P.; Burke, T. R. L-O-(2-malonyl)tyrosine: A new phosphotyrosyl mimetic for the preparation of Src homology 2 domain inhibitory peptides. *J. Med. Chem.* 1995, 38, 4270–4275.
51. Burke, T. R.; Ye, B.; Akamatsu, M.; Ford, H.; Yan, X. J.; Kole, H. K.; Wolf, G.; Shoelson, S. E.; Roller, P. P. 4'-O-[2-(2-fluoromalonyl)]-L-tyrosine: A phosphotyrosyl mimetic for the preparation of signal transduction inhibitory peptides. *J. Med. Chem.* 1996, 39,1021–1027.
52. Margolis, B. The GRB family of SH2 domain proteins. *Prog. Biophys. Mol. Biol.* 1994, 62, 223–244.
53. Fretz, H.; Furet, P.; Schoepfer, J.; Garcia-Echeverria, C.; Gay, B.; Rahuel, J.; Caravatti, G. Targeting a hydrophobic patch on the survace of the Grb2-SH2 Domain Leads to highaffinity phosphotyrosine-containing peptide ligands. 15th American Peptide Symposium, Nashville, Tenn. Jun. 14–19, 1997 1997, Abstract P422.
54. Mndzhoyan; Tl., E. Arm. Khim Zh. 1969, 22, 795. J
55. Burke, T. R., Jr.; Russ, P.; Lim, B. Preparation of 4-[bis(tert-butyl)phosphonomethyl]-N-Fmoc-DL-phenylalanine; a hydrolytic al ly stable an alogue of O-phosphotyrosine potentially suitable for peptide synthesis. *Synthesis* 1991, 11, 1019–1020.
56. Burke, T. R., Jr.; Yao, Z. -J.; He, Z.; Milne, G. W. A.; Wu, L.; Zhang, Z. Y.; Voigt, J. H. Enantioselective synthesis of nonphosphorus-containing phosphotyrosyl mimetics and their use in the preparation of tyrosine phosphatase inhibitory peptides. *Tetrahedron* (in press).
57. Dankort, D. L.; Wang, Z. X.; Blackmore, V.; Moran, M. F.; Muller, W. J. Distinct tyrosine autophosphorylation sites negatively and positively modulate neu-mediated transformation. *Mol. Cell. Biol.* 1997, 17, 5410–5425.
58. Fixman, E. D.; HolgadoMadruga, M.; Nguyen, L.; Kamikura, D. M.; Fournier, T. M.; Wong, A. J.; Park, M. Efficient cellular transformation by the Met oncoprotein requires a functional Grb2 binding site and correlates with phosphorylation of the Grb2-associated proteins, Cbl and Gab 1. *J. Biol. Chem.* 1997, 272, 20167–20172.
59. Tari, A. M.; Arlinghaus, R.; LopezBerestein, G. Inhibition of Grb2 and Crkl proteins results in growth inhibition of Philadelphia chromosome positive leukemic cells. *Biochem. Biophys. Res. Commun.* 1997, 235, 383–388.
60. Ma, G. Z.; Lu, D.; Wu, Y.; Liu, J. X.; Arlinghaus, R. B. Bcr phosphorylated on tyrosine 177 binds Grb2. *Oncogene* 1997, 14, 2367–2372.

61. Di Fiore, P. P.; Pierce, J. H.; Fleming, T. P.; Hazan, R.; Ullrich, A.; King, C. R.; Schlessinger, J.; Aaronson, S. A. overexpression of the human EGF receptor confers an EGF-dependent transformed phenotype to NIH 3T3 cells. *Cell* 1987, 51, 1063–1070.
62. Hudziak, R. M.; Schlessinger, J.; Ullrich, A. *Proc. Natl. Acad. Sci. U.S.A.* 1987, 84, 7159–7163.
63. Ben-Levy, R.; Paterson, H. F.; Marshall, C. J.; Yarden, Y. A single autophosphorylation: site confers oncogenicity to the Neu/ErbB-2 receptor and enables coupling to the MAP kinase pathway. *Embo J.* 1994, 13, 3302–3311.
64. Xie, Y. M.; Pendergast, A. M.; Hung, M. C. Dominant-negative mutants of Grb2 induced: reversal of the transformed phenotypes caused by the point mutation-activated rat HER 2/Neu. *J. Biol. Chem.* 1995, 270, 30717–30724.
65. Maignan, S.; Guilloteau, J. P.; Fromage, N.: Arnoux, B.; Becquart, J.; Ducruix, A. Crystal structure of the mammalian Grb2 adaptor. *Science* 1995, 268, 291–293.
66. McNemar, C.; Snow, M. E.; Windsor, W. T.; Prongay, A.; Mui, P.; Zhang, R. M.; Durkin, J.; Le, H. V.; Weber, P. C. Thermodynamic and structural analysis of phosphotyrosine polypeptide binding to Grb2-SH2. *Biochemistry* 1997, 36, 10006–10014.
67. Ogura, K.; Tsuchiya, S.; Terasawa, H.; Yuzawa, S.; Hatanaka, H.; Mandiyan, V.; -Schlessinger, J.; Inagaki, F. Conformation of an Shc-derived phosphotyrosine-containing peptide complexed with the Grb2 SH2 domain. *J. Biomol. NMR* 1997, 10, 273–278.
68. Recent studies have shown that while most SH2 domains preferentially bind their ligands in linear fashions, D-bend orientations are acceptable alternatives. See reference 58.
69. Gay, B.; Furet, P.; GarciaEcheverria, C.; Rahuel, J.; Chene, P.; Fretz, H. Dual specificity of Src homology 2 domains for phosphotyrosine peptide ligands. *Biochemistry* 1997, 36, 5712–5718.
70. Furet, P.; Gay, B.; GarciaEcheverria, C.; Rahuel, J.; Fretz, H.; Schoepfer, J.; Caravatti, G. Discovery of 3-aminobenzyloxycarbonyl as an N-terminal group conferring high affinity to the minimal phosphopeptide sequence recognized by the Grb2-SH2 domain. *J. Med. Chem.* 1997, 40, 3551–3556.
71. Garcia-Echeverria, C.; Furet, P.; Gay, B.; Fretz, H.; Rahuel, P.; Schoepfer, J.; Caravatti, G. Potent antagonists of the SH2 domain of Grb2: Optimization of the X=1 position of 3-amino-Z-Tyr(PO3H2)-X+1-Asn-NH2. *J. Med. Chem.* 1998, 41, 1741–1744.
72. Morelock, M. M.; Ingraham, R. H.; Betageri, R.; Jakes, S. Determination of receptorligand kinetic and equilibrium binding constants using surface plasmon resonance: Application to the lck SH2 domain and phosphotyrosyl peptides. *J. Med. Chem.* 1995, 38, 1309–1318.
73. Oligino, L.; Lung, F. D. T.; Sastry, L.; Bigelow, J.; Cao, T.; Curran, M.; Burke, T. R.; Wang, S. M.; Krag, D.; Roller, P. P.; King, C. R. Nonphosphorylated peptide ligands for the Grb2 Src homology 2 domain. *J. Biol. Chem.* 1997, 272, 29046–29052.
74. Absolute configurations of the Pmp residues were not determined unambiguously, rater the L-configuration was assigned to the enantiomer illiciting the more potent inhibition.
75. Shahripour, A.; Plummer, M. S.; Lunney, E. A.; Para, K. S.; Stankovic, C. J.; Rubin, J. R.; Humblet, C.; Fergus, J. H.; Marks, J. S.; Herrera, R.; Hubbel, S. E.; Saltiel, A. R.; Sawyer, T. K. Novel phosphotyrosine mimetics in the design of peptide ligands for pp60src SH2 domain. *Bioorg. Med. Chem. Lett.* 1996, 6, 1209–1214.
76. Kraus, M. H.; Popescu, N. C.; Amsbough, S. C.; King, C. R. Overexpression of the EGF receptor-related proto-oncogene erbB-2 in human mammary tumor cell lines by different molecular mechanisms. *EMBO J.* 1987, 6, 605–610.
77. Rojas, M.; Yao, S. Y.; Donahue, J. P.; Lin, Y.Z. An alternative to phosphotyrosine-containing motifs for binding to an SH2 domain. *Biochem. Biophys. Res. Commun.* 1997, 234, 675–680.
78. Sastry, L.; Lin, W. H.; Wong, W. T.; Difiore, P. P.; Scoppa, C. A.; King, C. R. Quantitative analysis of Grb2-Sos1 interaction: The N-terminal SH3 domain of Grb2 mediates affinity. *Oncogene* 1995, 11, 1107–1112.
79. Allen, M. C.; Brundish, D. E.; Fullerton, J. D.; Wade, R. *J. Chem. Soc. Perkin I* 1986, 989–1004.
80. Sergiewskaja; Elina Zh. *Obshch. Khim* 1943, 13, 864–865.
81. Searles, S. *J. Amer. Chem. Soc.* 1951, 73, 124.

What is claimed is:

1. A compound of the formula I,

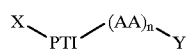

(I)

wherein n is 0 to 15,

X is oxalyl,

PTI is a bivalent radical of phosphotyrosine or of an amino acid selected from the group consisting of phosphonomethyl-phenylalanine, phosphono-(α-fluoro)methyl-phenylalanine, phosphono-(α,α-difluoro)methyl-phenylalanine, phosphono-(α-hydroxy)methyl-phenylalanine, O-sulfo-tyrosine, phosphonophenylalanine, dicarboxymethoxy-phenylalanine, aspartic acid, glutamic acid, phosphoserine and phosphothreonine, each of which is present in the (D,L)-, D- or L-form;

AA stands for a bivalent radical of a natural or unnatural amino acid, and

Y is a secondary amino group, or a salt thereof.

2. The compound of claim 1, wherein n is 1 to 15.

3. The compound of claim 1 wherein n is 1 to 4;

PTI is a bivalent radical of phosphotyrosine or of an amino acid selected from the group consisting of phosphonomethyl-phenylalanine, phosphono-(α-fluoro)methyl-phenylalanine, phosphono-(α,α-difluoro)methyl-phenylalanine, phosphono-(α-hydroxy)methyl-phenylalanine, O-sulfo-tyrosine, dicarboxymethoxy-phenylalanine, aspartic acid, glutamic acid, phosphoserine and phosphothreonine, each of which is present in the (D,L)-, D- or L-form;

—(AA)$_n$— is a bivalent radical of a tripeptide of the formula -(AA$^1$)-(AA$^2$)-(AA$^3$)- wherein -(AA$^1$)- is selected from the group consisting of -Ile-, -Ac$_5$c-, -Ac$_6$c-, -Asp-, -Gly-, -Phe-, -Ac$_7$c-, -Nbo-, -Met-, -Pro-, -β-Ala-, -Gln-, -Glu-, -DHph-, -HPh- and -tLe-; -(AA$^2$)- is selected from the group consisting of -Asn-, -β-Ala-, -Gly-, -Ile-, and -Gln-; and -(AA$^3$)- is selected from the group consisting of -Val-, -β-Ala-, -Gly-, -Gln-, -Asp- and -Ac$_5$c-;

a bivalent radical of a dipeptide of the formula -(AA$^1$)-(AA$^2$)- wherein -(AA$^1$)- and -(AA$^2$)- are as recited above;

or a bivalent radical of an amino acid selected from the amino acids mentioned above; and Y is a monosubstituted amino selected from the group consisting of lower alkylamino, octylamino, halonaphthyloxy-lower alkylamino, naphthyloxy-lower alkylamino, phenyl-lower alkylamino, di-phenyl-lower alkylamino, (mono- or di-halophenyl)-lower alkylamino, naphthalenyl-lower alkylamino, hydroxy-naphthalenyl-lower alkylamino, phenanthrenyl-lower alkylamino; cycloalkylamino; and cycloalkyl-lower alkylamino;

or a salt thereof.

4. The compound of claim 1 wherein n is 1 to 4;

PTI is a bivalent radical of phosphotyrosine or of an amino acid selected from the group consisting of phosphonomethyl-phenylalanine, phosphono-(α-fluoro)methyl-phenylalanine, phosphono-(α,α-difluoro)methyl-phenylalanine, phosphono-(α-hydroxy)-methyl-phenylalanine, O-sulfo-tyrosine, dicarboxymethoxy-phenylalanine, aspartic acid, glutamic acid, phosphoserine and phosphothreonine, each of which is present in the (D,L)-, D- or L-form;

—(AA)$_n$— is a bivalent radical of a tripeptide of the formula -(AA$^1$)-(AA$^2$)-(AA$^3$)- wherein -(AA$^1$)- is selected from the group consisting of -Ile-, -Ac$_6$c-, -Asp-, -Gly- and -Phe-, -(AA$^2$)- is selected from the group consisting of -Asn-, -β-Ala- and -Gly-; and -(AA$^3$)- is selected from the group consisting of -Val-, -β-Ala-, -Gly-, -Gln-, -Asp- and -Ac$_5$c-;

a bivalent radical of a dipeptide of the formula -(AA$^1$)-(AA$^2$)- wherein -(AA$^1$)- is -Ile- or -Ac$_6$c- and -(AA$^2$)- is -Asn- or -β-Ala-;

or a bivalent radical of the amino acid selected from the amino acids mentioned above; and Y is a monosubstituted amino group having a substituent selected from the group consisting of lower alkyl and aryl-lower alkyl, or a salt thereof.

5. The compound of claim 1 wherein n is 1 to4;

PTI is a bivalent radical of an amino acid selected from the group consisting of phosphonomethyl-phenylalanine, phosphono-(α-fluoro)methyl-phenylalanine, phosphono-(α,α-difluoro)methyl-phenylalanine, phosphono-(α-hydroxy)methyl-phenylalanine, O-sulfo-tyrosine, dicarboxymethoxy-phenylalanine, aspartic acid, glutamic acid, phosphoserine and phosphothreonine, each of which is present in the (D,L)-, D- or the L-form;

—(AA)$_n$— is a bivalent radical of a tripeptide of the formula -(AA$^1$)-(AA$^2$)-(AA$^3$)- wherein -(AA$^1$)- is selected from the group consisting of -Ile-, -Ac$_5$c-, Ac$_6$c-, -Asp-, -Gly-, -Phe-, -Ac$_7$c-, -Nbo-, -Met-, -Pro-, -β-Ala-, -Gln-, -Glu-, -DHph-, -HPh- and -tLe-; -(AA$^2$)- is selected from the group consisting of -Asn-, -β-Ala-, -Gly-, -Ile-, and -Gln-; and -(AA$^3$)- is selected from the group consisting of -Val-, -β-Ala, -Gly-, -Gln-, -Asp- and -Ac$_5$c-; or a bivalent radical of an amino acid selected from the amino acids mentioned above; and Y is a monosubstituted amino selected from the group consisting of lower alkylamino, octylamino, halonaphthyloxy-lower alkylamino, naphthyloxy-lower alkylamino, phenyl-lower alkylamino, di-phenyl-lower alkylamino, (mono- or di-halo-phenyl)-lower alkylamino, naphthalenyl-lower alkylamino, hydroxy-naphthalenyl-lower alkylamino or phenanthrenyl-lower alkylamino, cycloalkylamino, and cycloalkyl-lower alkylamino;

or a salt thereof.

6. The compound of claim 1 wherein n is 1, 2 or 3;

PTI is a bivalent radical of phosphotyrosine, phosphono-(α,α-difluoro)methyl-phenylalanine, or phosphonomethyl-phenylalanine, —(AA)$_n$— is a bivalent radical of a tripeptide of the formula -(AA$^1$)-(AA$^2$)-(AA$^3$)- wherein (AA$^1$)- is selected from the group consisting of -Ile-, Ac$_5$c-, -Ac$_6$c-, -Asp-, -Gly-, -Phe-, -Ac$_7$c-, -Nbo-, -Met-, -Pro-, β-Ala-, -Gln-, -Glu-, -DHph-, -HPh-, and -tLe-; -(AA$^2$)- is selected from the group consisting of -Asn-, -β-Ala-, -Gly-, Ile-, and -Gln-; and -(AA$^3$)- is selected from -Val-, -β-Ala, -Gly-, -Gln-, -Asp- and -Ac$_5$c-;

a bivalent radical of a dipeptide of the formula -(AA$^1$)-(AA$^2$)- wherein -(AA$^1$) and -(AA$^2$)- are as recited above;

or a bivalent radical of an amino acid selected from the amino acids mentioned above; and Y is a monosubstituted amino selected from the group consisting of lower alkylamino, octylamino, halonaphthyloxy-lower alkylamino, or naphthyloxy-lower alkylamino, phenyl-lower alkylamino, (mono-or di-halo-phenyl)-lower alkylamino, naphthalenyl-lower alkylamino, hydroxy-naphthalenyl-lower alkylamino or phenanthrenyl-lower alkylamino, cycloalkylamino, and cycloalkyl-lower alkylamino, or a salt thereof.

7. The compound of claim 1 wherein n is 2 or 3;

PTI is a bivalent radical of phosphotyrosine or phosphono-(α,α-difluoro)methyl-phenylalanine, —(AA)$_n$— is a bivalent radical of a tripeptide of the formula -(AA$^1$)-(AA$^2$)-(AA$^3$)- wherein (AA$^1$)- is selected from the group consisting of -Ile, -Ac$_5$c-, -Ac$_6$c-, -Asp-, -Gly- and -Phe-; -(AA$^2$)- is selected from the group consisting of -Asn-, -β-Ala- and -Gly-; and -(AA$^3$)- is selected from the group consisting of -Val-, -β-Ala, -Gly-, -Gln-, -Asp-, and -Ac5c-;

or a bivalent radical or a dipeptide of the formula -(AA$^1$)-(AA$^2$)- wherein -(AA$^1$)- is -Ile- or -Ac$_6$c- and -(AA$^2$)- is -Asn- or -β-Ala-;

and Y is a naphthalenyl lower alkyl amino group, or a salt thereof.

8. The compound of claim 1 wherein n is 1, 2 or 3;

PTI is a bivalent radical of phosphotyrosine, phosphono-(α,α-difluoro)methyl-phenylalanine, or phosphonomethyl-phenylalanine;

—(AA)$_n$— is a bivalent radical of a tripeptide of the formula -(AA$^1$)-(AA$^2$)-(AA$^3$)- wherein -(AA$^1$)- is selected from the group consisting of -Ile-, Ac$_5$c-, -Ac$_6$c-, -Asp-, -Gly-, -Phe-, -Ac$_7$c-, -Nbo-, -Met-, -Pro-, -β-Ala-, -Gln-, -Glu-, -DHph-, -HPh- and -tLe-; -(AA$^2$)- is selected from the group consisting of -Asn-, -β-Ala-, -Gly-, -Ile-, and -Gln-; and -(AA$^3$)- is selected from the group consisting of -Val-, -β-Ala-, -Gly-, -Gln-, -Asp- and -Ac$_5$c-;

a bivalent radical of a dipeptide of the formula -(AA$^1$)-(AA$^2$)- wherein -(AA$^1$)- and -(AA$^2$)- are as recited above; or a bivalent radical of an amino acid selected from the amino acids mentioned above;

and Y is monosubstituted amino selected from the group consisting of lower alkylamino, octylamino, halonaphthyloxy-lower alkylamino or naphthyloxy-lower alkylamino, phenyl-lower alkylamino, di-phenyl-lower alkylamino, (mono- or di-halophenyl)-lower alkylamino, naphthalenyl-lower alkylamino, hydroxy-naphthalenyl-lower alkylamino or phenanthrenyl-lower alkylamino, cycloalkylamino, and cycloalkyl-lower alkylamino;

or a salt thereof.

9. The compound of claim 1 selected from the group consisting of oxalyl-Pmp-Ile-Asn-NH-(3-naphthalen-1-yl-propyl), oxalyl-Pmp-Ile-Asn-NH-(3-(2-hydroxy-naphthalen-1-yl)-propyl), oxalyl-Pmp-Ile-Asn-NH-(3-naphthalen-2-yl-propyl), and oxalyl-Pmp-Ac$_6$c-Asn-NH-(3-naphthalen-1-yl-propyl), wherein "Pmp" stands for phosphonomethyl phenylalenine.

10. The compound according to claim 1, wherein the compound is of the formula:

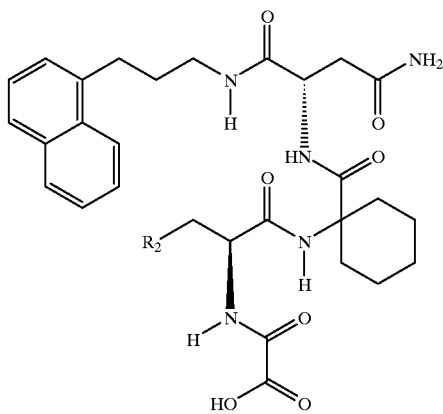

in which $R_2$ is a residue of phospho-tyrosine or a bivalent radical of an amino acid selected from the group consisting of phosphonomethyl-phenylalanine, phosphono-(α-fluoro)methyl-phenylalanine, phosphono-(α,α-difluoro)methyl-phenylalanine, phosphono-(α-hydroxy)methyl-phenylalanine, O-sulfo-tyrosine, phosphonophenylalanine, dicarboxymethoxy-phenylalanine, aspartic acid, glutamic acid, phosphoserine and phosphothreonine, each of which is present in the (D,L)-, D- or L-form.

11. The compound of claim 10 wherein $R_2$ is

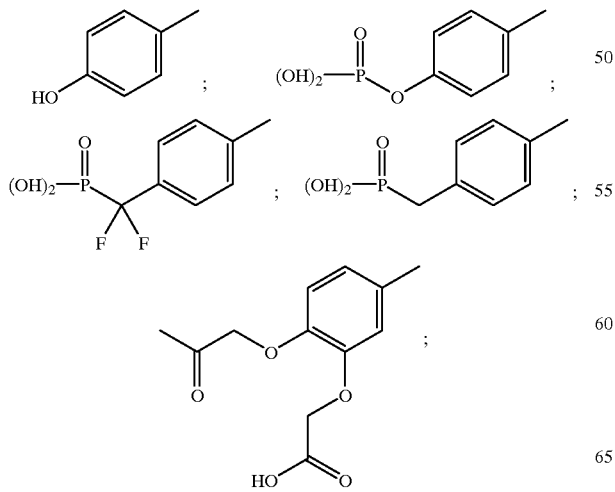

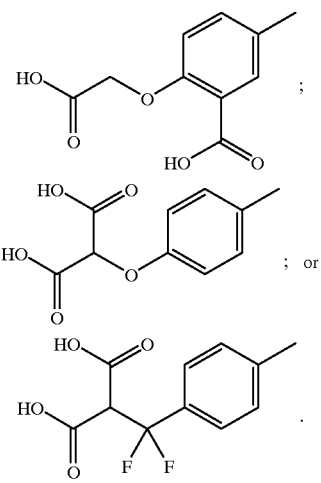

12. A pharmaceutical preparation comprising a compound of formula I, or a pharmaceutically acceptable salt thereof, according to any one of claims 1 to 10 and a pharmaceutically acceptable carrier material.

13. A compound of formula I, or a pharmaceutically acceptable salt thereof, according to any one of claims 1 to 10 for use in a method for the therapeutic or prophylactic treatment of the warm-blooded animal or human body.

14. The compound of claim 1, wherein PTI is a bivalent radical of phosphotyrosine or of an amino acid selected from the group consisting of 4-phosphonomethyl-phenylalanine, 4-phosphono-(α-fluoro)methyl-phenylalanine, 4-phosphono-(α,α-difluoro)methyl-phenylalanine, 4-phosphono-(α-hydroxy)methyl-phenylalanine, 4-(O-sulfo)-tyrosine, 4-phosphonophenylalanine, dicarboxymethoxy-phenylalanine, aspartic acid, glutamic acid, phosphoserine and phosphothreonine, each of which is present in the (D,L)-, D- or L-form.

15. A compound of the formula I,

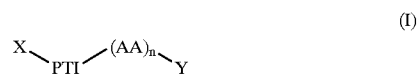

wherein n is 0 to 15,

X is oxalyl,

PTI is a bivalent radical of tyrosine or phosphotyrosine, or a bivalent radical of an amino acid selected from the group consisting of phosphonomethyl-phenylalanine, phosphono-(α-fluoro)methyl-phenylalanine, phosphono-(α,α-difluoro)methyl-phenylalanine, phosphono-(α-hydroxy)methyl-phenylalanine, O-sulfo-tyrosine, phosphonophenylalanine, dicarboxymethoxy-phenylalanine, aspartic acid, glutamic acid, phosphoserine and phosphothreonine, each of which is present in the (D,L)-, D- or L-form, AA stands for a bivalent radical of a natural or unnatural amino acid, and Y is a monosubstituted amino selected from the group consisting of lower alkylamino, octylamino, halonaphthyloxy-lower alkylamino, naphthyloxy-lower alkylamino, phenyl-lower alkylamino, di-phenyl-lower alkylamino, (mono- or di-halo-phenyl)-lower alkylamino, naphthalenyl-lower alkylamino, hydroxy-naphthalenyl-lower alkylamino, phenanthrenyl-lower alkylamino; cycloalkylamino; and cycloalkyl-lower alkylamino;
or a salt thereof.

16. A pharmaceutical preparation comprising a compound of formula I, or a pharmaceutically acceptable salt thereof, according to claim 14 and a pharmaceutically acceptable carrier material.

17. A pharmaceutical preparation comprising a compound of formula I, or a pharmaceutically acceptable salt thereof, according to claim 15 and a pharmaceutically acceptable carrier material.

18. A compound of formula I, or a pharmaceutically acceptable salt thereof, according to claim 14 for use in a method for the therapeutic or prophylactic treatment of the warm-blooded animal or human body.

19. A compound of formula I, or a pharmaceutically acceptable salt thereof, according to claim 15 for use in a method for the therapeutic or prophylactic treatment of the warm-blooded animal or human body.

* * * * *